United States Patent
Yano

(10) Patent No.: US 10,221,114 B2
(45) Date of Patent: *Mar. 5, 2019

(54) LIQUID CRYSTAL COMPOUND HAVING TETRAFLUORO CYCLOHEXADIENE STRUCTURE SHOWING NEGATIVE ANISOTROPY, LIQUID CRYSTAL COMPOSITION, AND LIQUID CRYSTAL DISPLAY DEVICE

(71) Applicants: JNC CORPORATION, Tokyo (JP); JNC PETROCHEMICAL CORPORATION, Tokyo (JP)

(72) Inventor: Tomohiro Yano, Chiba (JP)

(73) Assignees: JNC CORPORATION, Tokyo (JP); JNC PETROCHEMICAL CORPORATION, Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 15/023,366

(22) PCT Filed: Aug. 25, 2014

(86) PCT No.: PCT/JP2014/072163
§ 371 (c)(1),
(2) Date: Mar. 18, 2016

(87) PCT Pub. No.: WO2015/041006
PCT Pub. Date: Mar. 26, 2015

(65) Prior Publication Data
US 2016/0200980 A1    Jul. 14, 2016

(30) Foreign Application Priority Data
Sep. 19, 2013   (JP) .................. 2013-194025

(51) Int. Cl.
| | |
|---|---|
| C07C 23/18 | (2006.01) |
| C07C 43/225 | (2006.01) |
| C09K 19/04 | (2006.01) |
| C09K 19/30 | (2006.01) |
| C07D 213/26 | (2006.01) |
| C07D 239/26 | (2006.01) |
| C07D 309/04 | (2006.01) |
| C07D 319/06 | (2006.01) |
| C09K 19/32 | (2006.01) |
| C09K 19/34 | (2006.01) |
| C07C 25/18 | (2006.01) |

(52) U.S. Cl.
CPC ............ *C07C 23/18* (2013.01); *C07C 43/225* (2013.01); *C09K 19/0403* (2013.01); *C09K 19/3098* (2013.01); *C07C 25/18* (2013.01); *C07C 2601/14* (2017.05); *C07C 2601/16* (2017.05); *C07D 213/26* (2013.01); *C07D 239/26* (2013.01); *C07D 309/04* (2013.01); *C07D 319/06* (2013.01); *C09K 19/32* (2013.01); *C09K 2019/301* (2013.01); *C09K 2019/3004* (2013.01); *C09K 2019/3009* (2013.01); *C09K 2019/3016* (2013.01); *C09K 2019/3425* (2013.01)

(58) Field of Classification Search
CPC ........................... C07C 23/18; C09K 19/3098
See application file for complete search history.

(56) References Cited

U.S. PATENT DOCUMENTS

| | | | |
|---|---|---|---|
| 5,279,764 | A | 1/1994 | Reiffenrath et al. |
| 9,376,620 | B2 * | 6/2016 | Saito ............ C09K 19/3098 |
| 2011/0062384 | A1 * | 3/2011 | Yanai ............ C09K 19/126 |
| | | | 252/299.61 |

(Continued)

FOREIGN PATENT DOCUMENTS

| | | |
|---|---|---|
| JP | 2-4725 A | 1/1990 |
| JP | 2811342 B2 | 10/1998 |
| JP | 2004-43461 A | 2/2004 |
| JP | 2010-500980 A | 1/2010 |
| JP | 2012-116780 A | 6/2012 |
| WO | 89/08633 A1 | 9/1989 |
| WO | 2014/010665 A1 | 1/2014 |
| WO | 2014/125924 A1 | 8/2014 |

OTHER PUBLICATIONS

English Translation of WO2014010665.*

(Continued)

*Primary Examiner* — Cynthia H Kelly
*Assistant Examiner* — Anna Malloy
(74) *Attorney, Agent, or Firm* — Hauptman Ham, LLP

(57) ABSTRACT

A liquid crystal compound is represented by the formula (1). For example, in the formula (1): $R^1$ and $R^2$ each represent an alkyl having 1 to 10 carbon atoms, an alkenyl having 2 to 10 carbon atoms, or an alkoxy having 1 to 9 carbon atoms; a ring $A^1$ and a ring $A^2$ each represent 1,4-cyclohexylene or 1,4-phenylene; $Z^1$ and $Z^2$ each represent a single bond, —(CH$_2$)$_2$—, —CH═CH—, —COO—, —OCO—, —CF$_2$O—, —OCF$_2$—, —CH$_2$O—, or —OCH$_2$—; and a and b each represent 0, 1, 2, or 3 and the sum of a and b is 4 or less.

(1)

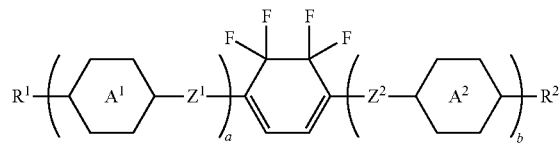

9 Claims, No Drawings

(56) References Cited

U.S. PATENT DOCUMENTS

2011/0253934 A1    10/2011    Lietzau et al.

OTHER PUBLICATIONS

Momota, K. et al., "Electrochemical Fluorination of aromatic compounds in liquid R4NF.mHF-part II. Fluorination of di- and tri-fluorobenzenes", Electrochemica Acta, vol. 39, No. 1, pp. 41-49, 1994.
"Chemical Abstracts", vol. 74, p. 372, 1971, No. 111649.
Kida, T. et al., "Synthesis of tetrafluorocyclohexadiene derivatives aiming for a novel negative type liquid crystal", Abstract of the Fluorine Conference of Japan, Oct. 3, 2013, vol. 36, pp. 74-75.
International Search Report dated Nov. 18, 2014, in International Application No. PCT/JP2014/072163.

* cited by examiner

LIQUID CRYSTAL COMPOUND HAVING TETRAFLUORO CYCLOHEXADIENE STRUCTURE SHOWING NEGATIVE ANISOTROPY, LIQUID CRYSTAL COMPOSITION, AND LIQUID CRYSTAL DISPLAY DEVICE

RELATED APPLICATIONS

The present application is a national phase of International Application Number PCT/JP2014/072163, filed Aug. 25, 2014 and claims priority from Japanese Application Number 2013-194025, filed Sep. 19, 2013.

TECHNICAL FIELD

The present invention relates to a liquid crystal compound, a liquid crystal composition, and a liquid crystal display device, and more specifically, to a compound having a tetrafluoro cyclohexadiene structure and showing negative dielectric anisotropy, a liquid crystal composition containing the compound, and a liquid crystal display device including the composition.

BACKGROUND ART

A liquid crystal display device has been widely used in displays of personal computers, televisions, and the like. This device employs optical anisotropy, dielectric anisotropy, and the like of a liquid crystal compound. The following operating modes have been known as operating modes of the liquid crystal display device: a phase change (PC) mode, a twisted nematic (TN) mode, a super twisted nematic (STN) mode, a bistable twisted nematic (BTN) mode, an electrically controlled birefringence (ECB) mode, an optically compensated bend (OCB) mode, an in-plane switching (IPS) mode, a vertical alignment (VA) mode, a fringe field switching (FFS) mode, a polymer sustained alignment (PSA), and the like.

In particular, the IPS mode, the FFS mode, and the VA mode are known to be able to widen a narrow viewing angle, which is a drawback of the operating modes such as the TN mode and the STN mode. In a liquid crystal display device having this type of mode, a liquid crystal composition having negative dielectric anisotropy is mainly used. In order to further improve the characteristics of the liquid crystal display device, it is preferred that a liquid crystal compound contained in the composition have the following physical properties (1) to (8).

(1) High stability to heat, light, and the like
(2) High clearing point
(3) Low minimum temperature of liquid crystal phase
(4) Small viscosity ($\eta$)
(5) Suitable optical anisotropy ($\Delta n$)
(6) Large negative dielectric anisotropy ($\Delta\varepsilon$)
(7) Suitable elastic constant ($K_{33}$: bend elastic constant)
(8) Excellent compatibility with other liquid crystal compounds The effects of the physical properties of the liquid crystal compound on the characteristics of the device are as described below. The compound having high stability to heat, light, and the like as in (1) increases the voltage holding ratio of the device. With this, the service life of the device is prolonged. The compound having a high clearing point as in (2) enlarges the temperature range in which the device can be used. The compound having a low minimum temperature of a liquid crystal phase, such as a nematic phase and a smectic phase, particularly having a low minimum temperature of a nematic phase as in (3) also enlarges the temperature range in which the device can be used. The compound having a small viscosity as in (4) shortens the response time of the device.

The compound having suitable optical anisotropy as in (5) improves the contrast of the device. Depending on the design of the device, a compound having large optical anisotropy or small optical anisotropy, that is, suitable optical anisotropy is required. In the case of shortening the response time by reducing a cell gap of the device, a compound having large optical anisotropy is suitable. The compound having large negative dielectric anisotropy as in (6) decreases the threshold voltage of the device. With this, the power consumption of the device is decreased.

Regarding (7), the compound having a large elastic constant shortens the response time of the device. The compound having a small elastic constant decreases the threshold voltage of the device. Thus, a suitable elastic constant is required depending on the characteristics intended to be improved. A compound having excellent compatibility with other liquid crystal compounds as in (8) is preferred. This is because liquid crystal compounds having different physical properties are mixed to regulate the physical properties of the composition.

Hitherto, as a component of the liquid crystal composition having negative dielectric anisotropy ($\Delta\varepsilon$), a large number of liquid crystal compounds in which hydrogen at a lateral position of a benzene ring is substituted by fluorine have been investigated (Patent Literature 1 and Patent Literature 2). For example, a compound (a) has been reported. However, although the compound (a) has negative dielectric anisotropy ($\Delta\varepsilon$), the value thereof is not necessarily large in some cases, and hence the value is not sufficient for decreasing the drive voltage of a liquid crystal display device in a VA mode, an IPS mode, and the like in some cases.

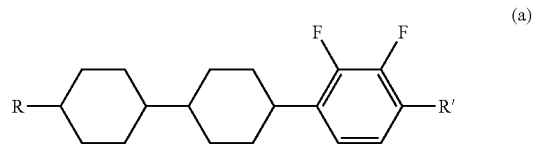

(a)

Under such circumstances, there is a demand for the development of a compound having excellent physical properties and suitable balance regarding the above-mentioned physical properties (1) to (8). In particular, there is a demand for a compound having large negative dielectric anisotropy.

CITATION LIST

Patent Literature

[PTL 1] JP 2811342 B2
[PTL 2] JP 02-4725 A

SUMMARY OF INVENTION

Technical Problem

A first object of the present invention is to provide a liquid crystal compound that satisfies at least one of physical properties such as high stability to heat, light, and the like, a high clearing point, a low minimum temperature of a liquid crystal phase, a small viscosity, suitable optical anisotropy, large negative dielectric anisotropy, a suitable elastic constant, and excellent compatibility with other liquid crystal compounds. In particular, the object is to provide a compound having large negative dielectric anisotropy. A second object of the present invention is to provide a liquid crystal composition that contains the compound and satisfies at least one of physical properties such as a high maximum temperature of a nematic phase, a low minimum temperature of a nematic phase, a small viscosity, suitable optical anisotropy, large negative dielectric anisotropy, and a suitable elastic constant. The object is to provide a liquid crystal composition having suitable balance regarding at least two physical properties. A third object of the present invention is to provide a liquid crystal display device that includes the composition and has a wide temperature range in which the device can be used, a short response time, a large voltage holding ratio, a low threshold voltage, a large contrast ratio, and a long service life.

Solution to Problem

The present invention relates to a compound represented by the following formula (1), a liquid crystal composition containing the compound, and a liquid crystal display device including the liquid crystal composition.

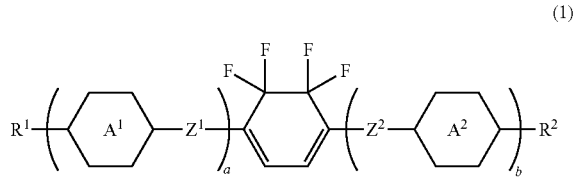

(1)

In the formula (1):

$R^1$ and $R^2$ independently represent hydrogen, a halogen, or an alkyl having 1 to 20 carbon atoms, in the alkyl, at least one —$CH_2$— may be substituted by —O— or —S— and at least one —$(CH_2)_2$— may be substituted by —CH=CH—, and in the groups, at least one hydrogen may be substituted by a halogen;

a ring $A^1$ and a ring $A^2$ independently represent 1,4-cyclohexylene, 1,4-cyclohexenylene, 1,4-phenylene, 1,4-phenylene in which at least one hydrogen is substituted by a halogen, tetrahydropyran-2,5-diyl, 1,3-dioxane-2,5-diyl, pyrimidine-2,5-diyl, 2,6,7-trioxabicyclo[2.2.2]octane-1,4-diyl, naphthalene-2,6-diyl, naphthalene-2,6-diyl in which at least one hydrogen is substituted by a halogen, pyridine-2,5-diyl, or 5,5,6,6-tetrafluoro-1,3-cyclohexadiene-1,4-diyl;

$Z^1$ and $Z^2$ independently represent a single bond or an alkylene having 1 to 4 carbon atoms, in the alkylene, at least one —$CH_2$— may be substituted by —O— or —COO— and at least one —$(CH_2)_2$— may be substituted by —CH=CH— or —C≡C—, and in the groups, at least one hydrogen may be substituted by a halogen; and a and b independently represent 0, 1, 2, 3, or 4, a sum of a and b is 4 or less, and when a or b represents 2 or more, any two rings $A^1$, any two rings $A^2$, any two $Z^1$'s, or any two $Z^2$'s may be identical to or different from each other.

Advantageous Effects of Invention

A first advantage of the present invention is to provide a liquid crystal compound that satisfies at least one of physical properties such as high stability to heat, light, and the like, a high clearing point, a low minimum temperature of a liquid crystal phase, a small viscosity, suitable optical anisotropy, large negative dielectric anisotropy, a suitable elastic constant, and excellent compatibility with other liquid crystal compounds. In particular, the advantage is to provide a compound having large negative dielectric anisotropy. A second advantage of the present invention is to provide a liquid crystal composition that contains the compound and satisfies at least one of physical properties such as a high maximum temperature of a nematic phase, a low minimum temperature of a nematic phase, a small viscosity, suitable optical anisotropy, large negative dielectric anisotropy, and a suitable elastic constant. The advantage is to provide a liquid crystal composition having suitable balance regarding at least two physical properties. A third advantage of the present invention is to provide a liquid crystal display device that includes the composition and has a wide temperature range in which the device can be used, a short response time, a large voltage holding ratio, a low threshold voltage, a large contrast ratio, and a long service life.

DESCRIPTION OF EMBODIMENTS

The terms in this description are used as described below. A liquid crystal compound is a collective term of a compound that has a liquid crystal phase, such as a nematic phase or a smectic phase, and a compound that does not have a liquid crystal phase but is useful as a component of a liquid crystal composition. The liquid crystal compound, the liquid crystal composition, and a liquid crystal display device are sometimes abbreviated as "compound", "composition", and "device", respectively. The liquid crystal display device is a collective term of a liquid crystal display panel and a liquid crystal display module. A clearing point refers to a transition temperature of a liquid crystal-isotropic phase in the liquid crystal compound. A minimum temperature of a liquid crystal phase refers to a transition temperature of a solid-liquid crystal phase (smectic phase, nematic phase, etc.) in the liquid crystal compound. A maximum temperature of a nematic phase refers to a transition temperature of a nematic-isotropic phase in the liquid crystal composition and is sometimes abbreviated as "maximum temperature". A minimum temperature of a nematic phase is sometimes abbreviated as "minimum temperature". A compound represented by the formula (1) is sometimes abbreviated as "compound (1)". A composition containing the compound represented by the formula (1) is sometimes abbreviated as "composition (1)". This abbreviation is also applied to a compound represented by the formula (2) or the like in some cases. In the formula (1), the formula (2), and the like, symbols $A^1$, $D^1$, and the like surrounded by hexagons correspond to a ring $A^1$, a ring $D^1$, and the like, respectively. A plurality of rings $A^1$ are described in one formula or different formulae. In those compounds, two groups represented by any two rings $A^1$ may be identical to or different from each other. This rule is also applied to symbols such as a ring $A^2$ and a ring $Z^2$. This rule is also applied to two rings $A^1$ when a represents 2. The amount of a compound represented by a percentage is a weight percentage (wt %) based on the total weight of the composition.

The expression "at least one "A" may be substituted by "B"" means that, when there is one "A", the position of "A" is arbitrary, and even when the number of "A"s is two or more, the positions can be selected without any limitation. The expression "at least one A may be substituted by B, C, or D" means that the case where any A is substituted by B, the case where any A is substituted by C, and the case where any A is substituted by D are included, and the case where a plurality of A's are substituted by at least two of B, C, or D is further included. For example, an alkyl in which at least one —CH$_2$— may be substituted by —O— or —CH=CH— includes an alkyl, an alkenyl, an alkoxy, an alkoxyalkyl, an alkoxyalkenyl, and an alkenyloxyalkyl. It is not preferred that two consecutive —CH$_2$—'s be substituted by —O— to form —O—O—. Further, it is not preferred that —CH$_2$— of a methyl moiety (—CH$_2$—H) in the alkyl or the like be substituted by —O— to form —O—H.

2-Fluoro-1,4-phenylene refers to the following two divalent groups. In the chemical formula, fluorine may be left-pointing (L) or right-pointing (R). This rule is also applied to an asymmetric divalent ring, such as tetrahydropyran-2,5-diyl.

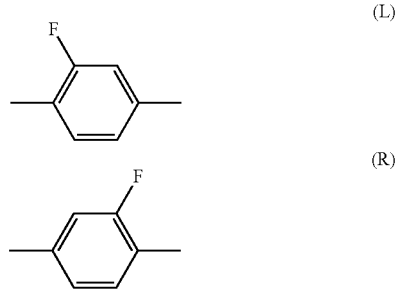

The present invention encompasses the contents described in Items 1 to 17 below.

Item 1. A compound, which is represented by the following formula (1):

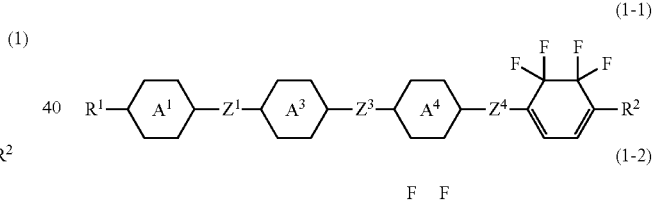

in the formula (1):

R$^1$ and R$^2$ independently represent hydrogen, a halogen, or an alkyl having 1 to 20 carbon atoms, in the alkyl, at least one —CH$_2$— may be substituted by —O— or —S— and at least one —(CH$_2$)$_2$— may be substituted by —CH=CH—, and in the groups, at least one hydrogen may be substituted by a halogen;

a ring A$^1$ and a ring A$^2$ each independently represent 1,4-cyclohexylene, 1,4-cyclohexenylene, 1,4-phenylene, 1,4-phenylene in which at least one hydrogen is substituted by a halogen, tetrahydropyran-2,5-diyl, 1,3-dioxane-2,5-diyl, pyrimidine-2,5-diyl, 2,6,7-trioxabicyclo[2.2.2]octane-1,4-diyl, naphthalene-2,6-diyl, naphthalene-2,6-diyl in which at least one hydrogen is substituted by a halogen, pyridine-2,5-diyl, or 5,5,6,6-tetrafluoro-1,3-cyclohexadiene-1,4-diyl;

Z$^1$ and Z$^2$ each independently represent a single bond or an alkylene having 1 to 4 carbon atoms, in the alkylene, at least one —CH$_2$— may be substituted by —O— or —COO— and at least one —(CH$_2$)$_2$— may be substituted by —CH=CH— or —C≡C—, and in the groups, at least one hydrogen may be substituted by a halogen; and a and b each independently represent 0, 1, 2, 3, or 4, a sum of a and b is 4 or less, and when a or b represents 2 or more, any two rings A$^1$, any two rings A$^2$, any two Z$^1$'s, or any two Z$^2$'s may be identical to or different from each other.

Item 2. A compound according to Item 1, in which, in the formula (1), Z$^1$ and Z$^2$ each independently represent a single bond, —(CH$_2$)$_2$—, —CH=CH—, —CF=CF—, —C≡C—, —COO—, —OCO—, —CF$_2$O—, —OCF$_2$—, —CH$_2$O—, —OCH$_2$—, —(CH$_2$)$_4$—, —(CH$_2$)$_2$CF$_2$O—, —(CH$_2$)$_2$OCF$_2$—, —CF$_2$O(CH$_2$)$_2$—, —OCF$_2$(CH$_2$)$_2$—, —CH=CH—(CH$_2$)$_2$—, or —(CH$_2$)$_2$—CH=CH—.

Item 3. A compound according to Item 1 or 2, in which, in the formula (1):

R$^1$ and R$^2$ each independently represent hydrogen, fluorine, chlorine, or an alkyl having 1 to 10 carbon atoms, in the alkyl, at least one —CH$_2$— may be substituted by —O— and at least one —(CH$_2$)$_2$— may be substituted by —CH=CH—, and in the groups, at least one hydrogen may be substituted by fluorine or chlorine;

the ring A$^1$ and the ring A$^2$ each independently represent 1,4-cyclohexylene, 1,4-cyclohexenylene, 1,4-phenylene, 1,4-phenylene in which at least one hydrogen is substituted by a halogen, tetrahydropyran-2,5-diyl, or 5,5,6,6-tetrafluoro-1,3-cyclohexadiene-1,4-diyl; and Z$^1$ and Z$^2$ each independently represent a single bond, —(CH$_2$)$_2$—, —CH=CH—, —COO—, —OCO—, —CF$_2$O—, —OCF$_2$—, —CH$_2$O—, or —OCH$_2$—.

Item 4. A compound according to any one of Items 1 to 3, in which, in the formula (1), a sum of a and b is 1, 2, or 3.

Item 5. A compound according to Item 1, in which the compound is represented by any one of the following formulae (1-1) to (1-5):

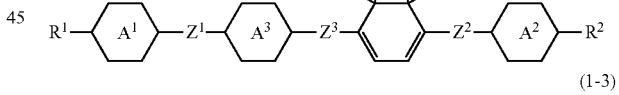

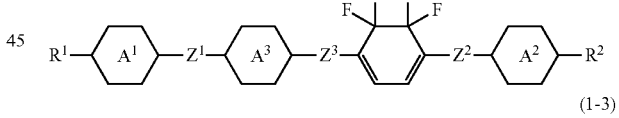

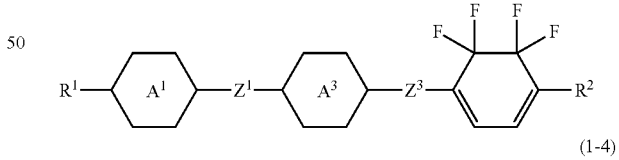

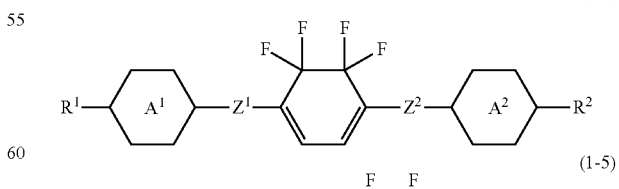

in the formulae (1-1) to (1-5):

$R^1$ and $R^2$ each independently represent hydrogen, fluorine, an alkyl having 1 to 10 carbon atoms, an alkenyl having 2 to 10 carbon atoms, an alkoxy having 1 to 9 carbon atoms, or an alkenyloxy having 2 to 9 carbon atoms, and in the groups, at least one hydrogen may be substituted by fluorine;

a ring $A^1$, a ring $A^2$, a ring $A^3$, and a ring $A^4$ each independently represent 1, 4-cyclohexylene, 1, 4-cyclohexenylene, 1,4-phenylene, 1,4-phenylene in which at least one hydrogen is substituted by a halogen, tetrahydropyran-2,5-diyl, or 5,5,6,6-tetrafluoro-1,3-cyclohexadiene-1,4-diyl; and $Z^1$, $Z^2$, $Z^3$, and $Z^4$ each independently represent a single bond, —$(CH_2)_2$—, —CH=CH—, —COO—, —OCO—, —$CF_2O$—, —$OCF_2$—, —$CH_2O$—, or —$OCH_2$—.

Item 6. A compound according to Item 5, in which, in the formulae (1-1) to (1-5), at least one of $Z^1$, $Z^2$, $Z^3$, or $Z^4$ represents —$(CH_2)_2$—, —CH=CH—, —COO—, —OCO—, —$CF_2O$—, —$OCF_2$—, —$CH_2O$—, or —$OCH_2$—.

Item 7. A compound according to Item 1, in which the compound is represented by any one of the following formulae (1-6) to (1-10):

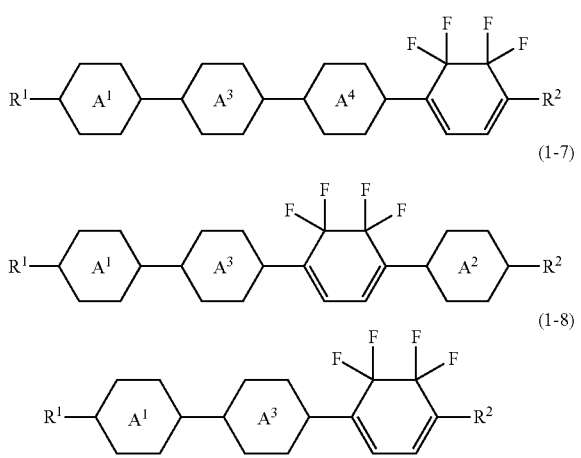

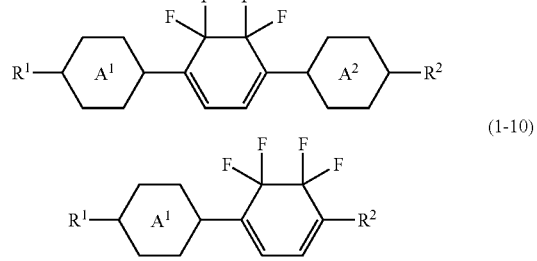

in the formulae (1-6) to (1-10):

$R^1$ and $R^2$ each independently represent hydrogen, fluorine, an alkyl having 1 to 10 carbon atoms, an alkenyl having 2 to 10 carbon atoms, an alkoxy having 1 to 9 carbon atoms, or an alkenyloxy having 2 to 9 carbon atoms, and in the groups, at least one hydrogen may be substituted by fluorine; and a ring $A^1$, a ring $A^2$, a ring $A^3$, and a ring $A^4$ each independently represent 1, 4-cyclohexylene, 1, 4-cyclohexenylene, 1,4-phenylene, 1,4-phenylene in which at least one hydrogen is substituted by a halogen, tetrahydropyran-2,5-diyl, or 5,5,6,6-tetrafluoro-1,3-cyclohexadiene-1,4-diyl.

Item 8. A compound according to Item 7, in which, in the formulae (1-6) to (1-10), the ring $A^1$, the ring $A^2$, the ring $A^3$, and the ring $A^4$ each independently represent 1, 4-cyclohexylene, 1,4-phenylene, 1,4-phenylene in which at least one hydrogen is substituted by a halogen, or tetrahydropyran-2,5-diyl.

Item 9. A compound according to Item 7 or 8, in which the compound is represented by the formula (1-6), (1-8), or (1-10), and $R^2$ represents hydrogen.

Item 10. A liquid crystal composition, including at least one of the compounds of Items 1 to 9.

Item 11. A liquid crystal composition according to Item 10, further including at least one compound selected from the group consisting of compounds represented by the following formulae (6) to (12):

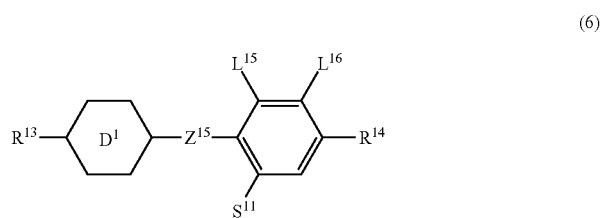

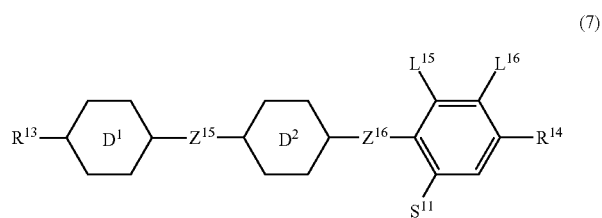

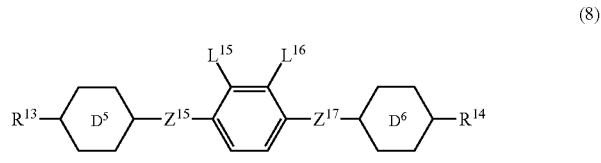

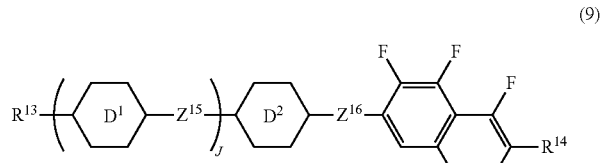

-continued

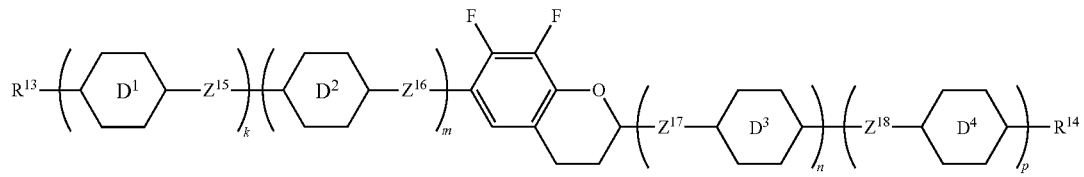

(10)

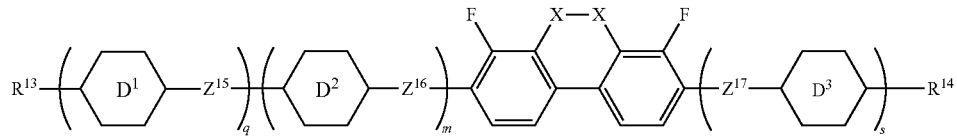

(11)

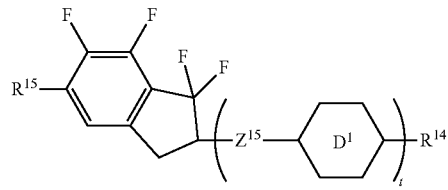

(12)

in the formulae (6) to (12):

$R^{13}$ represents an alkyl having 1 to 10 carbon atoms or an alkenyl having 2 to 10 carbon atoms, and in the alkyl and the alkenyl, at least one —$CH_2$— may be substituted by —O— and at least one hydrogen may be substituted by fluorine;

$R^{14}$ represents an alkyl having 1 to 10 carbon atoms, and in the alkyl, at least one —$CH_2$— may be substituted by —O— and at least one hydrogen may be substituted by fluorine;

$R^{15}$ represents hydrogen, fluorine, an alkyl having 1 to 10 carbon atoms, or an alkenyl having 2 to 10 carbon atoms, and in the alkyl and the alkenyl, at least one —$CH_2$— may be substituted by —O— and at least one hydrogen may be substituted by fluorine;

$S^{11}$ represents hydrogen or methyl;

X represents —$CF_2$—, —O—, or —CHF—;

a ring $D^1$, a ring $D^2$, a ring $D^3$, and a ring $D^4$ each independently represent 1,4-cyclohexylene, 1,4-cyclohexenylene, 1,4-phenylene in which at least one hydrogen may be substituted by fluorine, tetrahydropyran-2,5-diyl, or decahydronaphthalene-2,6-diyl; a ring $D^5$ and a ring $D^6$ each independently represent 1,4-cyclohexylene, 1,4-cyclohexenylene, 1,4-phenylene, tetrahydropyran-2,5-diyl, or decahydronaphthalene-2,6-diyl;

$Z^{15}$, $Z^{16}$, $Z^{17}$, and $Z^{18}$ each independently represent a single bond, —$CH_2CH_2$—, —COO—, —$CH_2O$—, —$OCF_2$—, or —$OCF_2CH_2CH_2$—;

$L^{15}$ and $L^{16}$ each independently represent fluorine or chlorine; and j, k, m, n, p, q, r, and s each independently represent 0 or 1, a sum of k, m, n, and p is 1 or 2, a sum of q, r, and s is 0, 1, 2, or 3, and t represents 1, 2, or 3.

Item 12. A liquid crystal composition according to Item 10 or 11, further including at least one compound selected from the group consisting of compounds represented by the following formulae (13) to (15):

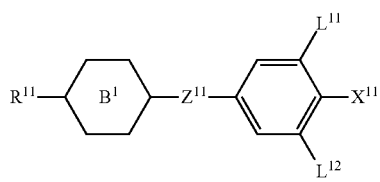

(13)

-continued

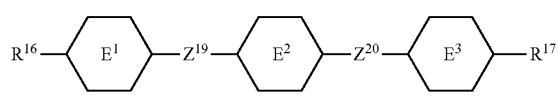

(14)

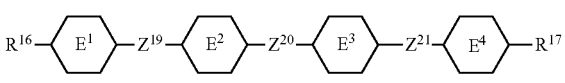

(15)

in the formulae (13) to (15):

$R^{16}$ and $R^{17}$ each independently represent an alkyl having 1 to 10 carbon atoms or an alkenyl having 2 to 10 carbon atoms, and in the alkyl and the alkenyl, at least one —$CH_2$— may be substituted by —O— and at least one hydrogen may be substituted by fluorine;

a ring $E^1$, a ring $E^2$, a ring $E^3$, and a ring $E^4$ each independently represent 1,4-cyclohexylene, 1,4-phenylene, 2-fluoro-1,4-phenylene, 2,5-difluoro-1,4-phenylene, or pyrimidine-2,5-diyl; and $Z^{19}$, $Z^{20}$, and $Z^{21}$ each independently represent a single bond, —$CH_2CH_2$—, —CH=CH—, —C≡C—, or —COO—.

Item 13. A liquid crystal composition according to any one of Items 10 to 12, further including at least one compound selected from the group consisting of compounds represented by the following formulae (2) to (4):

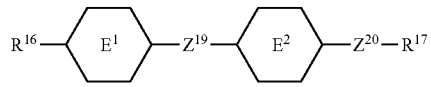

(2)

-continued (3)

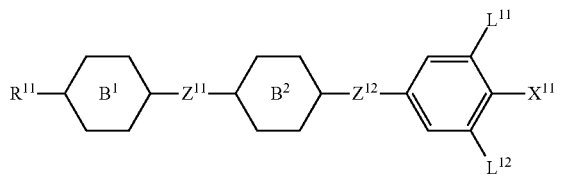

(4)

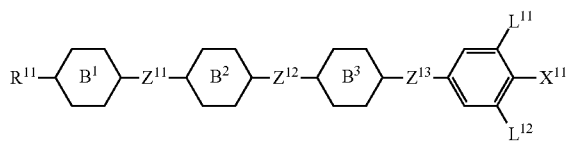

in the formulae (2) to (4):

$R^{11}$ represents an alkyl having 1 to 10 carbon atoms or an alkenyl having 2 to 10 carbon atoms, and in the alkyl and the alkenyl, at least one hydrogen may be substituted by fluorine and at least one —$CH_2$— may be substituted by —O—;

$X^{11}$ represents fluorine, chlorine, —$OCF_3$, —$OCHF_2$, —$CF_3$, —$CHF_2$, —$CH_2F$, —$OCF_2CHF_2$, or —$OCF_2CHFCF_3$;

a ring $B^1$, a ring $B^2$, and a ring $B^3$ each independently represent 1,4-cyclohexylene, 1,4-phenylene in which at least one hydrogen may be substituted by fluorine, tetrahydropyran-2,5-diyl, 1,3-dioxane-2,5-diyl, or pyrimidine-2,5-diyl;

$Z^{11}$, $Z^{12}$, and $Z^{13}$ each independently represent a single bond, —$CH_2CH_2$—, —CH=CH—, —C≡C—, —COO—, —$CF_2O$—, —$OCF_2$—, —$CH_2O$—, or —$(CH_2)_4$—; and $L^{11}$ and $L^{12}$ each independently represent hydrogen or fluorine.

Item 14. A liquid crystal composition according to any one of Items 10 to 13, further including at least one compound selected from the group consisting of compounds represented by the following formula (5):

(5)

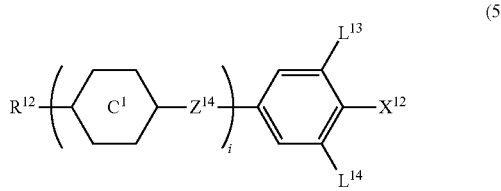

in the formula (5):

$R^{12}$ represents an alkyl having 1 to 10 carbon atoms or an alkenyl having 2 to 10 carbon atoms, and in the alkyl and the alkenyl, at least one hydrogen may be substituted by fluorine and at least one —$CH_2$— may be substituted by —O—;

$X^{12}$ represents —C≡N or —C≡C—C≡N;

a ring $C^1$ represents 1, 4-cyclohexylene, 1, 4-phenylene in which at least one hydrogen may be substituted by fluorine, tetrahydropyran-2,5-diyl, 1,3-dioxane-2,5-diyl, or pyrimidine-2,5-diyl;

$Z^{14}$ represents a single bond, —$CH_2CH_2$—, —C≡C—, —COO—, —$CF_2O$—, —$OCF_2$—, or —$CH_2O$—;

$L^{13}$ and $L^{14}$ each independently represent hydrogen or fluorine; and i represents 1, 2, 3, or 4.

Item 15. A liquid crystal composition according to any one of Items 10 to 14, further including at least one optically active compound and/or polymerizable compound.

Item 16. A liquid crystal composition according to any one of Items 10 to 15, further including at least one antioxidant and/or UV absorber.

Item 17. A liquid crystal display device, including the liquid crystal composition of any one of Items 10 to 16.

The compound, the liquid crystal composition, and the liquid crystal display device of the present invention are described in the stated order.

1-1. Compound (1)

A compound (1) of the present invention is described. Preferred examples of a terminal group, a ring structure, and a linking group in the compound (1), and the effects of the groups on the physical properties are also applied to the sub-formula of the compound (1).

(1)

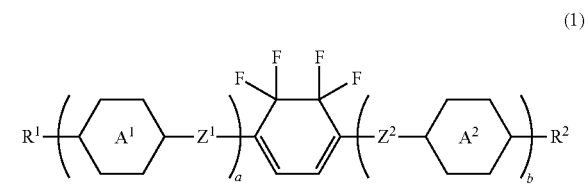

In the formula (1), $R^1$ and $R^2$ each independently represent hydrogen, a halogen, or an alkyl having 1 to 20 carbon atoms, in the alkyl, at least one —$CH_2$— may be substituted by —O— or —S— and at least one —$(CH_2)_2$— may be substituted by —CH=CH—, and in the groups, at least one hydrogen may be substituted by a halogen. Those groups are a straight chain or a branched chain, and do not include a cyclic group, such as cyclohexyl. In those groups, a straight chain is more preferred than a branched chain.

The preferred configuration of —CH=CH— in an alkenyl depends on the position of a double bond. In an alkenyl having a double bond at an odd-numbered position, such as —CH=CHCH_3, —CH=CHC_2H_5, —CH=CHC_3H_7, —CH=CHC_4H_9, —C_2H_4CH=CHCH_3, or —C_2H_4CH=CHC_2H_5, a trans configuration is preferred. In an alkenyl having a double bond at an even-numbered position, such as —CH_2CH=CHCH_3, —CH_2CH=CHC_2H_5, or —CH_2CH=CHC_3H_7, a cis configuration is preferred. An alkenyl compound having a preferred configuration has a high clearing point or a wide temperature range of a liquid crystal phase. There are detailed descriptions in Mol. Cryst. Liq. Cryst., 1985, 131, 109 and Mol. Cryst. Liq. Cryst., 1985, 131, 327.

Preferred examples of $R^1$ or $R^2$ include an alkyl, an alkoxy, an alkenyl, and an alkenyloxy. More preferred examples of $R^1$ or $R^2$ include an alkyl, an alkoxy, and an alkenyl.

Examples of the alkyl include —$CH_3$, —$C_2H_5$, —$C_3H_7$, —$C_4H_9$, —$C_5H_{11}$, —$C_6H_{13}$, —$C_7H_{15}$, —$C_8H_{17}$, —$C_9H_{19}$, —$C_{10}H_{21}$, —$C_{11}H_{23}$, —$C_{12}H_{25}$, —$C_{13}H_{27}$, —$C_{14}H_{29}$, and —$C_{15}H_{31}$.

Examples of the alkoxy include —$OCH_3$, —$OC_2H_5$, —$OC_3H_7$, —$OC_4H_9$, —$OC_5H_{11}$, —$OC_6H_{13}$, —$OC_7H_{15}$, —$OC_8H_{17}$, —$OC_9H_{19}$, —$OC_{10}H_{21}$, —$OC_{11}H_{23}$, —$OC_{12}H_{25}$, —$OC_{13}H_{27}$, and —$OC_{14}H_{29}$.

As an alkoxyalkyl, there are given, for example, —$CH_2OCH_3$, —$CH_2OC_2H_5$, —$CH_2OC_3H_7$, —$(CH_2)_2$—$OCH_3$, —$(CH_2)_2$—$OC_2H_5$, —$(CH_2)_2$—$OC_3H_7$, —$(CH_2)_3$—$OCH_3$, —$(CH_2)_4$—$OCH_3$, and —$(CH_2)_5$—$OCH_3$.

Examples of the alkenyl include —CH═CH$_2$, —CH═CHCH$_3$, —CH$_2$CH═CH$_2$, —CH═CHC$_2$H$_5$, —CH$_2$CH═CHCH$_3$, —(CH$_2$) 2-CH═CH$_2$, —CH═CHC$_3$H$_7$, —CH$_2$CH═CHC$_2$H$_5$, —(CH$_2$)$_2$—CH═CHCH$_3$, and —(CH$_2$)$_3$—CH═CH$_2$.

Examples of the alkenyloxy include —OCH$_2$CH═CH$_2$, —OCH$_2$CH═CHCH$_3$, and —OCH$_2$CH═CHC$_2$H$_5$.

As an alkyl in which at least one hydrogen is substituted by a halogen, there are given, for example, —CH$_2$F, —CHF$_2$, —CF$_3$, —(CH$_2$)$_2$—F, —CF$_2$CH$_3$, —CF$_2$CH$_2$F, —CF$_2$CHF$_2$, —CH$_2$CF$_3$, —CF$_2$CF$_3$, —(CH$_2$)$_3$—F, —CF$_2$CH$_2$CH$_3$, —CH$_2$CHFCH$_3$, —CH$_2$CF$_2$CH$_3$, —(CF$_2$)$_3$—F, —CF$_2$CHFCF$_3$, —CHFCF$_2$CF$_3$, —(CH$_2$)$_4$—F, —CF$_2$ (CH$_2$)$_2$CH$_3$, —(CF$_2$)$_4$—F, —(CH$_2$)$_5$—F, —(CF$_2$)$_5$—F, —CH$_2$Cl, —CHCl$_2$, —CCl$_3$, —(CH$_2$)$_2$—Cl, —CCl$_2$CH$_3$, —CCl$_2$CH$_2$Cl, —CCl$_2$CHCl$_2$, —CH$_2$CCl$_3$, —CCl$_2$CCl$_3$, —(CH$_2$)$_3$—Cl, —CCl$_2$CH$_2$CH$_3$, —(CCl$_2$)$_3$—Cl, —CCl$_2$CHClCCl$_3$, —CHClCCl$_2$CCl$_3$, —(CH$_2$)$_4$—Cl, —(CCl$_2$)$_4$—Cl, —CCl$_2$ (CH$_2$)$_2$CH$_3$, —(CH$_2$)$_5$—Cl, and —(CCl$_2$)$_5$—C.

As an alkoxy in which at least one hydrogen is substituted by a halogen, there are given, for example, —OCH$_2$F, —OCHF$_2$, —OCF$_3$, —O—(CH$_2$)$_2$—F, —OCF$_2$CH$_2$F, —OCF$_2$CHF$_2$, —OCH$_2$CF$_3$, —O—(CH$_2$)$_3$—F, —O—(CF$_2$)$_3$—F, —OCF$_2$CHFCF$_3$, —OCHFCF$_2$CF$_3$, —O(CH$_2$)$_4$—F, —O—(CF$_2$)$_4$—F, —O—(CH$_2$)$_5$—F, —O—(CF$_2$)$_5$—F, —OCH$_2$CHFCH$_2$CH$_3$, —OCH$_2$Cl, —OCHCl$_2$, —OCCl$_3$, —O—(CH$_2$)$_2$—Cl, —OCCl$_2$CH$_2$Cl, —OCCl$_2$CHCl$_2$, —OCH$_2$CCl$_3$, —O—(CH$_2$)$_3$—Cl, —O—(CCl$_2$)$_3$—Cl, —OCCl$_2$CHClCCl$_3$, —OCHClCCl$_2$CCl$_3$, —O(CH$_2$)$_4$—Cl, —O—(CCl$_2$)$_4$—Cl, —O—(CH$_2$)$_5$—Cl, and —O—(CCl$_2$)$_5$—Cl.

As an alkenyl in which at least one hydrogen is substituted by a halogen, there are given, for example, —CH═CHF, —CH═CF$_2$, —CF═CHF, —CH═CHCH$_2$F, —CH═CHCF$_3$, —(CH$_2$)$_2$—CH═CF$_2$, —CH$_2$CH═CHCF$_3$, —CH═CHCF$_2$CF$_3$, —CH═CHCl, —CH═CCl$_2$, —CCl═CHCl, —CH═CHCH$_2$Cl, —CH═CHCCl$_3$, —(CH$_2$)$_2$—CH═CCl$_2$, —CH$_2$CH═CHCCl$_3$, and —CH═CHCCl$_2$CCl$_3$.

The ring A$^1$ and the ring A$^2$ in the formula (1) each independently represent 1,4-cyclohexylene, 1,4-cyclohexenylene, 1,4-phenylene, 1,4-phenylene in which at least one hydrogen is substituted by a halogen, tetrahydropyran-2,5-diyl, 1,3-dioxane-2,5-diyl, pyrimidine-2,5-diyl, 2,6,7-trioxabicyclo[2.2.2]octane-1,4-diyl, naphthalene-2,6-diyl, naphthalene-2, 6-diyl in which at least one hydrogen is substituted by a halogen, pyridine-2,5-diyl, or 5,5,6,6-tetrafluoro-1,3-cyclohexadiene-1,4-diyl.

Preferred examples of the ring A$^1$ or the ring A$^2$ include 1,4-cyclohexylene, 1,4-cyclohexenylene, 1,4-phenylene, 1,4-phenylene in which at least one hydrogen is substituted by a halogen, tetrahydropyran-2,5-diyl, and 5,5,6,6-tetrafluoro-1,3-cyclohexadiene-1,4-diyl. More preferred examples thereof include 1,4-cyclohexylene, 1,4-phenylene, 1,4-phenylene in which at least one hydrogen is substituted by a halogen, tetrahydropyran-2,5-diyl, and 5,5,6,6-tetrafluoro-1,3-cyclohexadiene-1,4-diyl. 1,4-Cyclohexylene has cis and trans configurations. Of those, a trans configuration is preferred from the viewpoint of a higher maximum temperature.

Preferred examples of the 1,4-phenylene in which at least one hydrogen is substituted by a halogen include groups represented by the following formulae (A-1) to (A-17). The group represented by the formula (A-1), (A-5), (A-6), (A-7), (A-8), (A-9), (A-10), or (A-11) is more preferred in order for the compound to have large negative dielectric anisotropy.

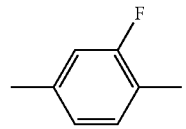
(A-1)

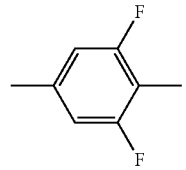
(A-2)

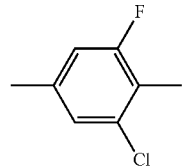
(A-3)

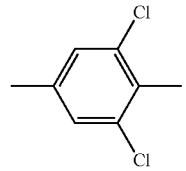
(A-4)

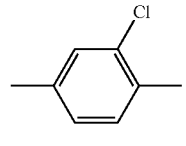
(A-5)

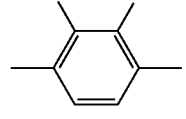
(A-6)

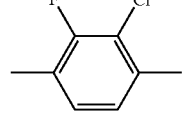
(A-7)

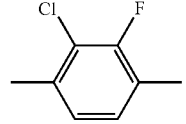
(A-8)

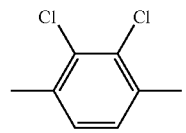
(A-9)

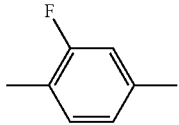
(A-10)

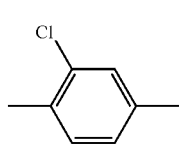
(A-11)

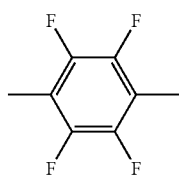
(A-12)

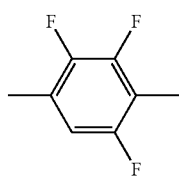
(A-13)

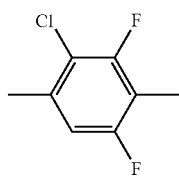
(A-14)

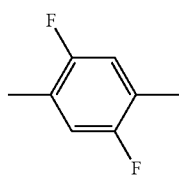
(A-15)

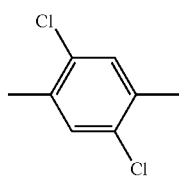
(A-16)

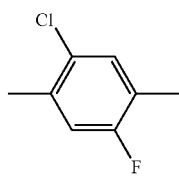
(A-17)

In the formula (1), $Z^1$ and $Z^2$ each represent a single bond or an alkylene having 1 to 4 carbon atoms. In the alkylene, at least one —$CH_2$— may be substituted by —O— or —COO— and at least one —$(CH_2)_2$— may be substituted by —CH=CH— or —C≡C—. In those groups, at least one hydrogen may be substituted by a halogen.

Preferred examples of $Z^1$ or $Z^2$ include a single bond, —$(CH_2)_2$—, —CH=CH—, —CF=CF—, —C≡C—, —COO—, —OCO—, —$CF_2O$—, —$OCF_2$—, —$CH_2O$—, —$OCH_2$—, —$(CH_2)_4$—, —$(CH_2)_2CF_2O$—, —$(CH_2)_2OCF_2$—, —$CF_2O(CH_2)_2$—, —$OCF_2$ $(CH_2)_2$—, —CH=CH—$(CH_2)_2$—, and —$(CH_2)_2$—CH=CH—. More preferred examples thereof include a single bond, —$(CH_2)_2$—, —CH=CH—, —COO—, —OCO—, —$CF_2O$—, —$OCF_2$—, —$CH_2O$—, and —$OCH_2$—. Still more preferred examples thereof include a single bond, —$(CH_2)_2$—, —$CH_2O$—, and —$OCH_2$—.

a and b each independently represent 0, 1, 2, 3, or 4, the sum of a and b is 4 or less, and when a or b represents 2 or more, any two rings $A^1$, any two rings $A^2$, any two $Z^1$'s, or any two $Z^2$'s may be identical to or different from each other. A preferred combination of a and b is (a=3, b=0), (a=2, b=1), (a=1, b=1), (a=2, b=0), or (a=1, b=0).

1-2. Physical Properties of Compound (1)

In the compound (1), through appropriate selection of a combination of $R^1$, $R^2$, the ring $A^1$, the ring $A^2$, $Z^1$, $Z^2$, a, and b, the physical properties, such as a clearing point, optical anisotropy, and dielectric anisotropy, can be arbitrarily adjusted. There is no significant difference in physical properties of the compound, and hence the compound (1) may contain an isotope, such as $^2H$ (deuterium) and $^{13}C$, in an amount larger than the amount of a natural existence ratio. The main effects of the kinds of $R^1$ and the like on the physical properties of the compound (1) are described below.

When $R^1$ or $R^2$ represents a straight chain, the temperature range of a liquid crystal phase is wide, and the viscosity is small. When $R^1$ or $R^2$ represents a branched chain, the compatibility with other liquid crystal compounds is satisfactory. A compound in which $R^1$ or $R^2$ is optically active is useful as a chiral dopant. Through addition of the compound to the composition, a reverse twisted domain generated in a liquid crystal display device can be prevented. A compound in which none of $R^1$ and $R^2$ is optically active is useful as a component of the composition. When $R^1$ or $R^2$ represents an alkenyl, a preferred configuration thereof depends on the position of a double bond. An alkenyl compound having a preferred configuration has a small viscosity, a high maximum temperature, and a wide temperature range of a liquid crystal phase. When $R^1$ or $R^2$ represents an alkoxy, the maximum temperature is high.

When both the ring $A^1$ and the ring $A^2$ is 1,4-cyclohexylene, the clearing point is high, and the viscosity is small. When at least one of the ring $A^1$ or the ring $A^2$ represents 1,4-phenylene or 1,4-phenylene in which at least one hydrogen is substituted by a halogen, the optical anisotropy is relatively large, and the orientational order parameter is relatively large. When both the ring $A^1$ and the ring $A^2$ represent 1,4-phenylene, 1,4-phenylene in which at least one hydrogen is substituted by a halogen, or a combination thereof, the optical anisotropy is particularly large.

When at least one of the ring $A^1$ or the ring $A^2$ represents 2-fluoro-1,4-phenylene, 2-chloro-1,4-phenylene, 2,3-difluoro-1,4-phenylene, 2,3-dichloro-1,4-phenylene, 2-chloro-3-fluoro-1, 4-phenylene, or tetrahydropyran-2, 5-diyl, the negative dielectric anisotropy is particularly large.

When at least one of $Z^1$ or $Z^2$ represents a single bond, —$CH_2CH_2$—, —CH=CH—, —$CF_2O$—, or —$OCF_2$—, the viscosity is small. When at least one of $Z^1$ or $Z^2$ represents —CH=CH—, —$CH_2O$—, or —$OCH_2$—, the temperature range of a liquid crystal phase is wide, and the elastic constant (K) is large. When at least one of Z or $Z^2$ represents a single bond, —CH=CH—, —C≡C—, —COO—, —OCO—, or —CF=CF—, the clearing point is high. When at least one of Z or $Z^2$ represents —CH=CH—, —C≡C—, or —CF=CF—, the optical anisotropy is large. When at least one of $Z^1$ or $Z^2$ represents —$CH_2O$— or —$OCH_2$—, the negative dielectric anisotropy is large. When both $Z^1$ and $Z^2$ represent a single bond, —$CH_2CH_2$—, —$CH_2O$—, or —$OCH_2$—, the chemical stability is high. When at least one of $Z^1$ or $Z^2$ represents —$(CH_2)_2$—, —CH=CH—, —COO—, —OCO—, —$CF_2O$—

—OCF$_2$—, —CH$_2$O—, or —OCH$_2$—, the compatibility with other liquid crystal compounds is satisfactory.

The compound (1) has at least one tetrafluoro cyclohexadiene structure in a structure thereof. The compound (1) has large dielectric anisotropy due to the effect of the structure.

1-3. Preferred Compound

Preferred examples of the compound (1) include the compounds (1-1) to (1-5) described in Item 5.

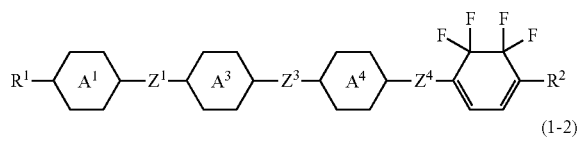
(1-1)

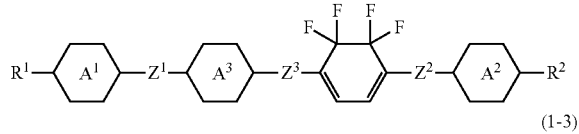
(1-2)

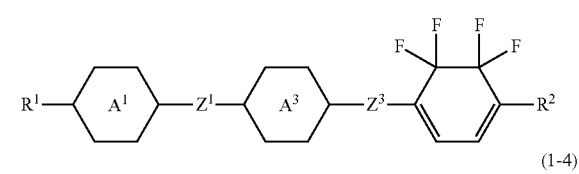
(1-3)

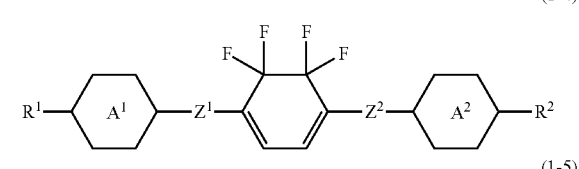
(1-4)

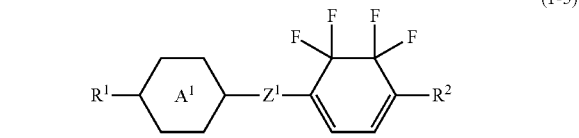
(1-5)

In the formulae (1-1) to (1-5):

R$^1$ and R$^2$ independently represent an alkyl having 1 to 10 carbon atoms, an alkenyl having 2 to 10 carbon atoms, or an alkoxy having 1 to 9 carbon atoms;

a ring A$^1$, a ring A$^2$, a ring A$^3$, and a ring A$^4$ independently represent 1,4-cyclohexylene, 1,4-cyclohexenylene, 1,4-phenylene, 1,4-phenylene in which at least one hydrogen is substituted by a halogen, tetrahydropyran-2,5-diyl, or 5,5,6,6-tetrafluoro-1,3-cyclohexadiene-1,4-diyl; and Z$^1$ and Z$^2$ independently represent a single bond, —(CH$_2$)$_2$—, —CH=CH—, —COO—, —OCO—, —CH$_2$O—, —OCH$_2$—, —CF$_2$O—, or —OCF$_2$—.

Preferred examples of the compound (1) include the compounds (1-6) to (1-10) described in Item 7.

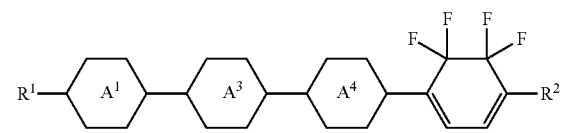
(1-6)

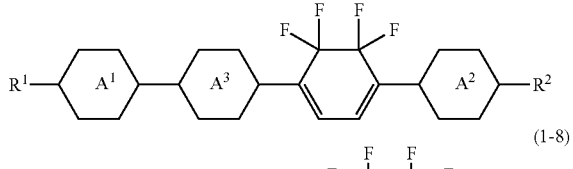
(1-7)

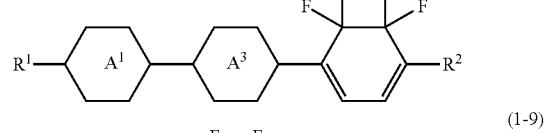
(1-8)

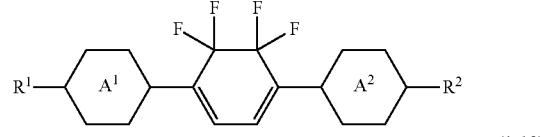
(1-9)

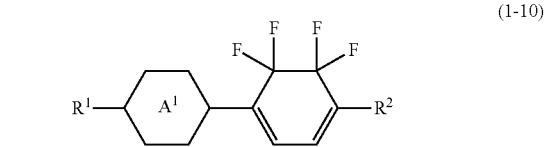
(1-10)

In the formulae (1-6) to (1-10): R$^1$ and R$^2$ independently represent hydrogen, fluorine, an alkyl having 1 to 10 carbon atoms, an alkenyl having 2 to 10 carbon atoms, an alkoxy having 1 to 9 carbon atoms, or an alkenyloxy having 2 to 9 carbon atoms, and in the groups, at least one hydrogen may be substituted by fluorine; and a ring A, a ring A$^2$, a ring A$^3$, and a ring A$^4$ independently represent 1,4-cyclohexylene, 1,4-cyclohexenylene, 1,4-phenylene, 1,4-phenylene in which at least one hydrogen is substituted by a halogen, tetrahydropyran-2,5-diyl, or 5,5,6,6-tetrafluoro-1,3-cyclohexadiene-1,4-diyl.

More preferred examples of the compound (1) include compounds represented by the following formulae (1-11) to (1-55).

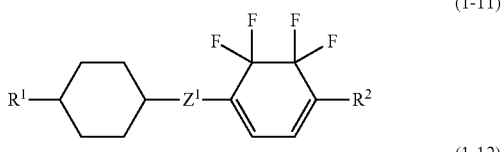
(1-11)

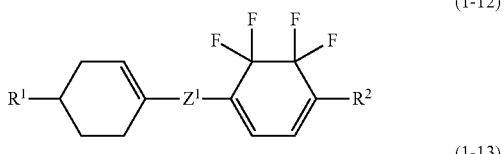
(1-12)

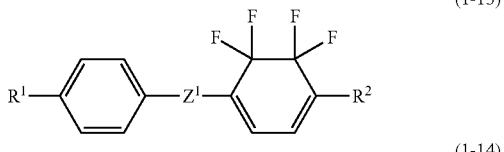
(1-13)

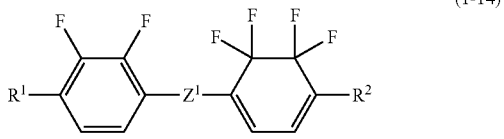
(1-14)

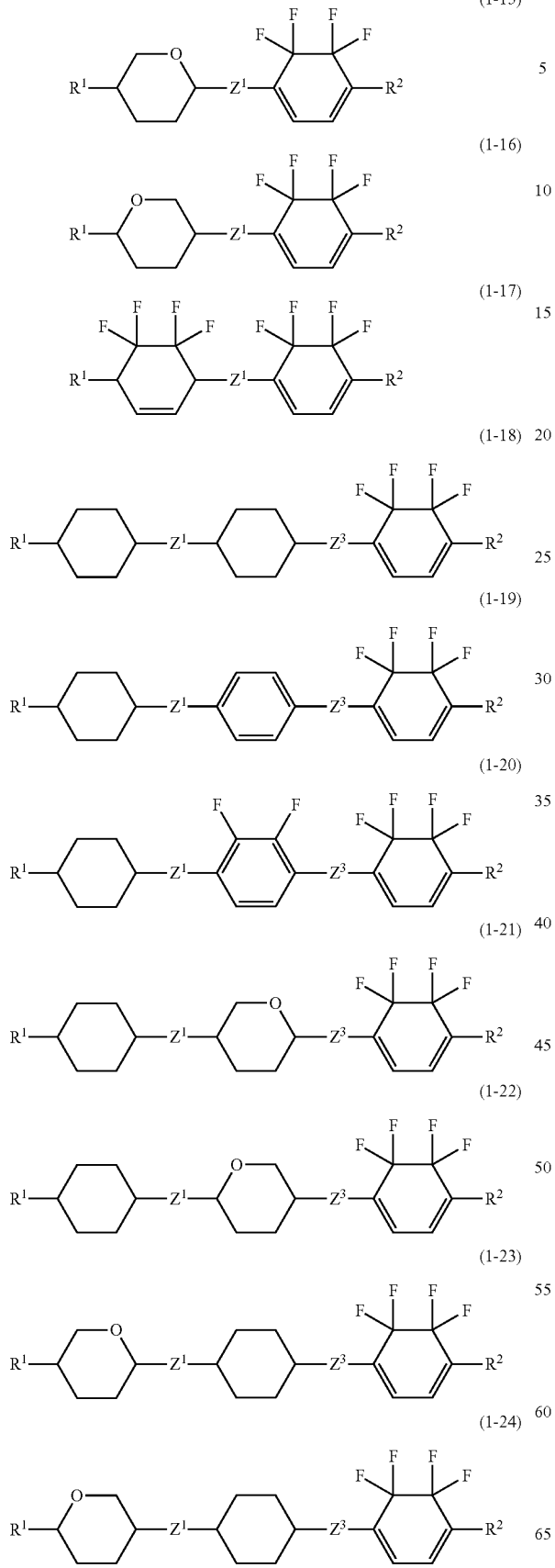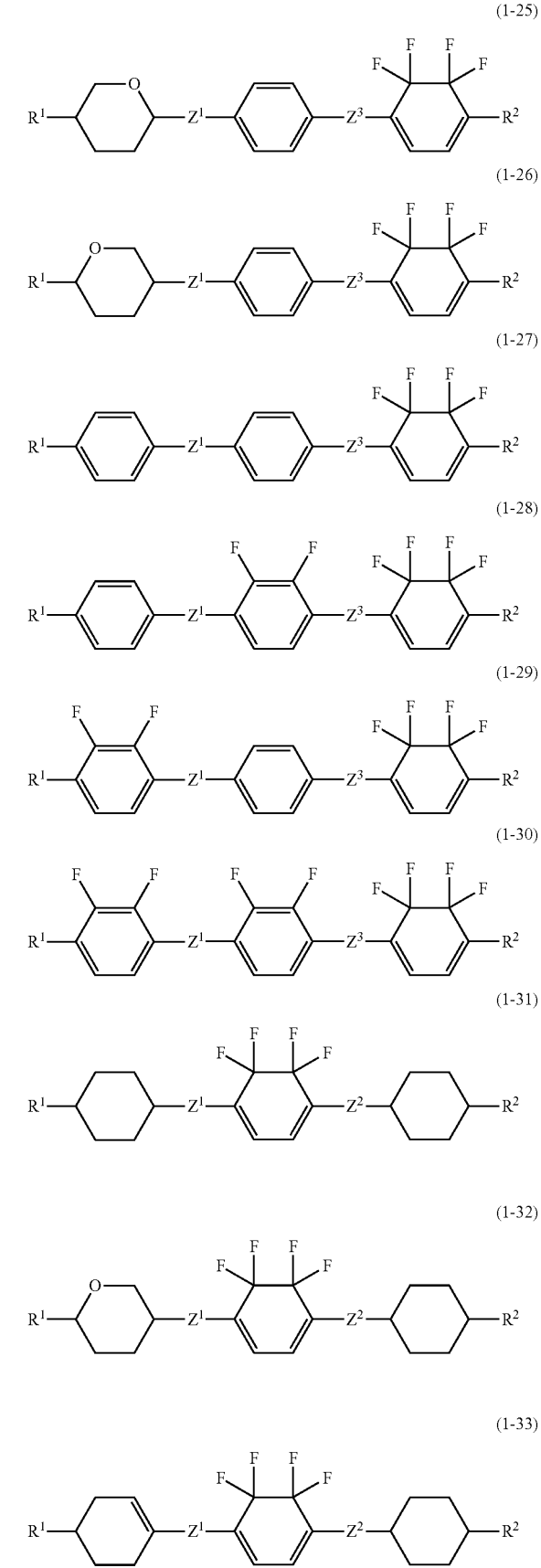

(1-34) 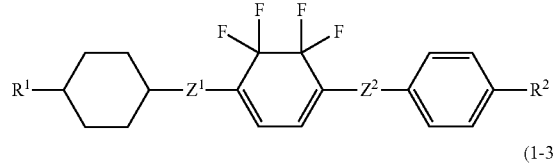
(1-35) 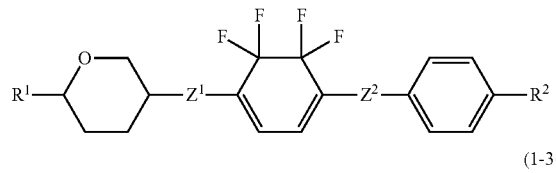
(1-36) 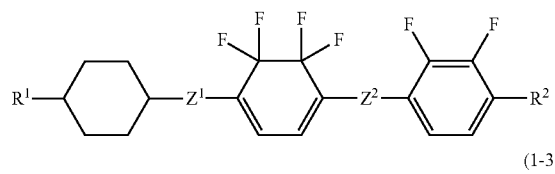
(1-37) 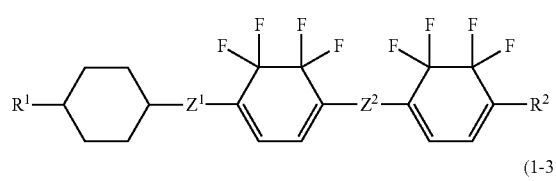
(1-38) 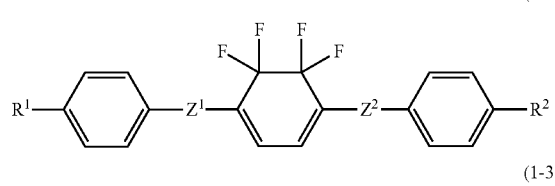
(1-39) 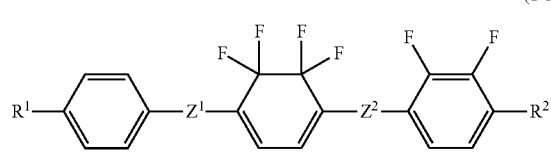
(1-40) 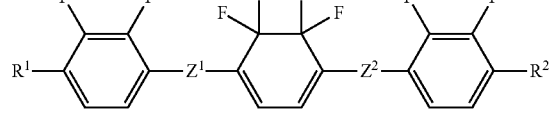
(1-41) 
(1-42) 
(1-43) 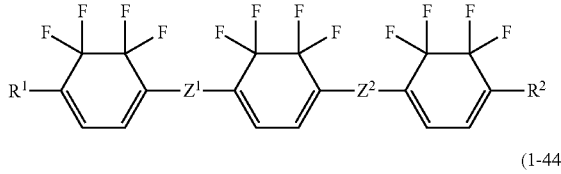
(1-44) 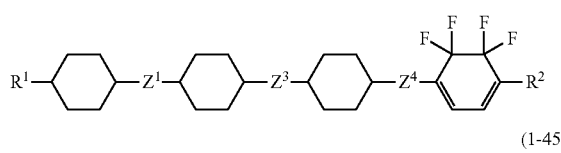
(1-45) 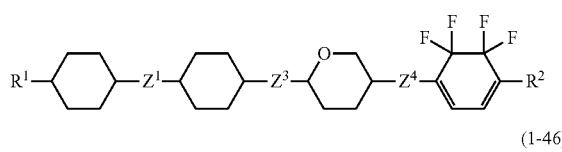
(1-46) 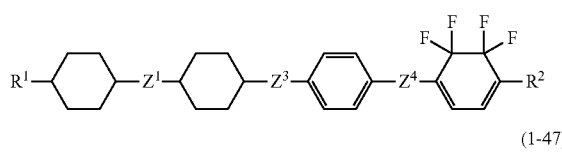
(1-47) 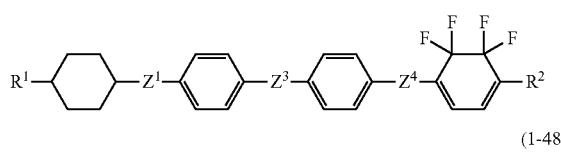
(1-48) 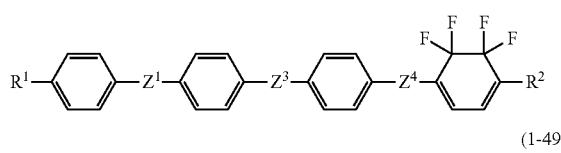
(1-49) 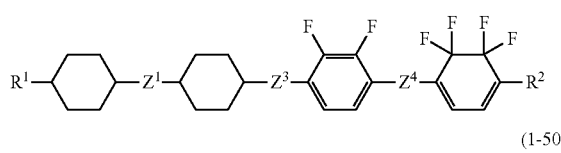
(1-50) 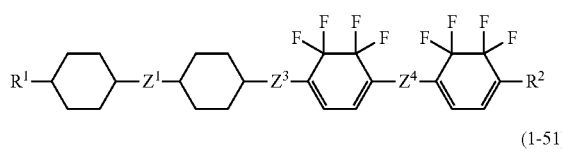
(1-51) 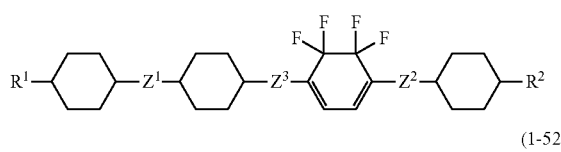
(1-52) 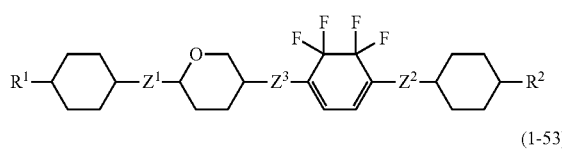
(1-53) 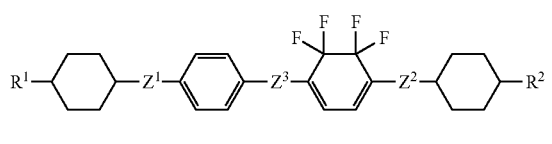

-continued

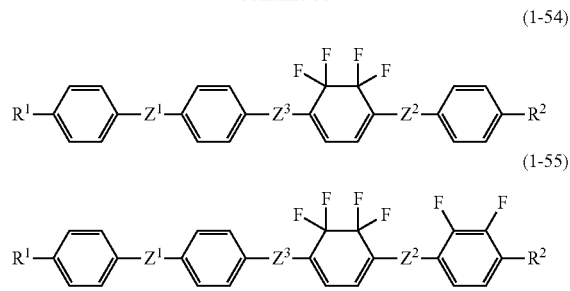

In the formulae (1-11) to (1-55):

$R^1$ and $R^2$ each independently represent an alkyl having 1 to 10 carbon atoms, an alkenyl having 2 to 10 carbon atoms, or an alkoxy having 1 to 9 carbon atoms; and $Z^1$, $Z^2$, $Z^3$, and $Z^4$ each independently represent a single bond, —$(CH_2)_2$—, —CH=CH—, —COO—, —OCO—, —$CH_2O$—, —$OCH_2$—, —$CF_2O$—, or —$OCF_2$—.

1-4. Synthesis of Compound (1)

A synthesis method for the compound (1) is described. The compound (1) can be synthesized by appropriately combining methods of synthetic organic chemistry. A method of introducing an intended terminal group, ring, or linking group into a starting material is described in books, such as Organic Syntheses, John Wiley & Sons, Inc., Organic Reactions, John Wiley & Sons, Inc., and Comprehensive Organic Synthesis, Pergamon Press, and New Experimental Chemistry Lecture (Maruzen Co., Ltd.).

1-4-1. Generation of Linking Group

An example of a method of generating a linking group in the compound (1) is as described in the following scheme. In the scheme, $MSG^1$ (or $MSG^2$) is a monovalent organic group having at least one ring. Monovalent organic groups represented by a plurality of $MSG^1$'s (or $MSG^2$'s) may be identical to or different from each other. Compounds (1A) to (1G) correspond to the compound (1) or an intermediate product of the compound (1).

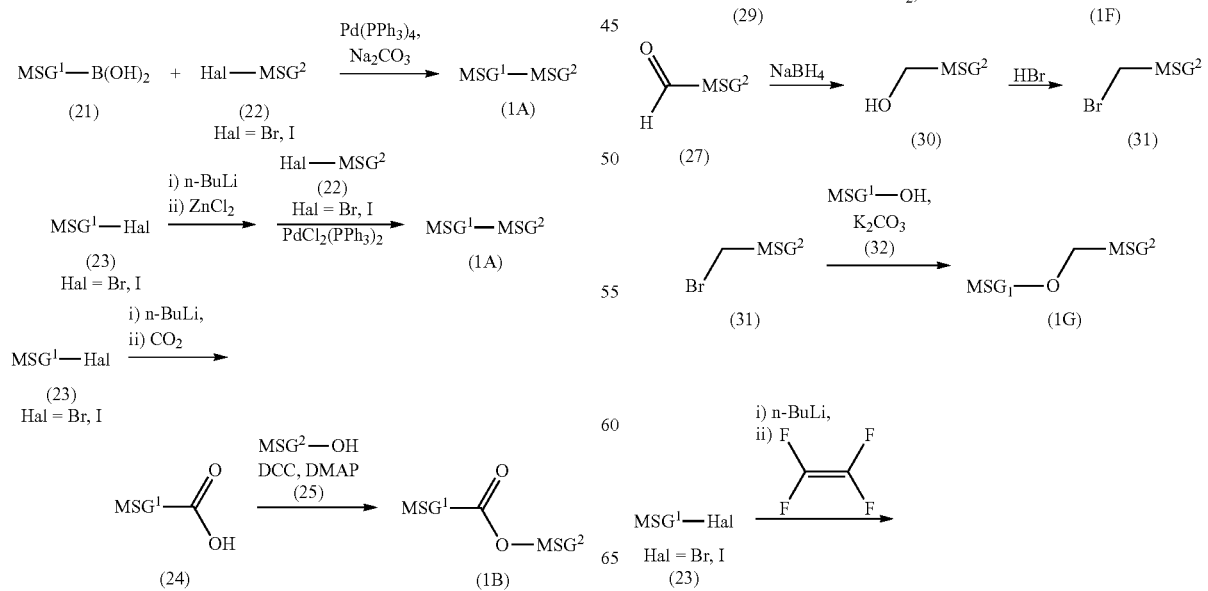

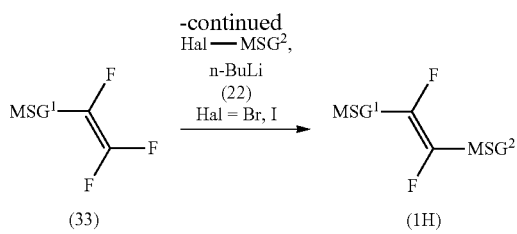

(I) Generation of Single Bond

Arylboronic acid (21) and a compound (22) are allowed to react with each other in the presence of a carbonate and a tetrakis(triphenylphosphine)palladium catalyst to synthesize a compound (1A). The compound (1A) is also synthesized by allowing n-butyllithium and then zinc chloride to react with a compound (23) and allowing the compound (22) to react with the resultant in the presence of a dichlorobis(triphenylphosphine)palladium catalyst.

(II) Generation of —COO— and —OCO— n-Butyllithium and then carbon dioxide are allowed to react with the compound (23) to provide a carboxylic acid (24). The carboxylic acid (24) and a phenol (25) derived from the compound (21) are dehydrated in the presence of 1,3-dicyclohexylcarbodiimide (DCC) and 4-dimethylaminopyridine (DMAP) to synthesize a compound (1B) having —COO—. Through this method, a compound having —OCO— is also synthesized.

(III) Generation of —CF$_2$O— and —OCF$_2$—

The compound (1B) is thionated with a Lawesson's reagent to provide a compound (26). The compound (26) is fluorinated with a hydrogen fluoride pyridine complex and N-bromosuccinimide (NBS) to synthesize a compound (IC) having —CF$_2$O—. See M. Kuroboshi et al., Chem. Lett., 1992, 827. The compound (IC) is also synthesized by fluorinating the compound (26) with (diethylamino)sulfur trifluoride (DAST). See W. H. Bunnelle et al., J. Org. Chem. 1990, 55, 768. Through this method, a compound having —OCF$_2$— is also synthesized.

(IV) Generation of —CH=CH—

The compound (22) is allowed to react with n-butyllithium and then N,N-dimethylformamide (DMF) to provide an aldehyde (27). A phosphorus ylide generated by allowing a phosphonium salt (28) and potassium tert-butoxide to react with each other is allowed to react with the aldehyde (27) to synthesize a compound (1D). A cis form is generated depending on reaction conditions, and hence the cis form is isomerized into a trans form by a known method as necessary.

(V) Generation of —CH$_2$CH$_2$—

The compound (1D) is hydrogenated in the presence of a palladium carbon catalyst to synthesize a compound (1E).

(VI) Generation of —C≡C—

2-Methyl-3-butyn-2-ol is allowed to react with the compound (23) in the presence of dichloropalladium and copper iodide, and then the resultant is deprotected under basic conditions to provide a compound (29). The compound (29) and the compound (22) are allowed to react with each other in the presence of a catalyst of dichlorobis(triphenylphosphine)palladium and a copper halide to synthesize a compound (1F).

(VII) Generation of —CH$_2$O— and —OCH$_2$—

The compound (27) is reduced with hydrogenated sodium borate to provide a compound (30). The compound (30) is brominated with hydrobromic acid to provide a compound (31). A compound (32) and the compound (31) are allowed to react with each other in the presence of potassium carbonate to synthesize a compound (1G). Through this method, a compound having —OCH$_2$— is also synthesized.

(VIII) Generation of —CF=CF—

After the compound (23) is treated with n-butyllithium, tetrafluoroethylene is allowed to react with the resultant compound (23) to provide a compound (33). After the compound (22) is treated with n-buthyllithium, the compound (22) is allowed to react with the compound (33) to synthesize a compound (1H).

1-4-2. Generation of Ring A$^1$ and Ring A$^2$

Regarding rings such as 1,4-cyclohexylene, 1,4-cyclohexenylene, 1,4-phenylene, 2-fluoro-1,4-phenylene, 2,3-difluoro-1,4-phenylene, tetrahydropyran-2,5-diyl, and 1,3-dioxane-2,5-diyl, starting materials are commercially available or synthesis methods are well known.

1-4-3. Synthesis Example

An example of a method of synthesizing the compound (1) is as described below. In these compounds, the definitions of R$^1$, R$^2$, a ring A$^1$, a ring A$^2$, Z$^1$, Z$^2$, a, and b are the same as those in Item 1.

An example of the method of synthesizing the compound (1) is as described below. The compound (1) is obtained by allowing iodobenzene diacetate and then [bis(2-methoxyethyl)amino]sulfur trifluoride (hereinafter sometimes abbreviated as "Deoxo-fluor") to react with a compound (34) having a catechol skeleton synthesized by a known method.

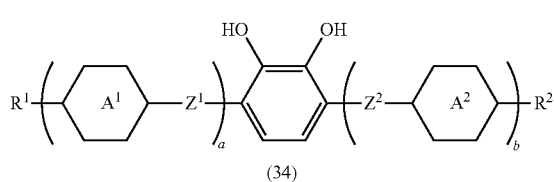

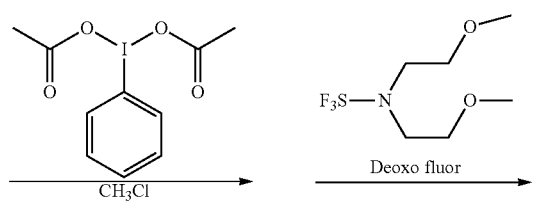

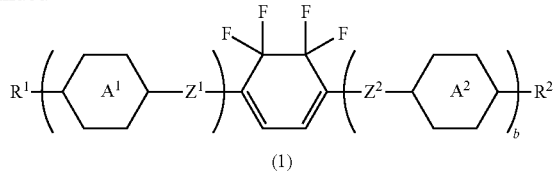

2. Composition (1)

A liquid crystal composition (1) of the present invention is described. The composition (1) contains at least one compound (1) as a component A. The composition (1) may contain two or more compounds (1). The component of the liquid crystal compound may be only the compound (1). It is preferred that the composition (1) contain at least one compound (1) within a range of from 1 wt % to 99 wt % from the viewpoint that excellent physical properties are exhibited. In a composition showing positive dielectric anisotropy, the preferred content of the compound (1) falls within a range of from 5 wt % to 60 wt %. In a composition showing negative dielectric anisotropy, the preferred content of the compound (1) is 30 wt % or less. The composition (1) may contain the compound (1) and various liquid crystal compounds not described in this description.

The preferred composition contains compounds selected from components B, C, D, and E described below. When the composition (1) is prepared, for example, components can also be selected in consideration of the dielectric anisotropy of the compound (1). A composition prepared by appropriately selecting components has a high maximum temperature of a nematic phase, a low minimum temperature of a nematic phase, a small viscosity, suitable optical anisotropy, large dielectric anisotropy, and a suitable elastic constant.

The component B corresponds to compounds (2) to (4). The component C corresponds to a compound (5). The component D corresponds to compounds (6) to (12). The component E corresponds to compounds (13) to (15). Those components are described in the stated order.

The component B is a compound having a halogen or a fluorine-containing group at a right end. Preferred examples of the component B may include compounds (2-1) to (2-16), compounds (3-1) to (3-113), and compounds (4-1) to (4-57).

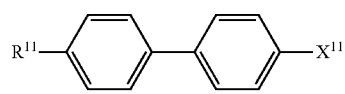 (2-1)

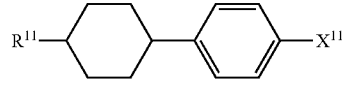 (2-2)

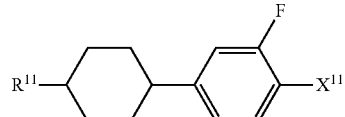 (2-3)

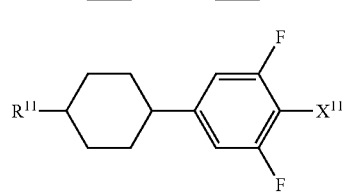 (2-4)

-continued

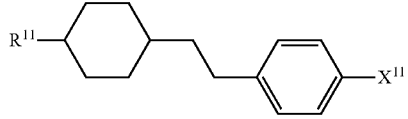 (2-5)

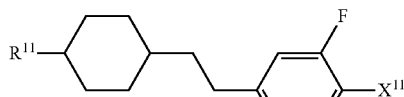 (2-6)

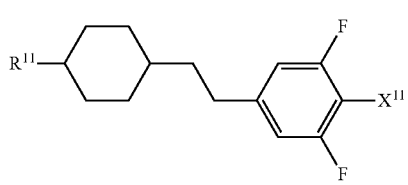 (2-7)

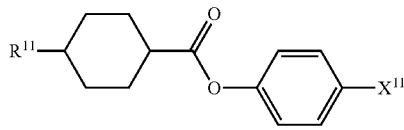 (2-8)

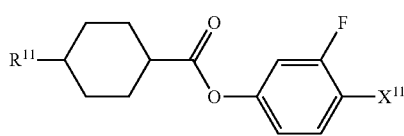 (2-9)

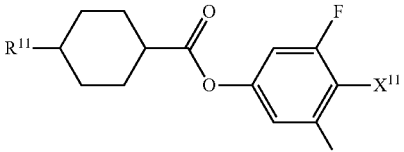 (2-10)

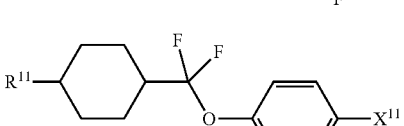 (2-11)

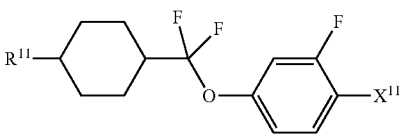 (2-12)

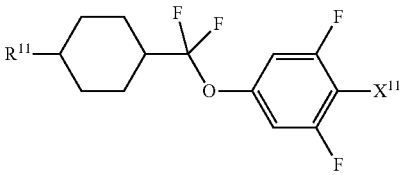 (2-13)

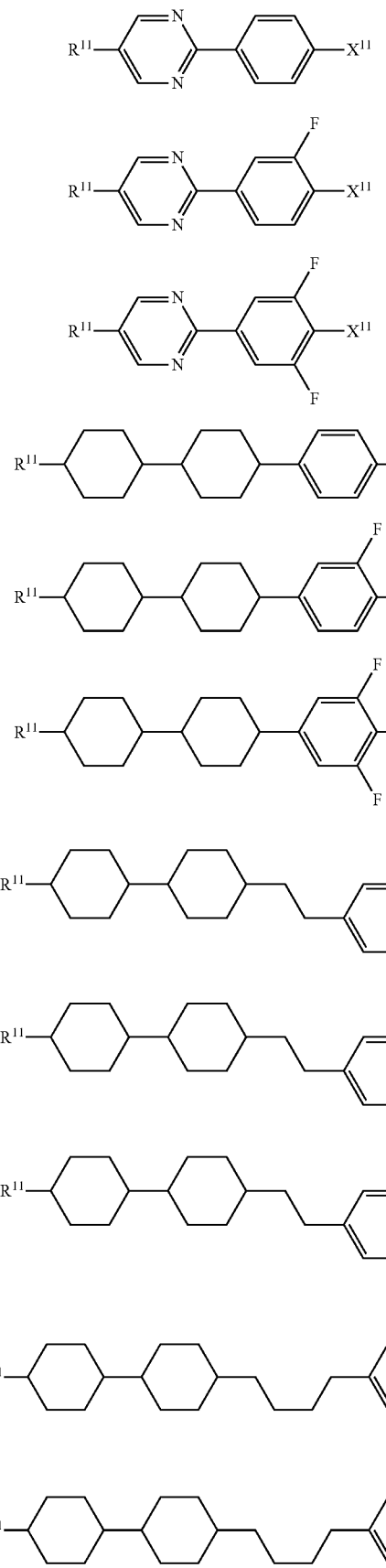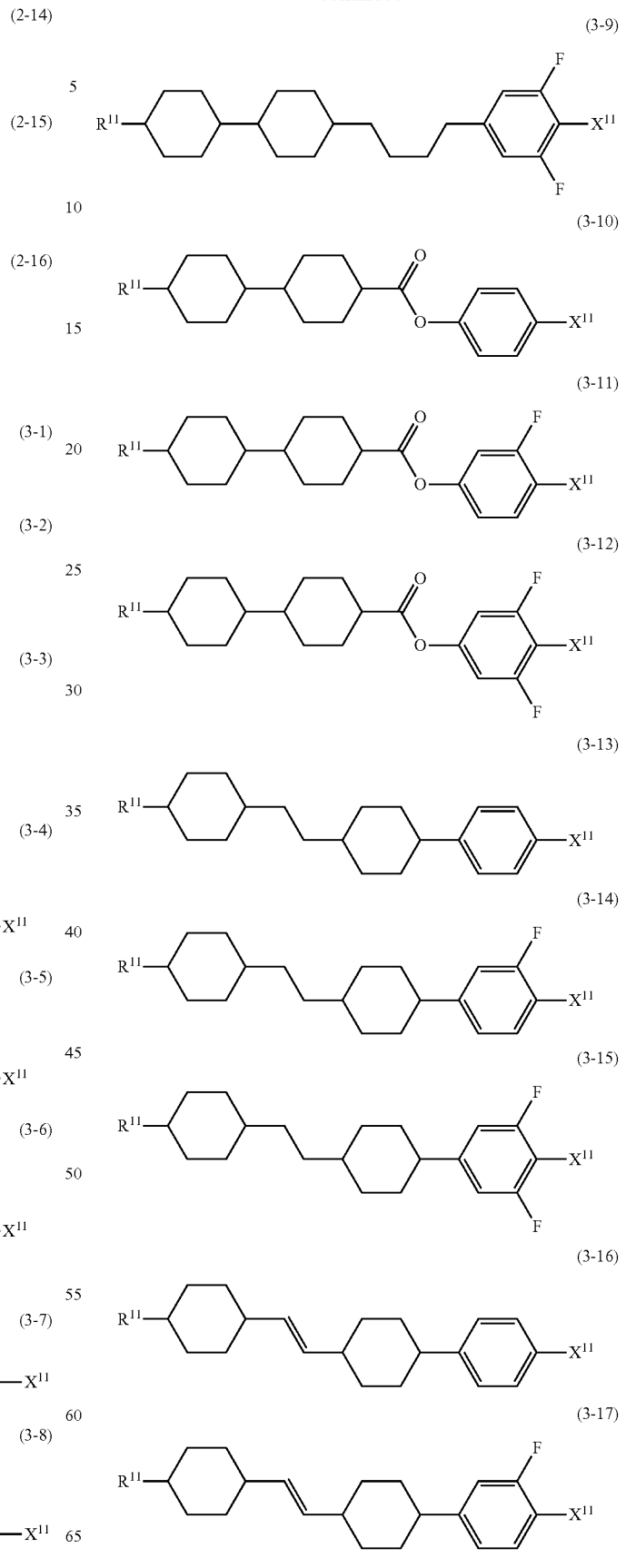

(3-18) 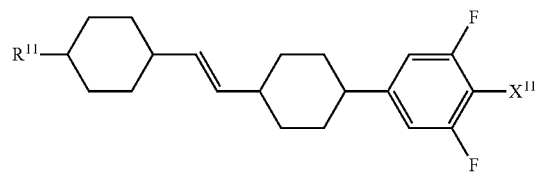
(3-19) 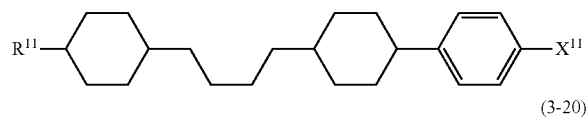
(3-20) 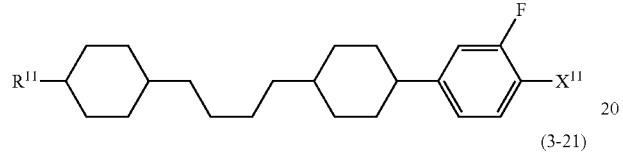
(3-21) 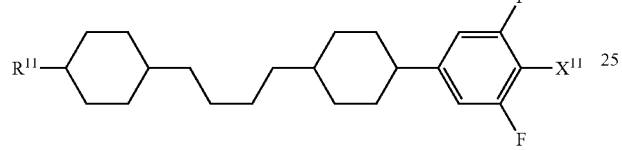
(3-22) 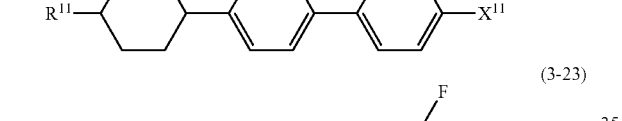
(3-23) 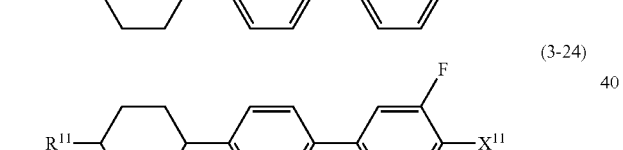
(3-24) 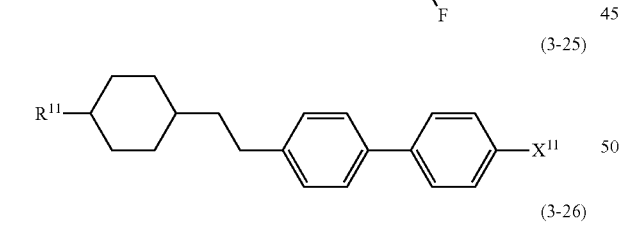
(3-25) 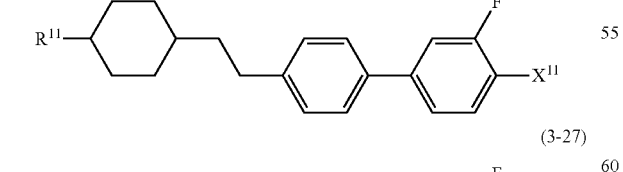
(3-26) 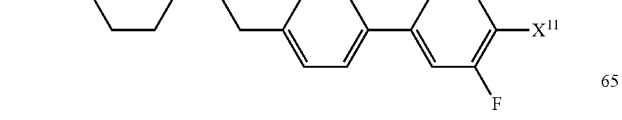
(3-27) 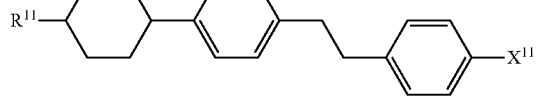
(3-28) 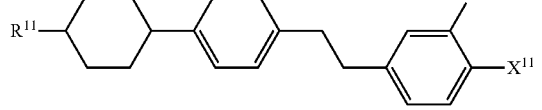
(3-29) 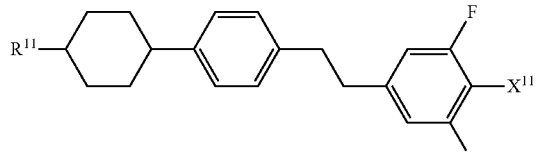
(3-30) 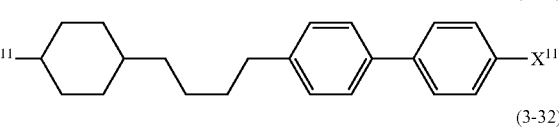
(3-31) 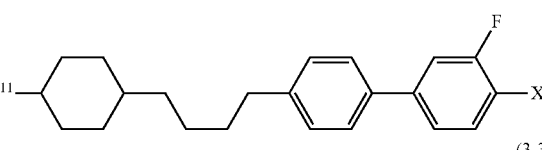
(3-32) 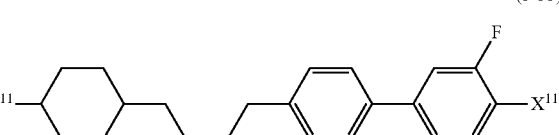
(3-33) 
(3-34) 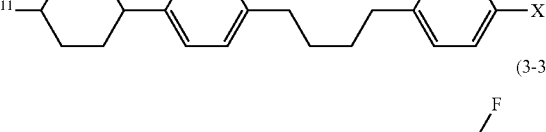
(3-35) 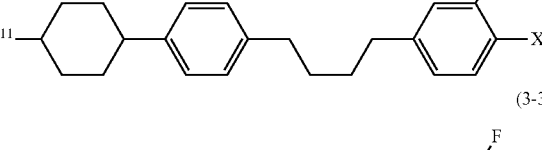
(3-36) 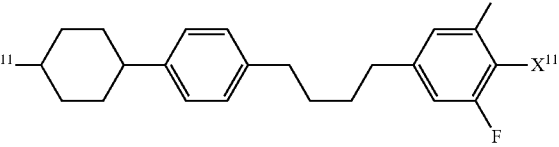
(3-37) 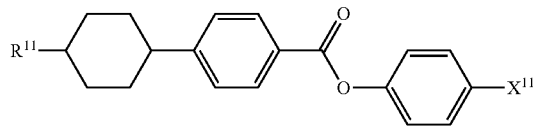

(3-38) 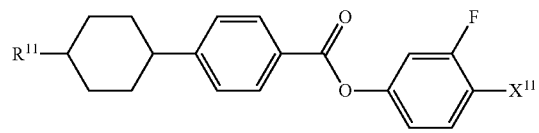
(3-39) 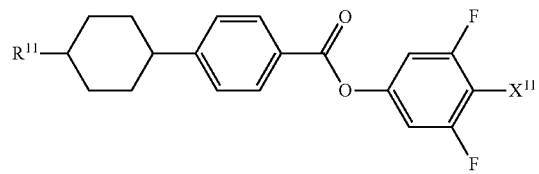
(3-40) 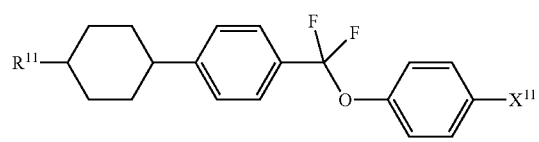
(3-41) 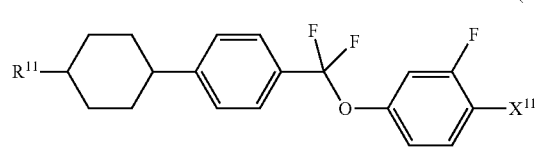
(3-42) 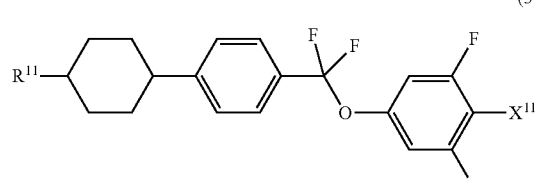
(3-43) 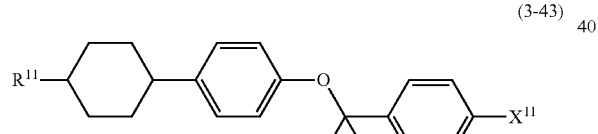
(3-44) 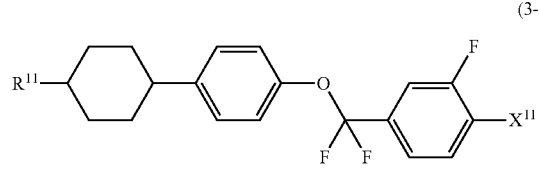
(3-45) 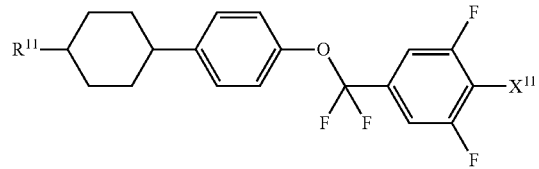
(3-46) 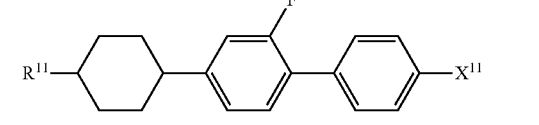
(3-47) 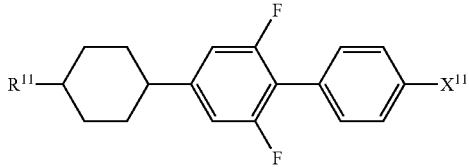
(3-48) 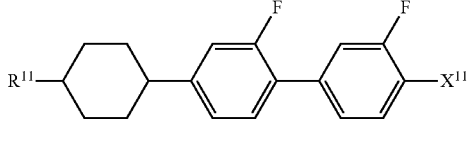
(3-49) 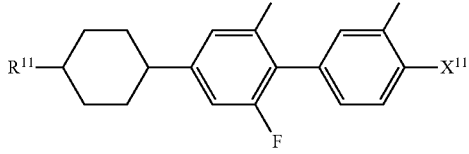
(3-50) 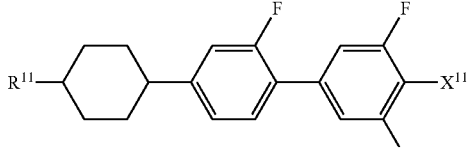
(3-51) 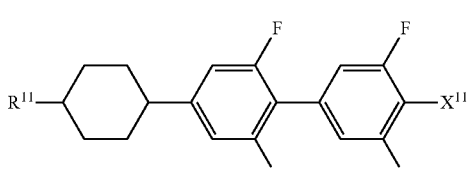
(3-52) 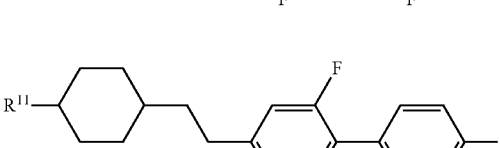
(3-53) 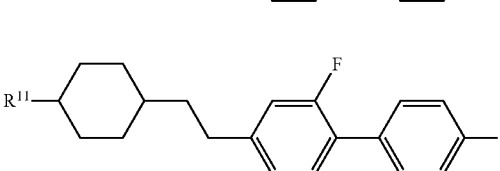
(3-54) 
(3-55) 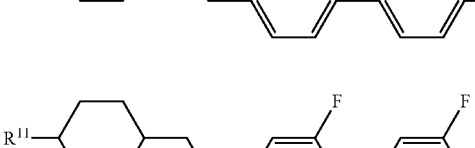

(3-56) 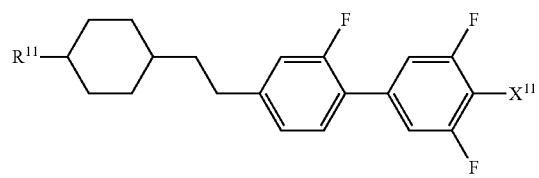
(3-57) 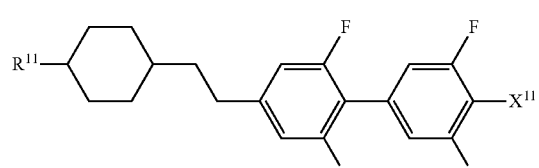
(3-58) 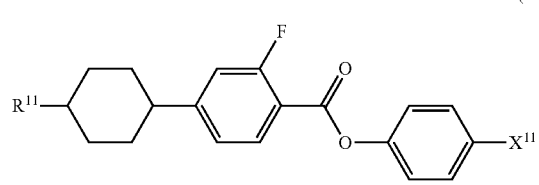
(3-59) 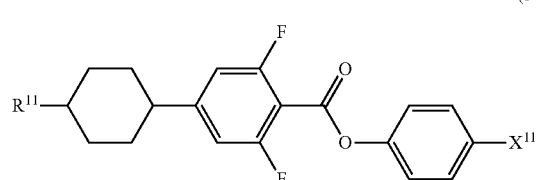
(3-60) 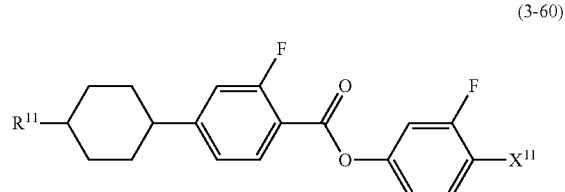
(3-61) 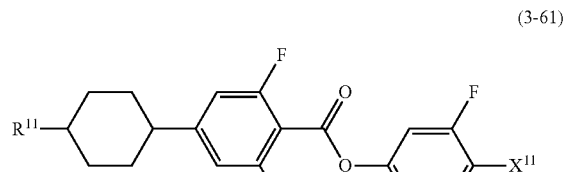
(3-62) 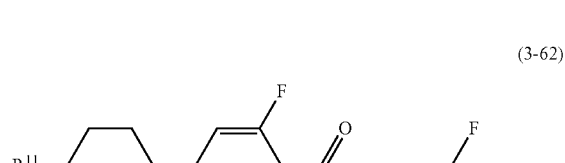
(3-63) 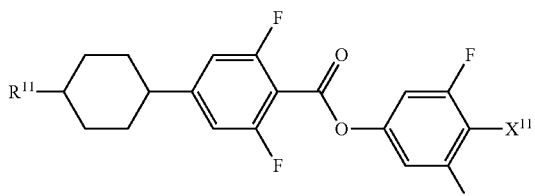
(3-64)
(3-65)
(3-66)
(3-67)
(3-68)
(3-69)
(3-70)
(3-71)
(3-72)

(3-73) 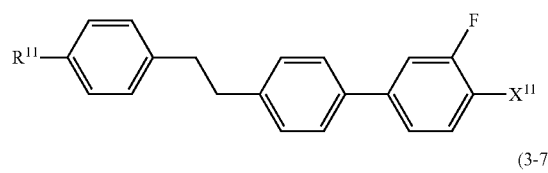
(3-74) 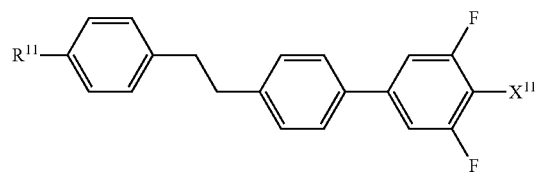
(3-75) 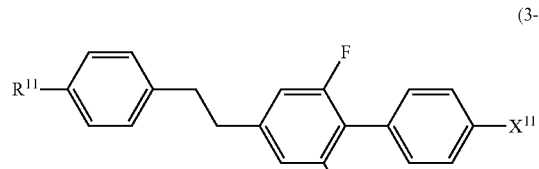
(3-76) 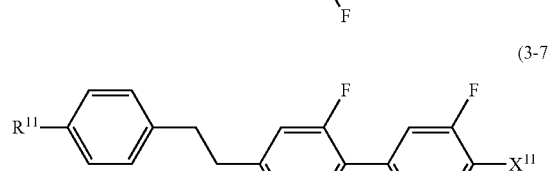
(3-77) 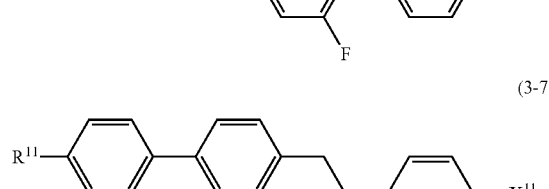
(3-78) 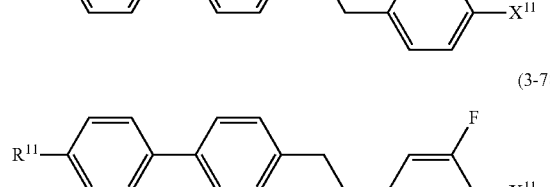
(3-79) 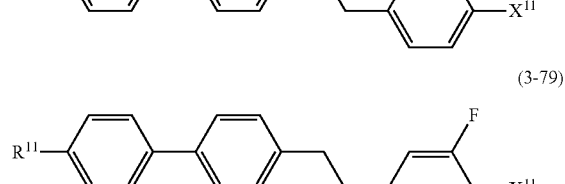
(3-80) 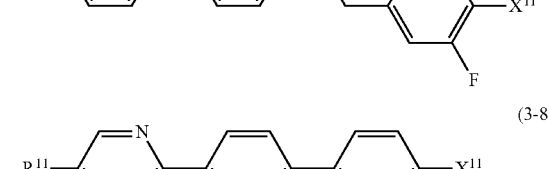
(3-81) 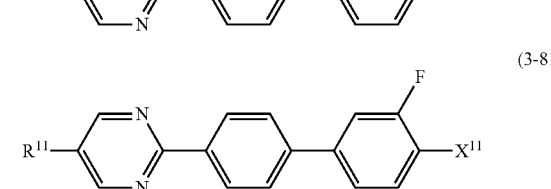
(3-82) 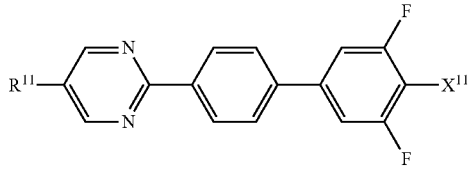
(3-83) 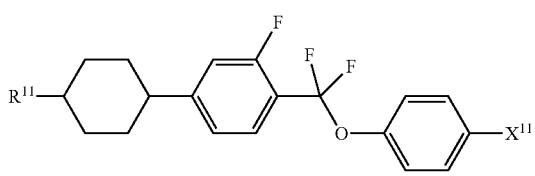
(3-84) 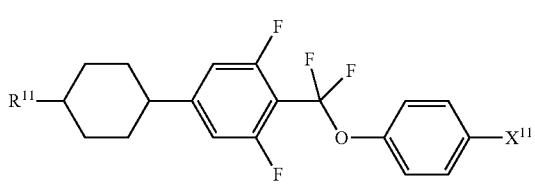
(3-85) 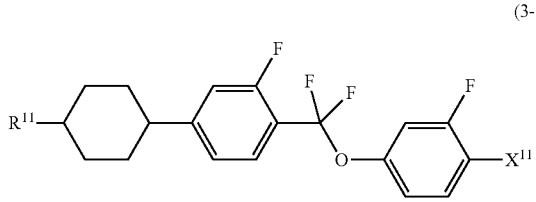
(3-86) 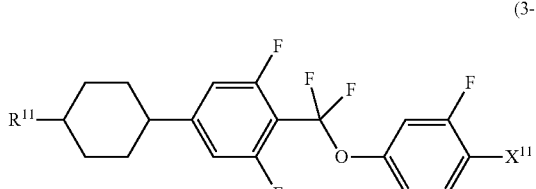
(3-87) 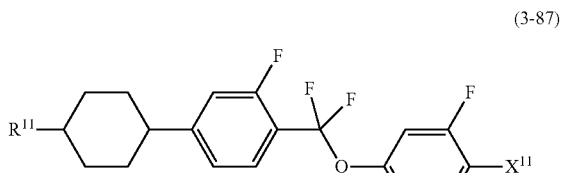
(3-88) 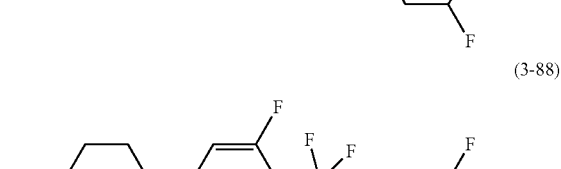
(3-89) 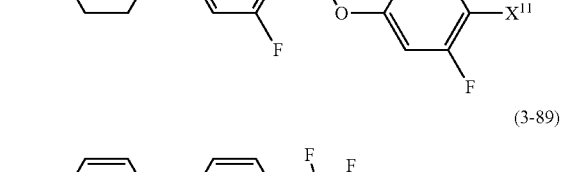

(3-90)
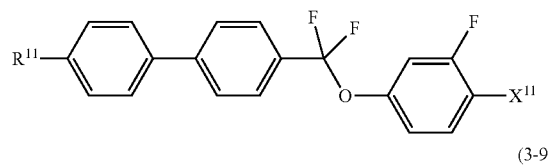
(3-91)
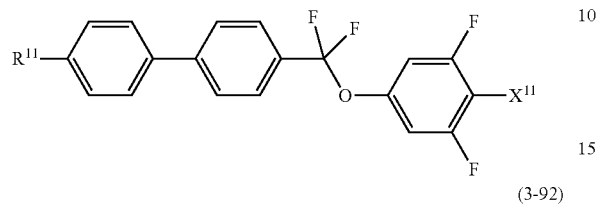
(3-92)
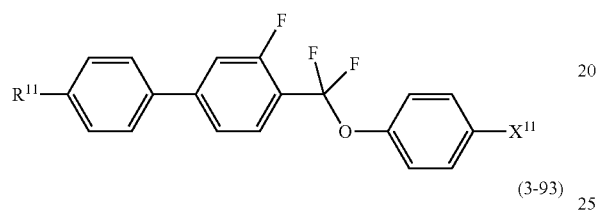
(3-93)
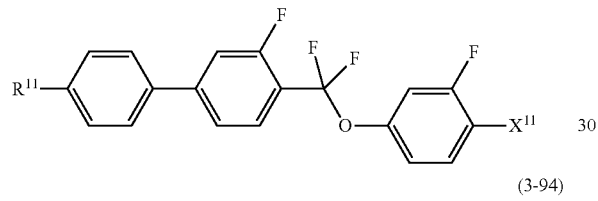
(3-94)
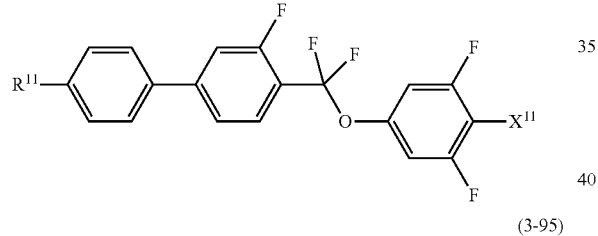
(3-95)
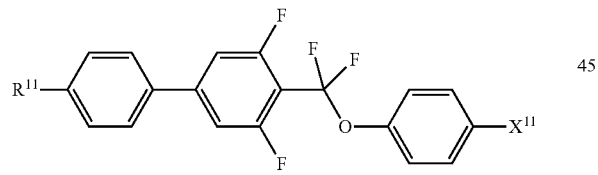
(3-96)
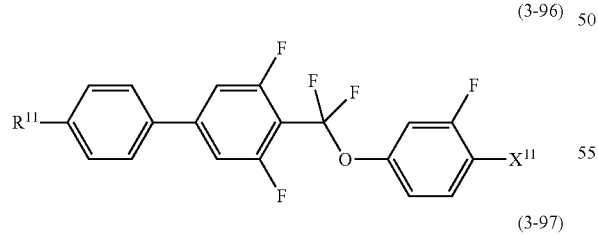
(3-97)
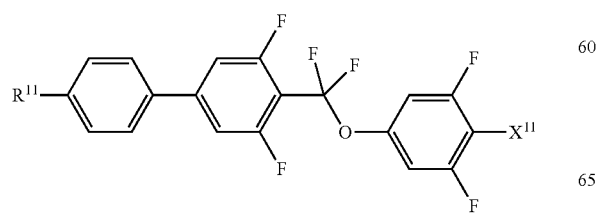
(3-98)
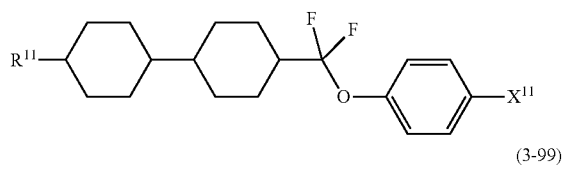
(3-99)
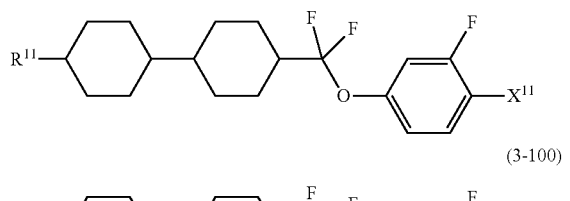
(3-100)
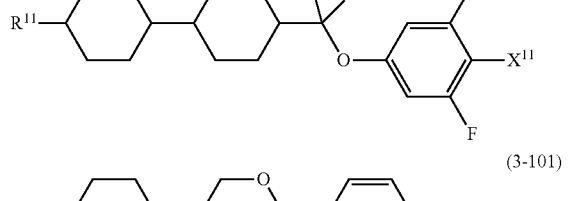
(3-101)
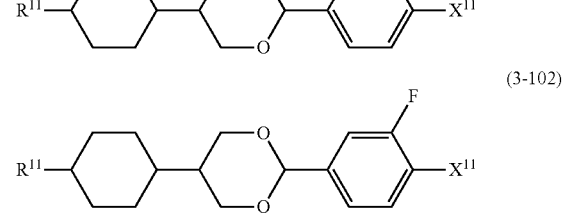
(3-102)
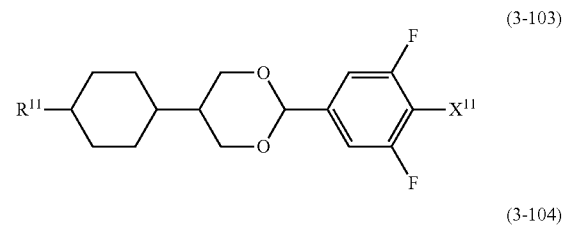
(3-103)
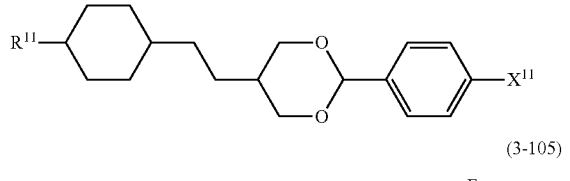
(3-104)
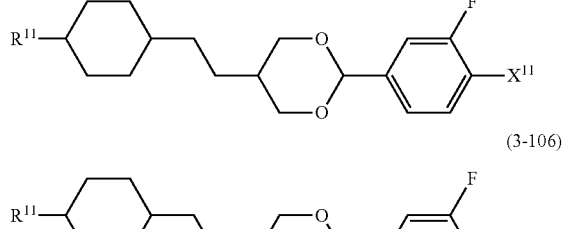
(3-105)
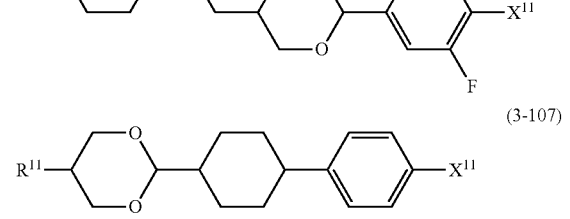
(3-106)
(3-107)

(3-108) 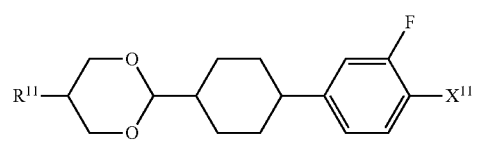
(3-109) 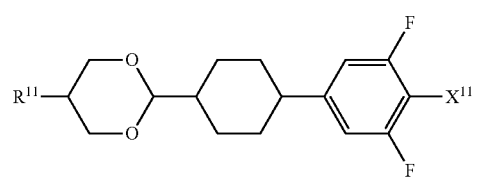
(3-110) 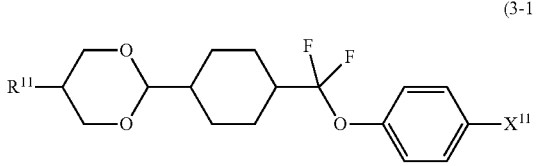
(3-111) 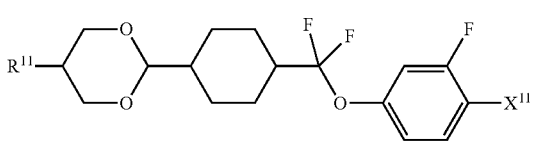
(3-112) 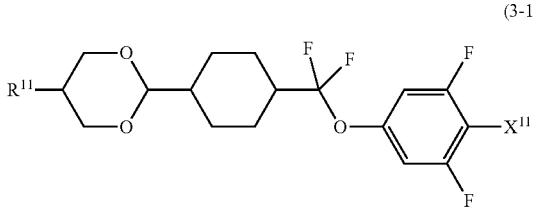
(3-113) 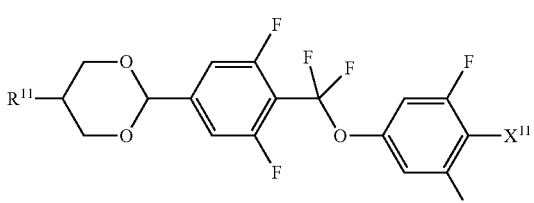
(4-1) 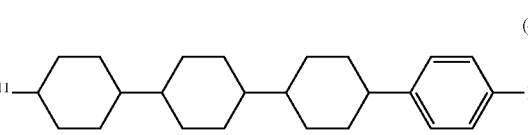
(4-2) 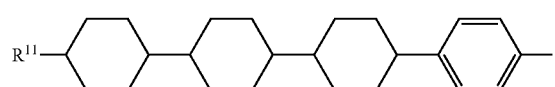
(4-3) 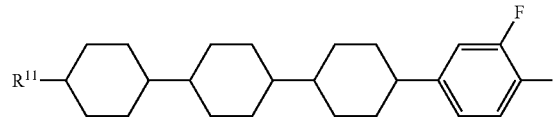
(4-4) 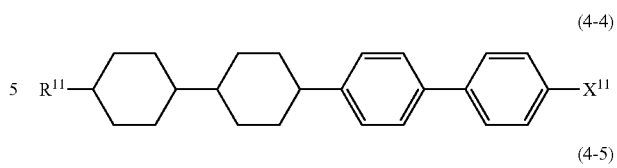
(4-5) 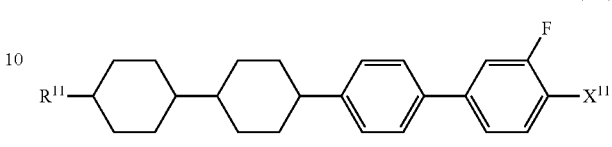
(4-6) 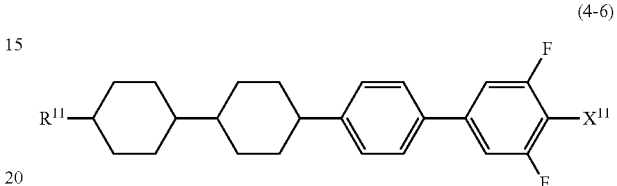
(4-7) 
(4-8) 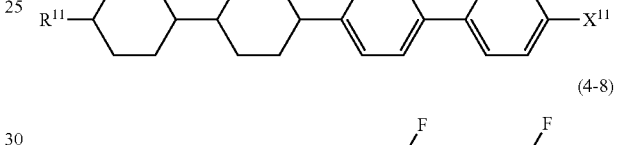
(4-9) 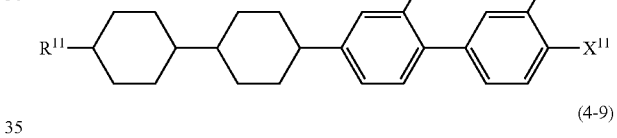
(4-10) 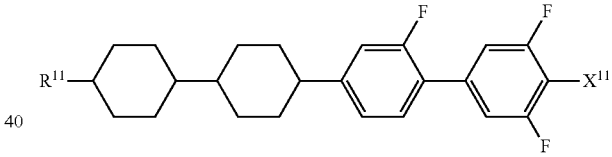
(4-11) 
(4-12) 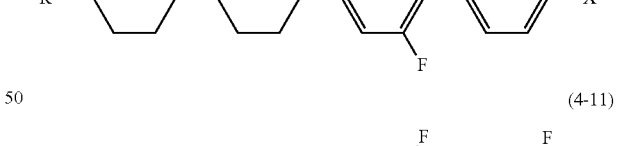
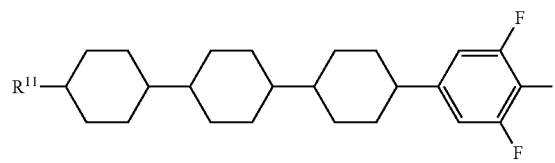
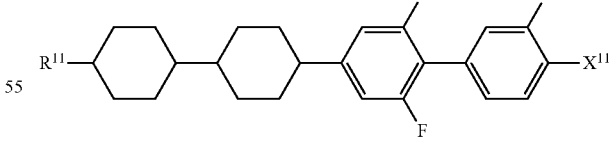

(4-13) 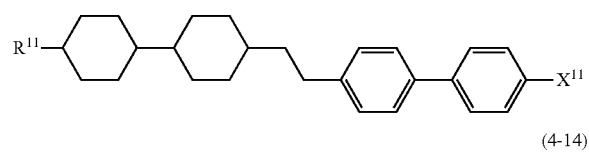
(4-14) 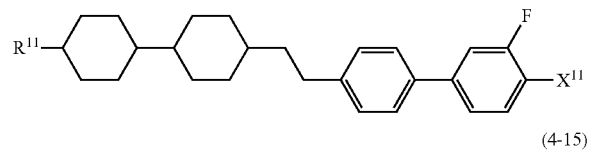
(4-15) 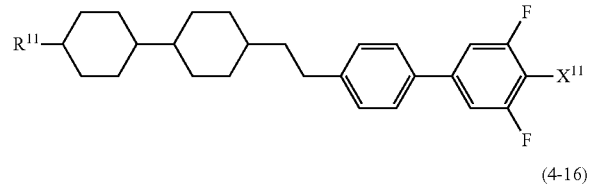
(4-16) 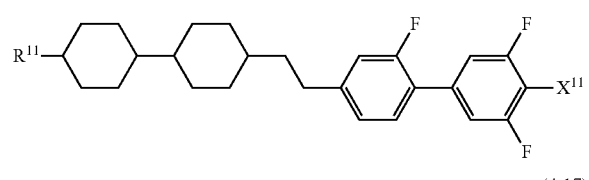
(4-17) 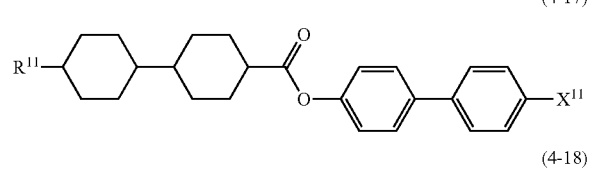
(4-18) 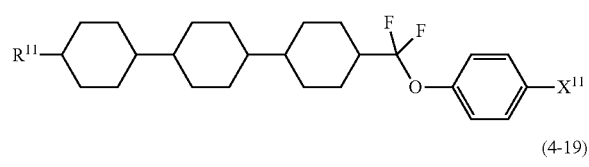
(4-19) 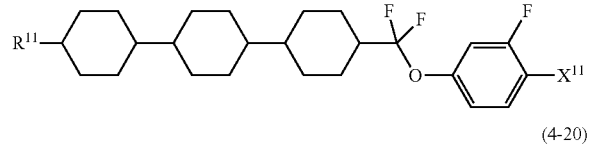
(4-20) 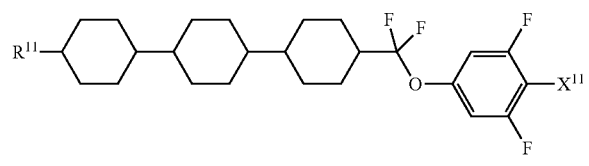
(4-21) 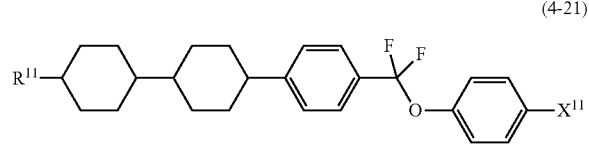
(4-22) 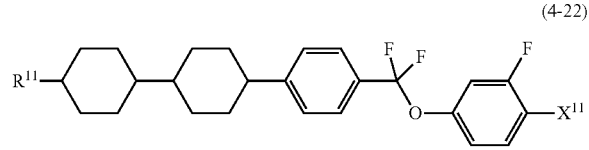
(4-23) 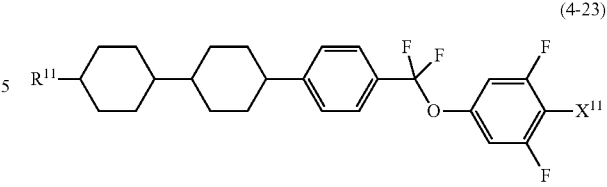
(4-24) 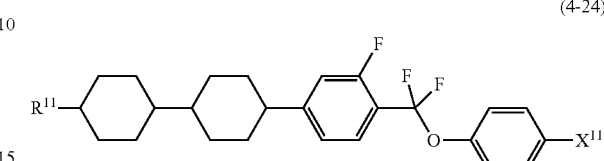
(4-25) 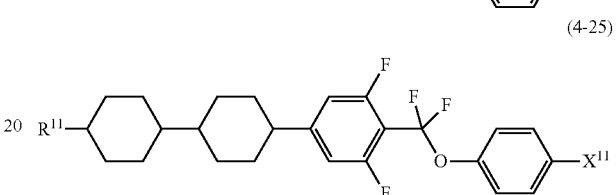
(4-26) 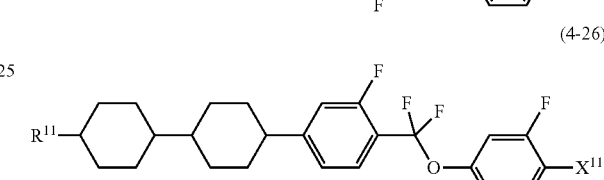
(4-27) 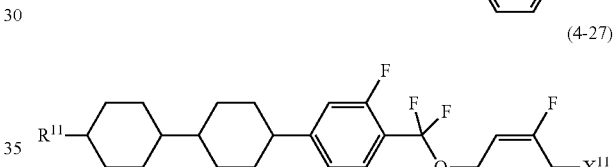
(4-28) 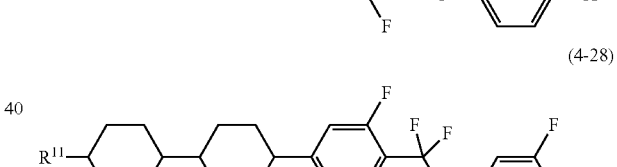
(4-29) 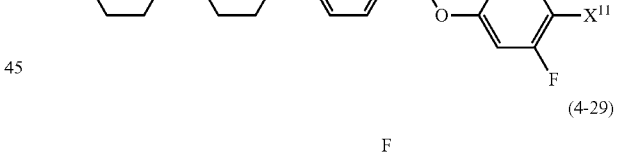
(4-30) 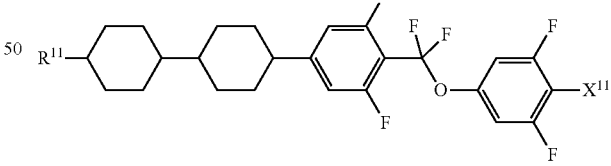
(4-31) 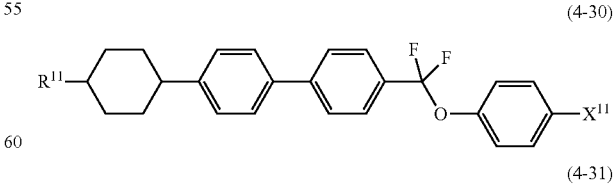

(4-32) 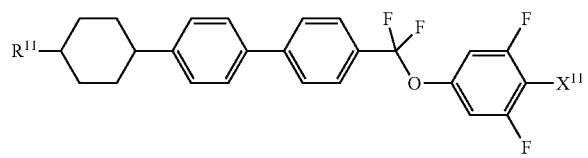
(4-33) 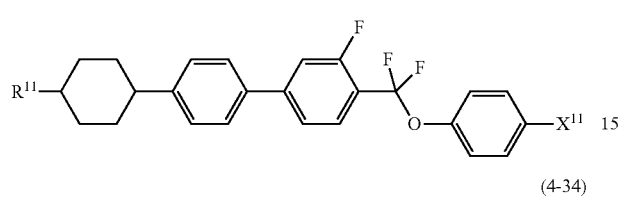
(4-34)
(4-35)
(4-36) 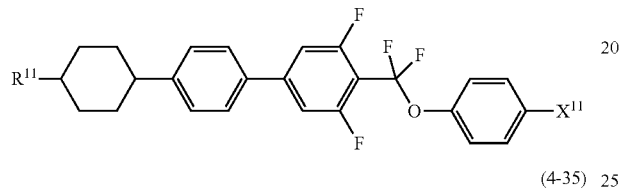
(4-37) 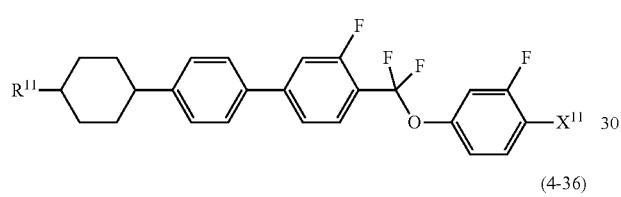
(4-38) 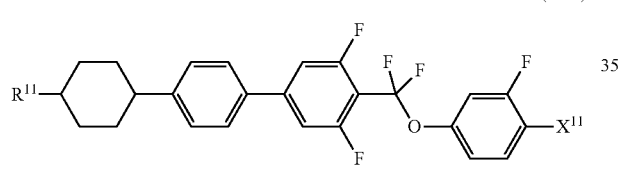
(4-39) 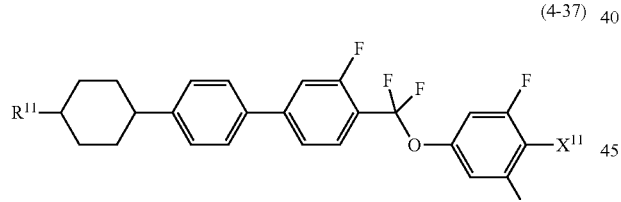
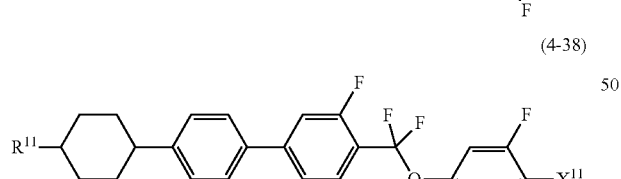
(4-40) 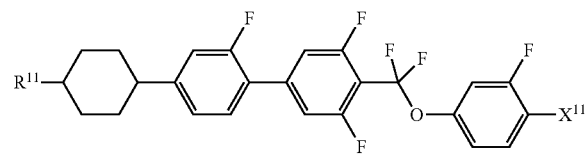
(4-41) 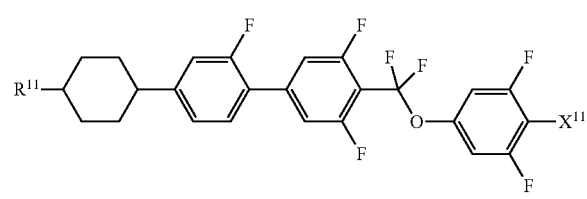
(4-42)
(4-43)
(4-44) 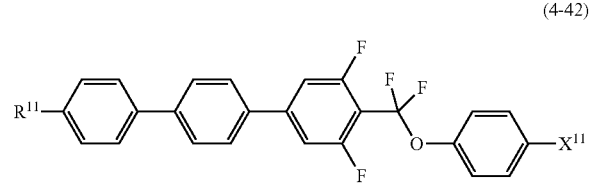
(4-45) 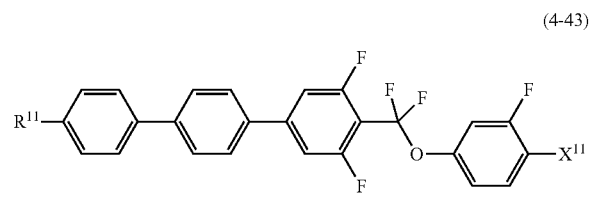
(4-46) 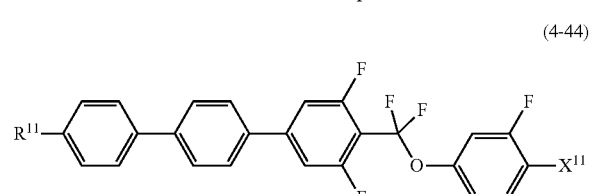
(4-47) 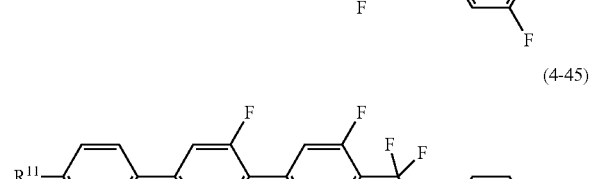
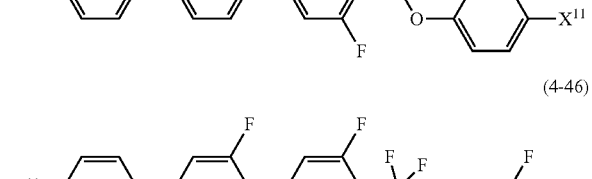
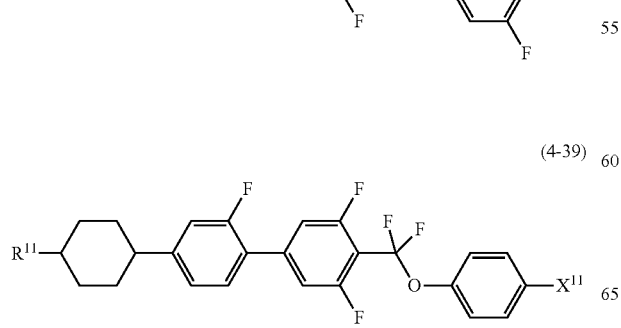
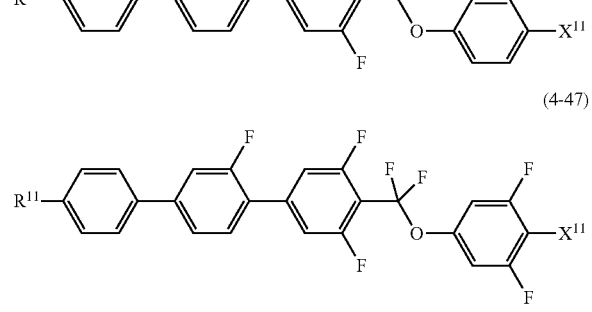

(4-48)
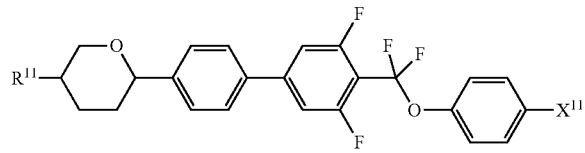

(4-49)
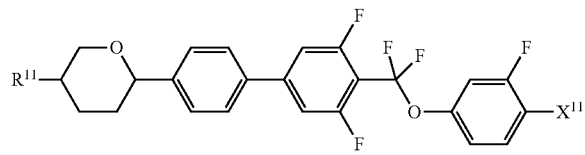

(4-50)
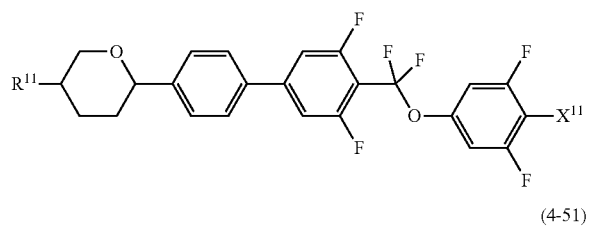

(4-51)

(4-52)
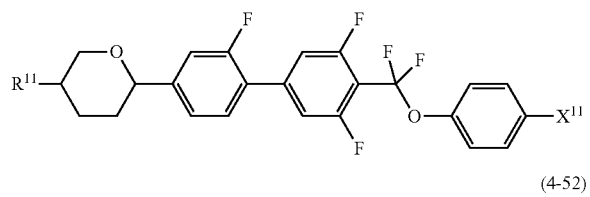

(4-53)
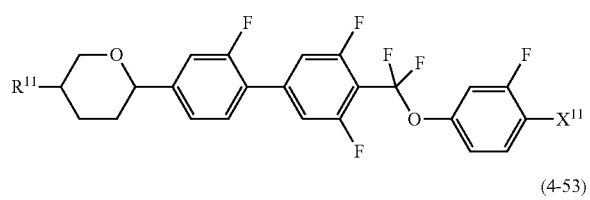

(4-54)
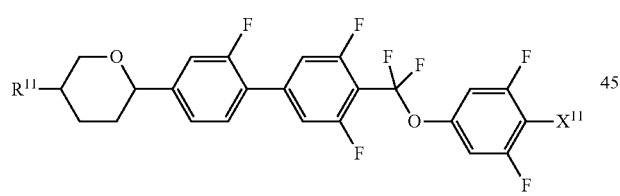

(4-55)
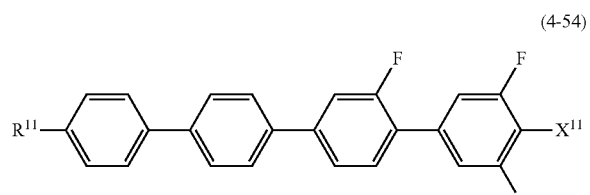

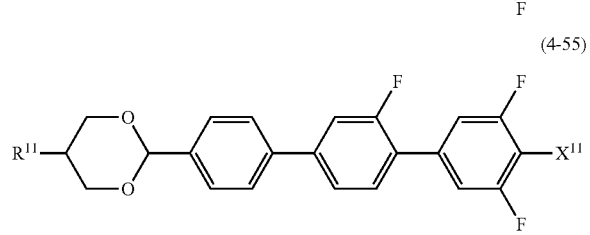

(4-56)
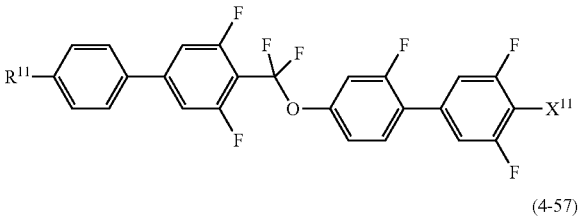

(4-57)
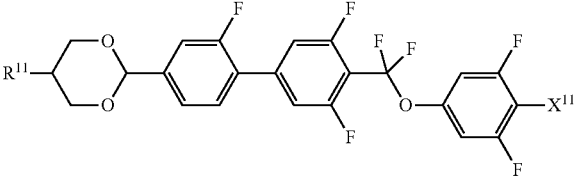

In those compounds (component B), the definitions of $R^{11}$ and $X^{11}$ are the same as those of the formulae (2) to (4) described in Item 13.

The component B shows positive dielectric anisotropy and is significantly excellent in stability to heat, light, and the like. Therefore, the component B is used in the case of preparing a composition for a TFT mode or a PSA mode. The content of the component B suitably falls within a range of from 1 wt % to 99 wt %, preferably a range of from 10 wt % to 97 wt %, more preferably a range of from 40 wt % to 95 wt % with respect to the total weight of the composition. The viscosity of the composition can be adjusted by further adding the compounds (12) to (14) (component E).

The component C is a compound (5) having —C≡N or —C≡C—C≡N as a right terminal group. Preferred examples of the component C may include compounds (5-1) to (5-64).

(5-1)
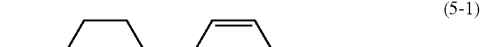

(5-2)

(5-3)

(5-4)
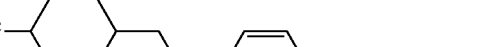

(5-5)
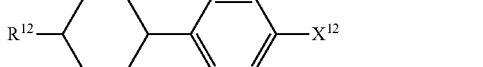

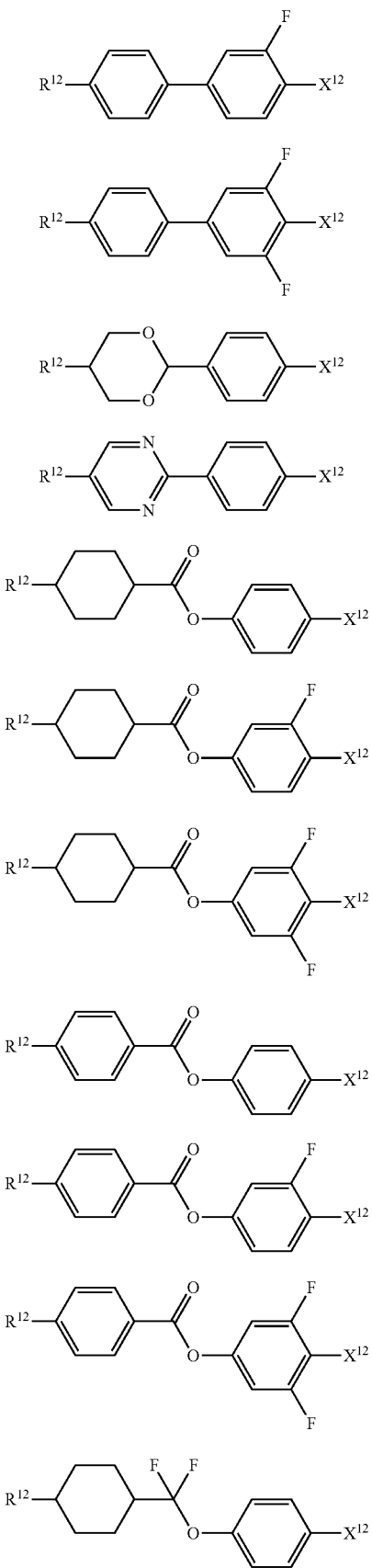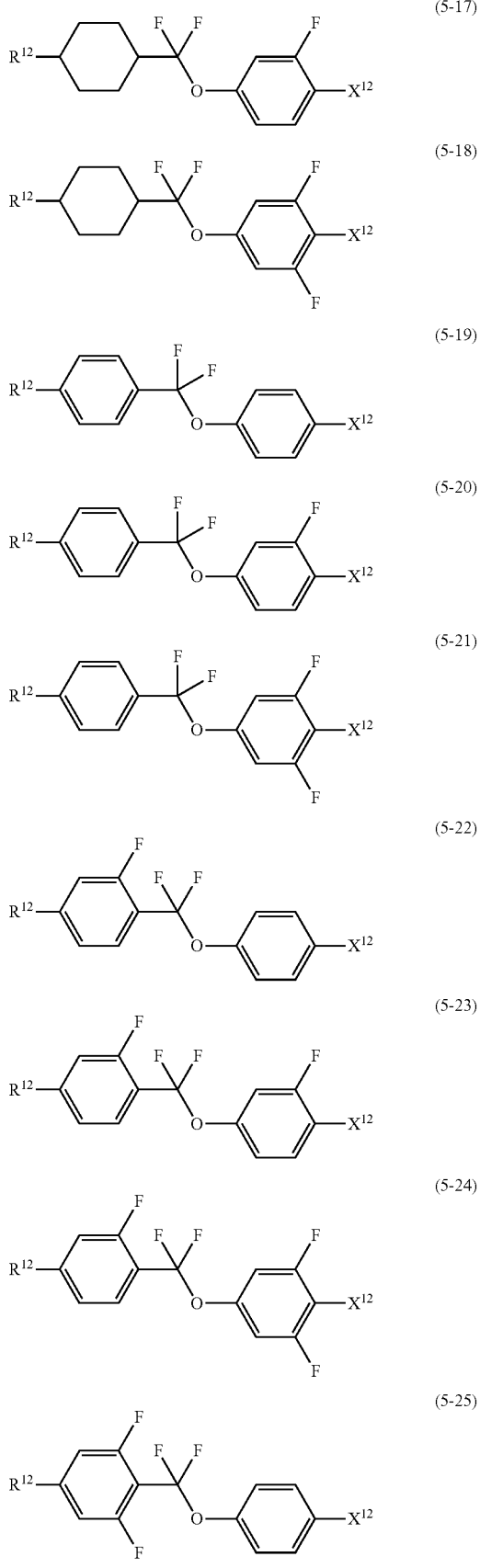

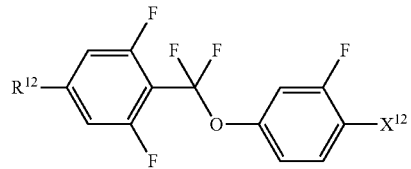 (5-26)
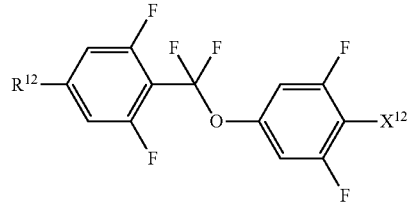 (5-27)
 (5-28)
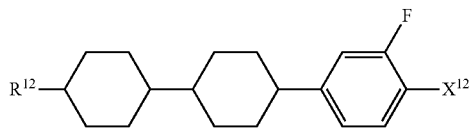 (5-29)
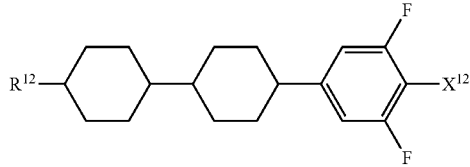 (5-30)
 (5-31)
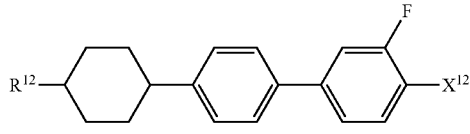 (5-32)
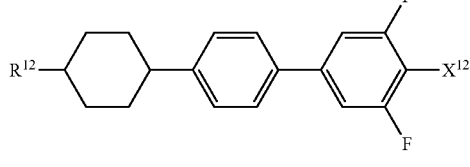 (5-33)
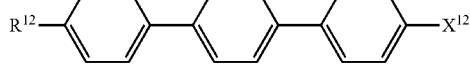 (5-34)
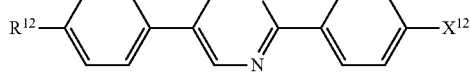 (5-35)
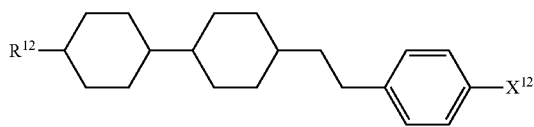 (5-36)
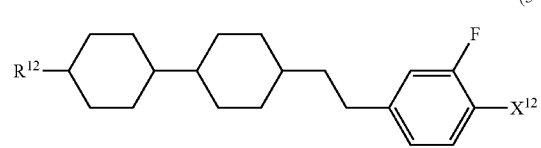 (5-37)
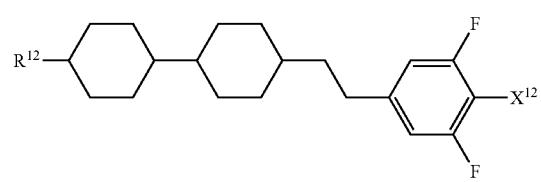 (5-38)
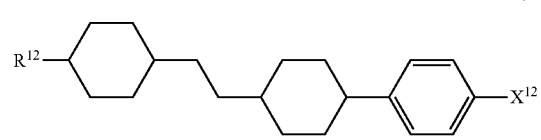 (5-39)
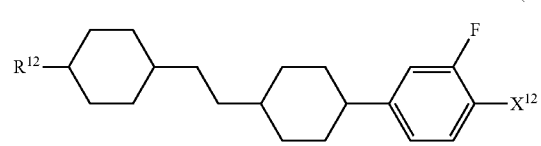 (5-40)
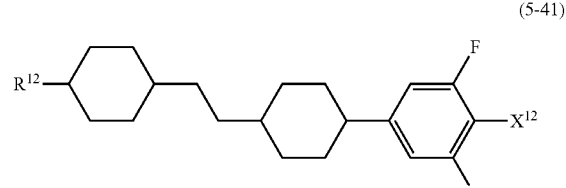 (5-41)
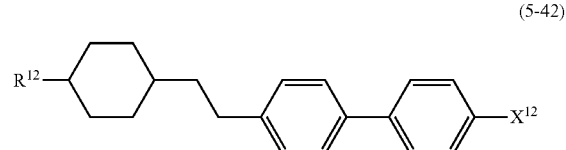 (5-42)
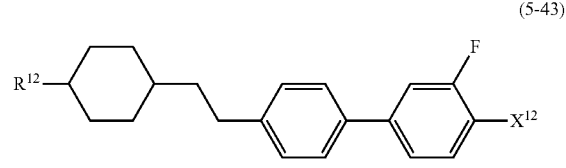 (5-43)
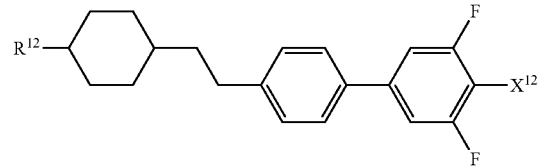 (5-44)
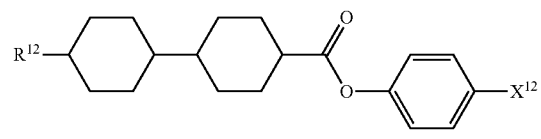 (5-45)

(5-46) 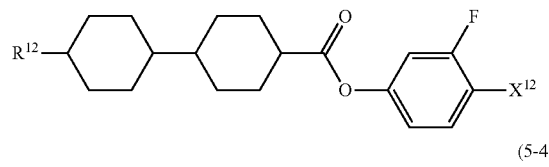
(5-47) 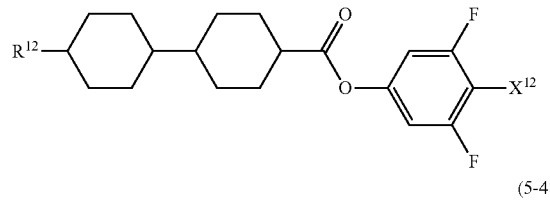
(5-48) 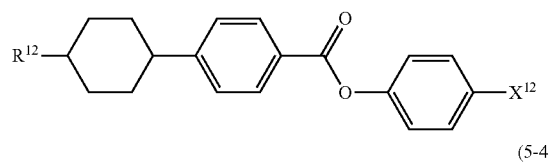
(5-49) 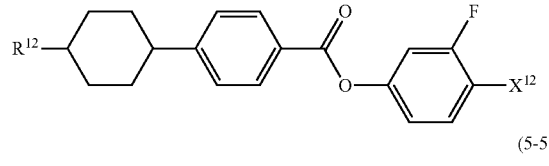
(5-50) 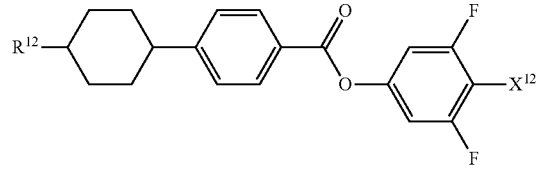
(5-51) 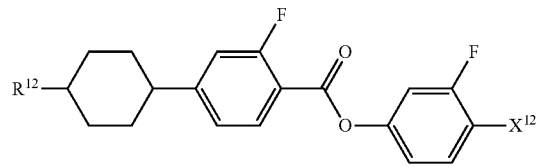
(5-52) 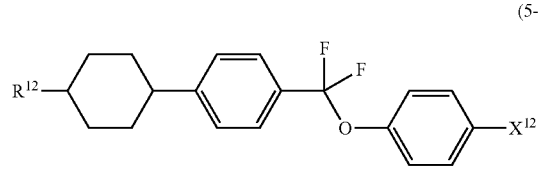
(5-53) 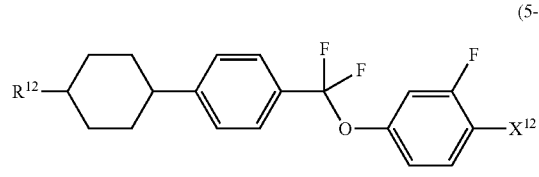
(5-54) 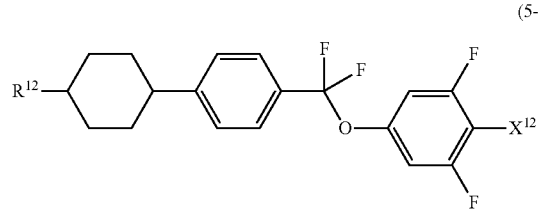
(5-55) 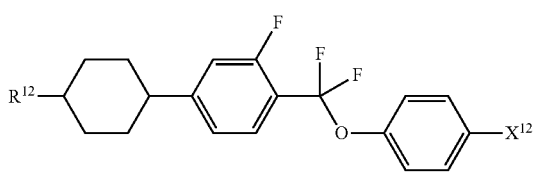
(5-56) 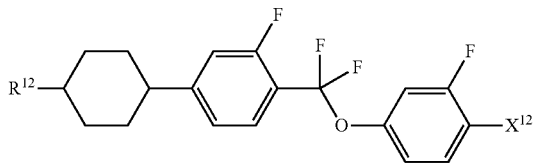
(5-57) 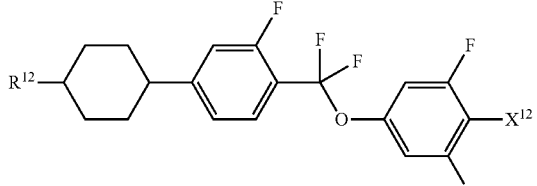
(5-58) 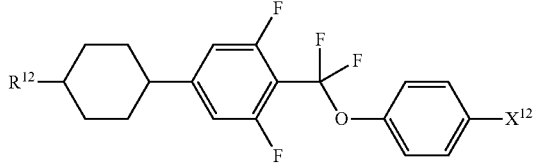
(5-59) 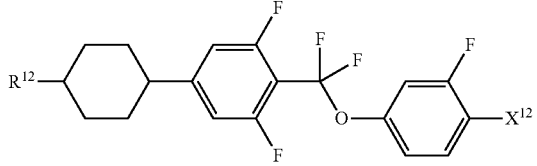
(5-60) 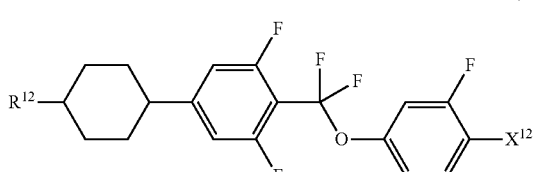
(5-61) 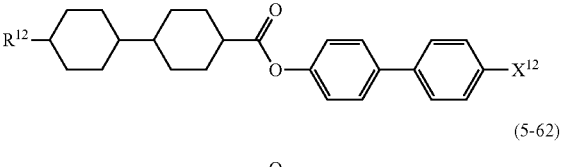
(5-62) 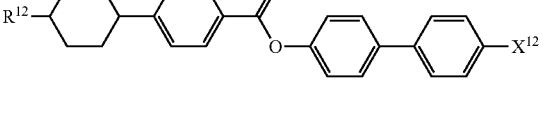

(5-63)
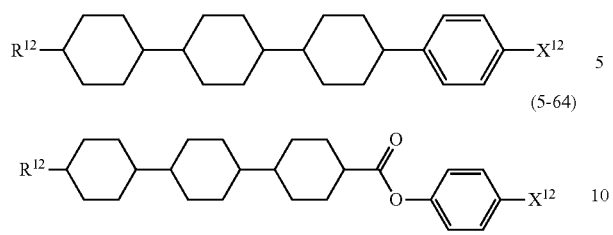

(5-64)
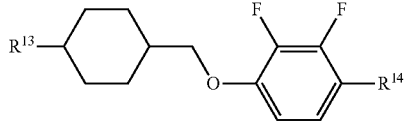

In those compounds (component C), the definitions of $R^{12}$ and $X^{12}$ are the same as those of the formula (5) described in Item 14.

The component C shows positive dielectric anisotropy, and a value thereof is large. Therefore, the component C is mainly used in the case of preparing a composition for a STN mode, a TN mode, or a PSA mode. Through addition of the component C, the dielectric anisotropy of the composition can be increased. The component C has an effect of enlarging the temperature range of a liquid crystal phase, adjusting a viscosity, or adjusting optical anisotropy. The component C is also useful for adjusting a voltage-transmittance curve of the device.

In the case of preparing a composition for a STN mode or a TN mode, the content of the component C suitably falls within a range of from 1 wt % to 99 wt %, preferably a range of from 10 wt % to 97 wt %, more preferably a range of from 40 wt % to 95 wt % with respect to the total weight of the composition. The temperature range of a liquid crystal phase, the viscosity, the optical anisotropy, the dielectric anisotropy, and the like of the composition can be adjusted by adding the component E.

The component D corresponds to compounds (6) to (12). Those compounds have a benzene ring substituted by two halogens at lateral positions as in 2,3-difluoro-1,4-phenylene. Preferred examples of the component D may include compounds (6-1) to (6-8), compounds (7-1) to (7-17), a compound (8-1), compounds (9-1) to (9-3), compounds (10-1) to (10-11), compounds (11-1) to (11-3), and compounds (12-1) to (12-3).

(6-1)
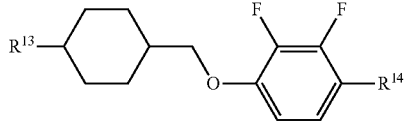

(6-2)
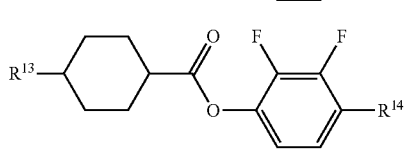

(6-3)
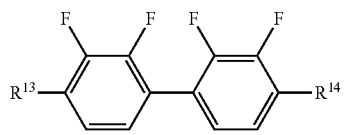

(6-4)
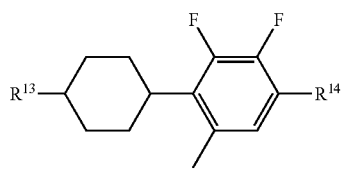

(6-5)
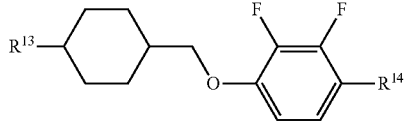

(6-6)
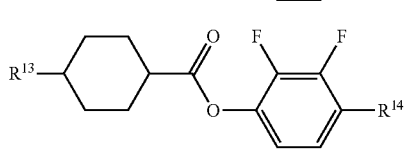

(6-7)
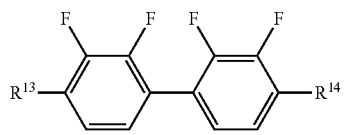

(6-8)
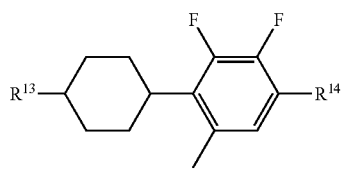

(7-1)
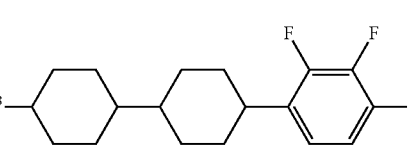

(7-2)
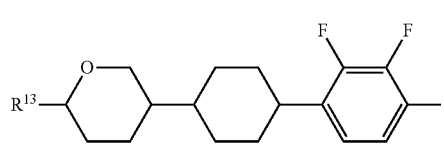

(7-3)
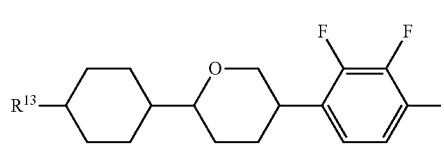

(7-4)
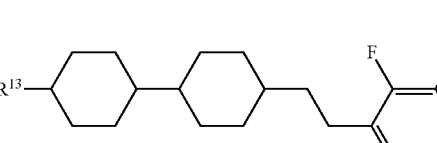

(7-5)
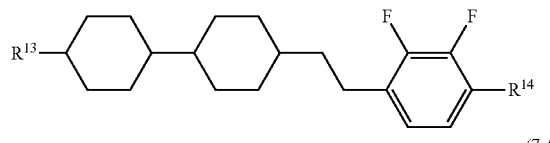

(7-6)
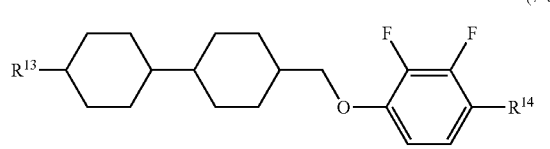

(7-7)
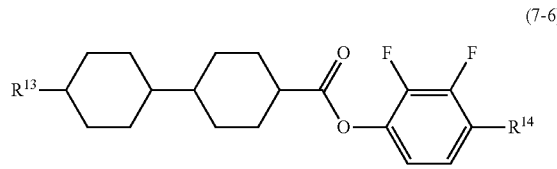

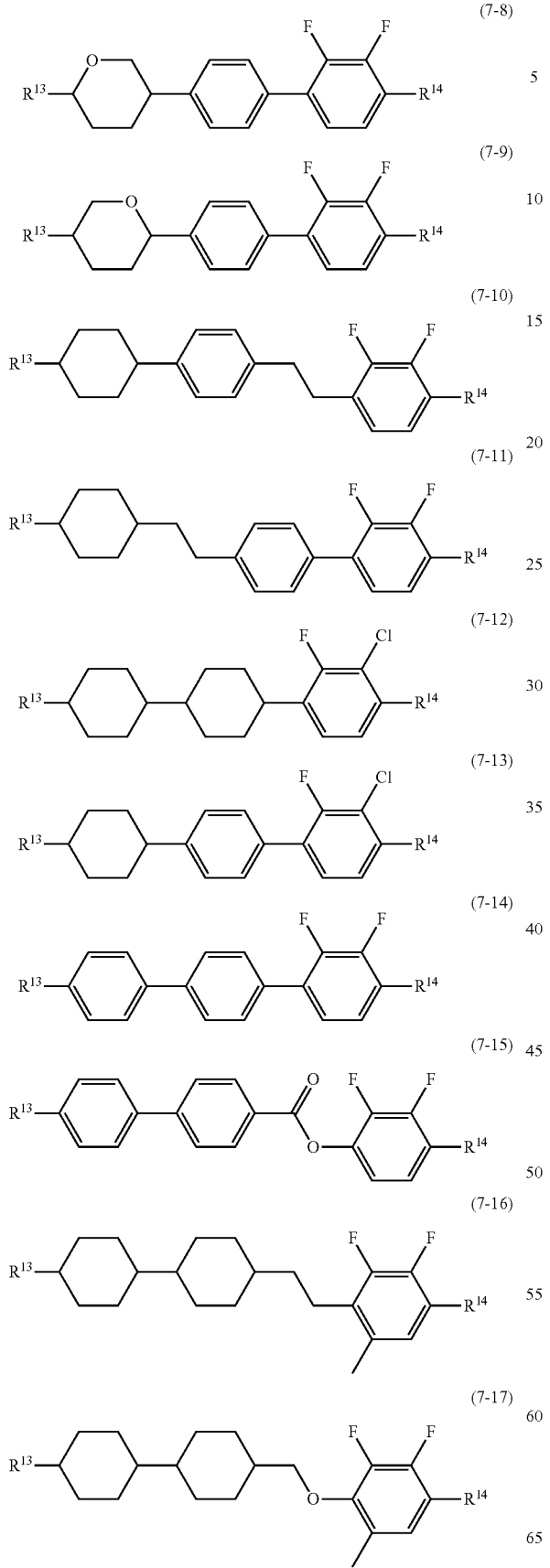
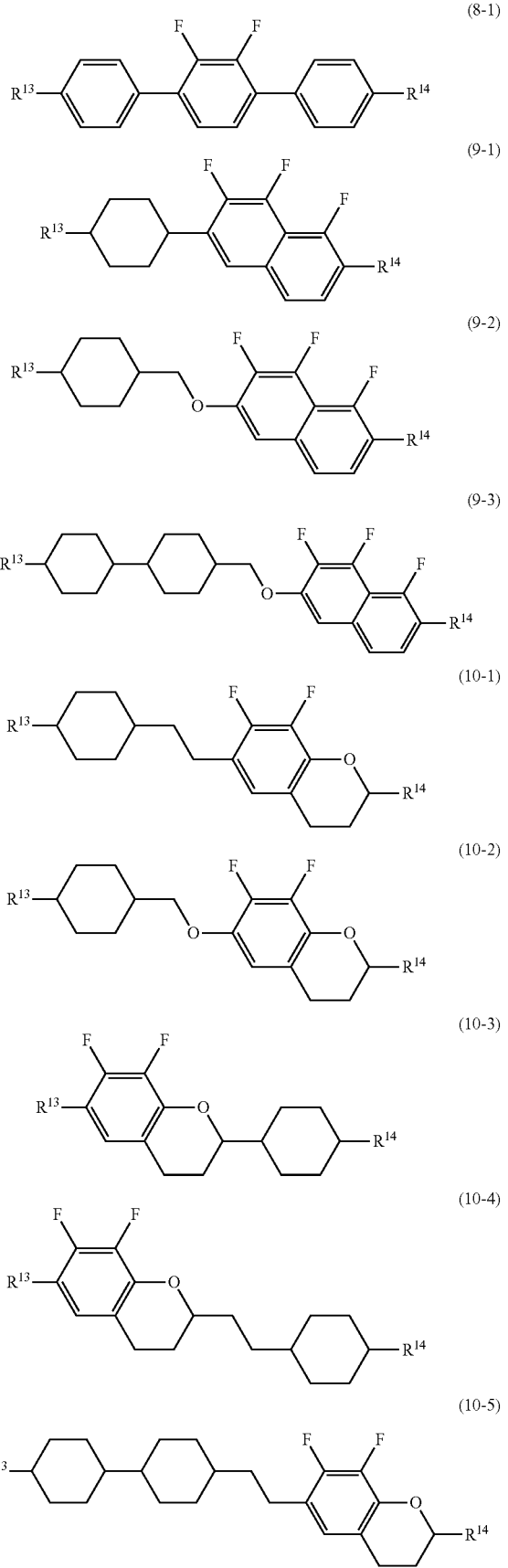

(10-6)
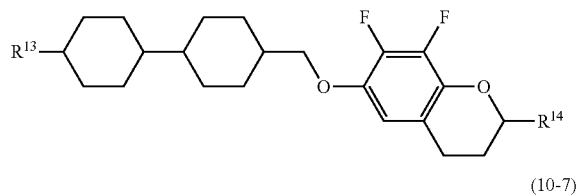

(10-7)
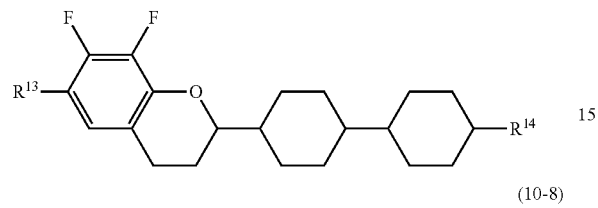

(10-8)
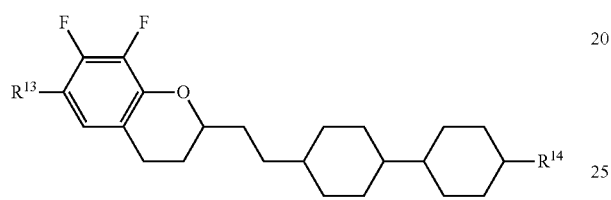

(10-9)
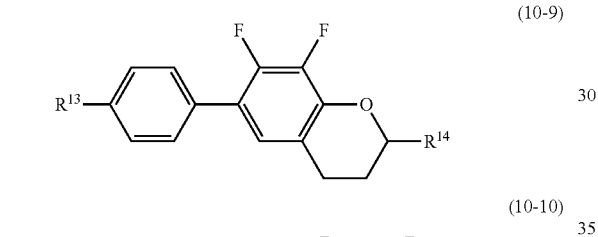

(10-10)
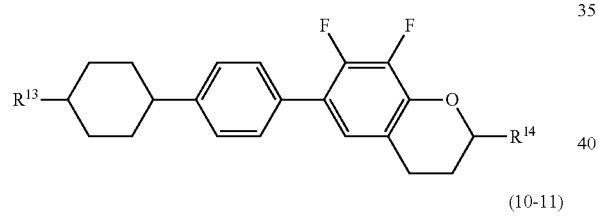

(10-11)
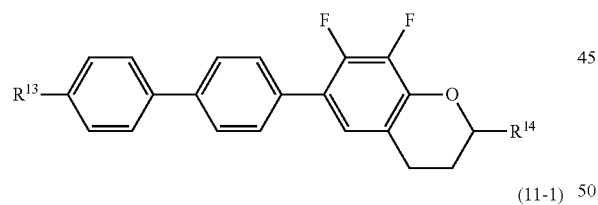

(11-1)
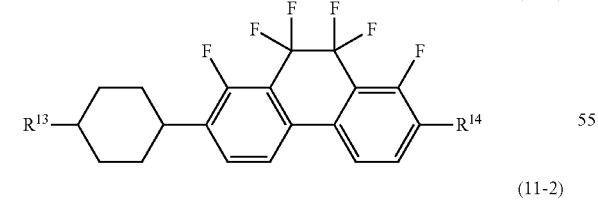

(11-2)
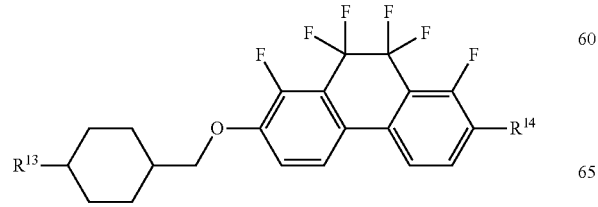

(11-3)
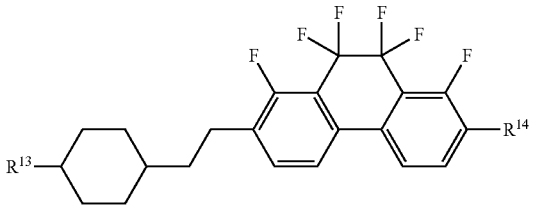

(12-1)
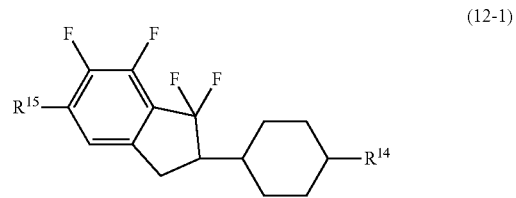

(12-2)
(12-3)
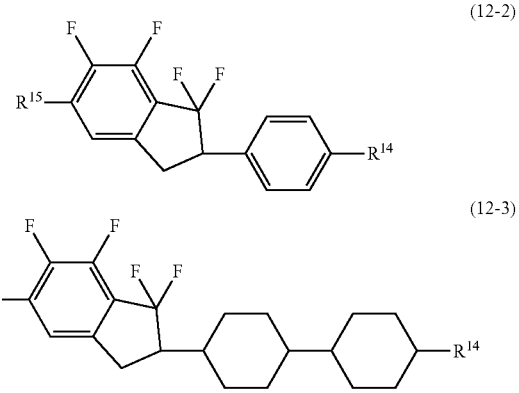

In those compounds (component D), the definitions of $R^{13}$, $R^{14}$, and $R^{15}$ are the same as those of the formulae (6) to (12) described in Item 11.

The component D is a compound showing negative dielectric anisotropy. The component D is mainly used in the case of preparing a composition for a VA mode or a PSA mode. Of the components D, the compound (6) is a bicyclic compound, and hence the compound (6) mainly has an effect of adjusting a viscosity, adjusting optical anisotropy, or adjusting dielectric anisotropy. The compounds (7) and (8) are tricyclic compounds, and hence the compounds (7) and (8) have an effect of increasing a maximum temperature, increasing optical anisotropy, or increasing dielectric anisotropy. The compounds (9) to (12) have an effect of increasing dielectric anisotropy.

In the case of preparing a composition for a VA mode or a PSA mode, the content of the component D is preferably 40 wt % or more, and more preferably falls within a range of from 50 wt % to 95 wt %, with respect to the total weight of the composition. In the case of adding the component D to a composition showing positive dielectric anisotropy, it is preferred that the content of the component D be 30 wt % or less with respect to the total weight of the composition. Through addition of the component D, the elastic constant of the composition can be adjusted, and the voltage-transmittance curve of the device can be adjusted.

The component E is a compound having an alkyl or the like as two terminal groups. Preferred examples of the component E may include compounds (13-1) to (13-11), compounds (14-1) to (14-19), and compounds (15-1) to (15-7).

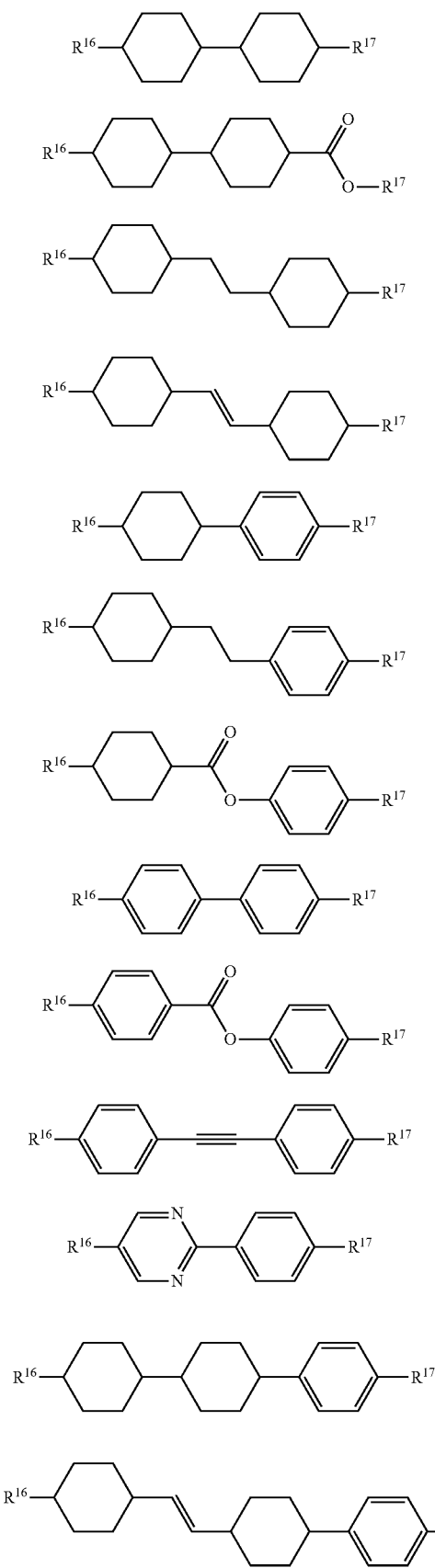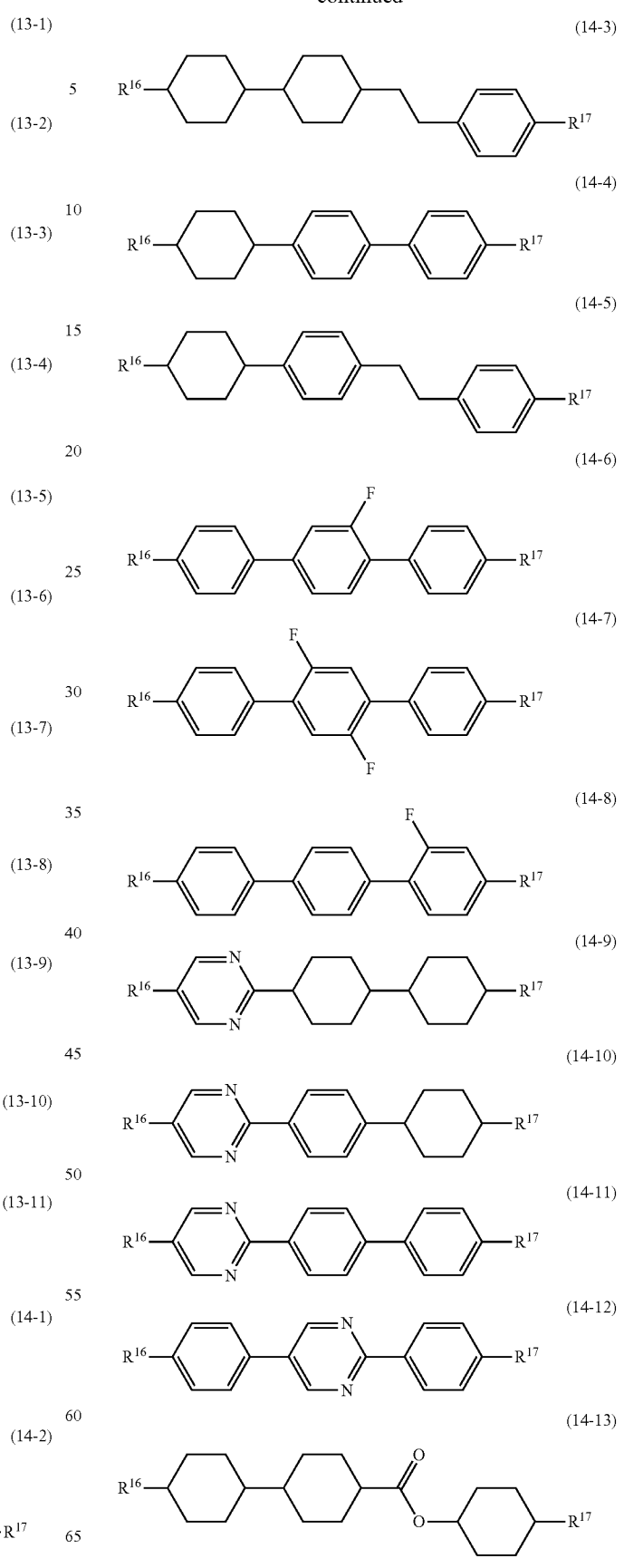

(14-14)
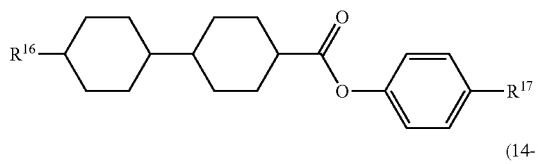

(14-15)
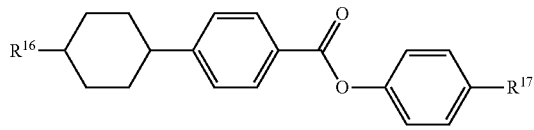

(14-16)
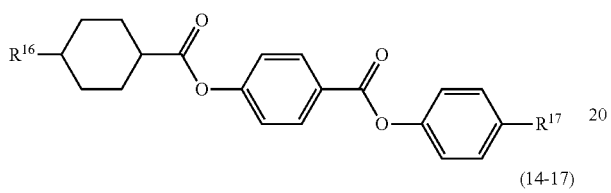

(14-17)
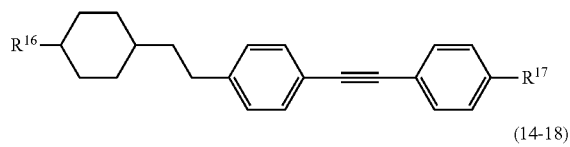

(14-18)
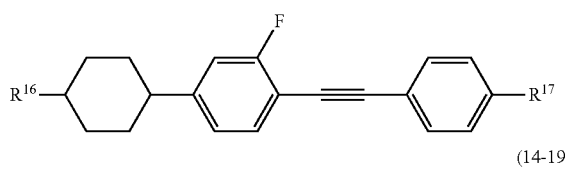

(14-19)
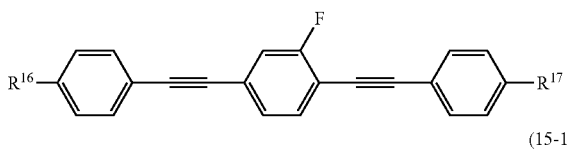

(15-1)
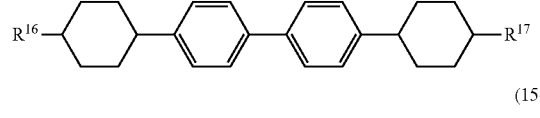

(15-2)
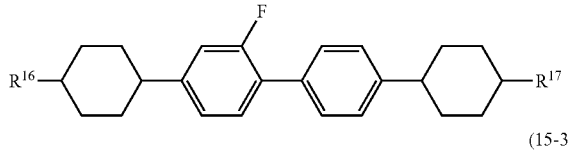

(15-3)
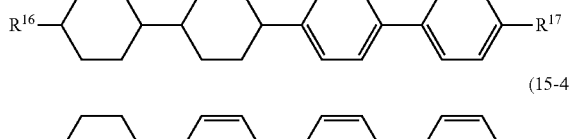

(15-4)
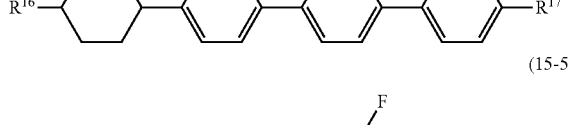

(15-5)
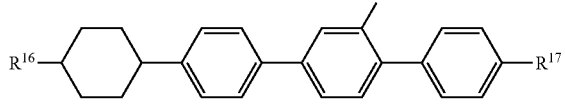

(15-6)
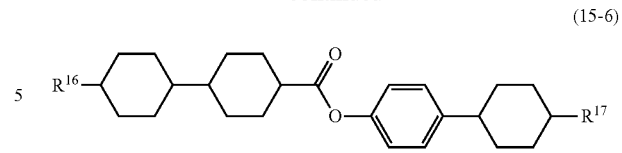

(15-7)

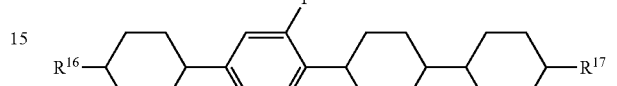

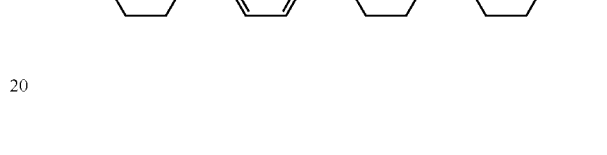

In those compounds (component E), the definitions of $R^{16}$ and $R^{17}$ are the same as those of the formulae (13) to (15) described in Item 12.

The component E is a compound close to a neutral condition due to a small absolute value of dielectric anisotropy. The compound (13) mainly has an effect of adjusting a viscosity or adjusting optical anisotropy. The compounds (14) and (15) have an effect of enlarging the temperature range of a nematic phase by increasing a maximum temperature or an effect of adjusting optical anisotropy.

When the content of the component E is increased, the viscosity of the composition is decreased, but the dielectric anisotropy is decreased. In view of the foregoing, it is preferred that the content of the component E is larger as long as a required value of the threshold voltage of the device is satisfied. Thus, in the case of preparing a composition for a VA mode or a PSA mode, the content of the component E is preferably 30 wt % or more, more preferably 40 wt % or more with respect to the total weight of the composition.

The composition (1) is prepared by a method involving, for example, dissolving required components at high temperature. Depending on the application, additives may be added to the composition. Examples of the additives include an optically active compound, a polymerizable compound, a polymerization initiator, an antioxidant, a UV absorber, a light stabilizer, a heat stabilizer, and an antifoam agent. Those additives are well known to a person skilled in the art and described in literatures.

The composition (1) may further contain at least one optically active compound. As the optically active compound, a known chiral doping agent may be added to the composition (1). The chiral doping agent has an effect of preventing a reverse twist of liquid crystal molecules by inducing a helical structure into the liquid crystal molecules to impart a required twist angle thereto. Preferred examples of the chiral doping agent may include the following compounds (Op-1) to (Op-18). In the compound (Op-18), a ring J represents 1,4-cyclohexylene or 1,4-phenylene, and $R^{24}$ represents an alkyl having 1 to 10 carbon atoms.

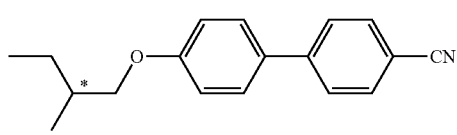 (Op-1)
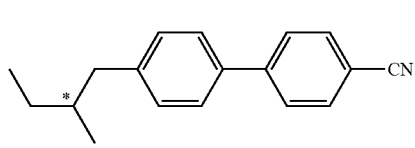 (Op-2)
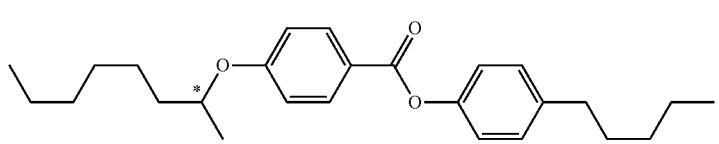 (Op-3)
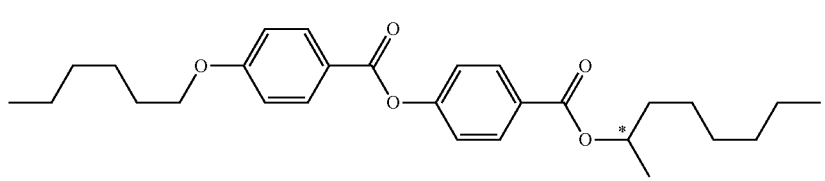 (Op-4)
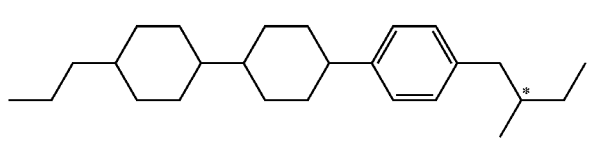 (Op-5)
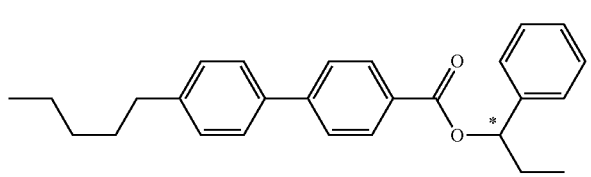 (Op-6)
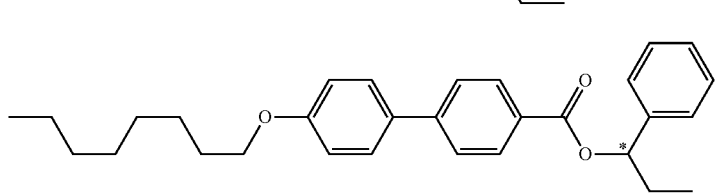 (Op-7)
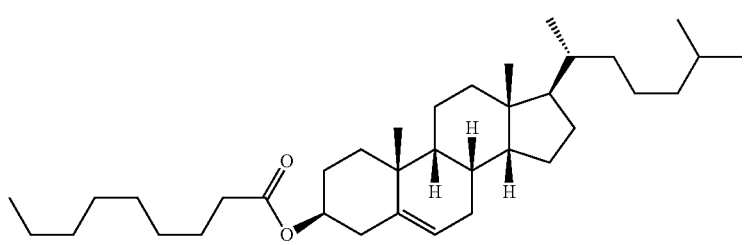 (Op-8)
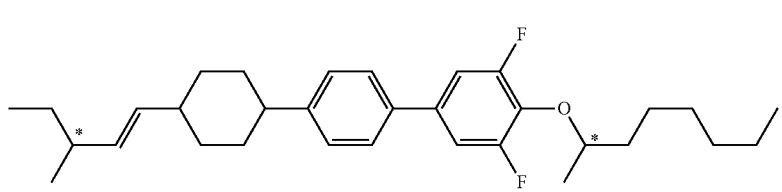 (Op-9)

(Op-10)
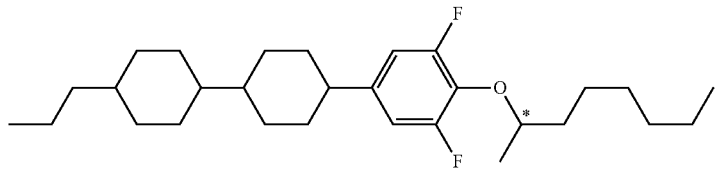
(Op-11)
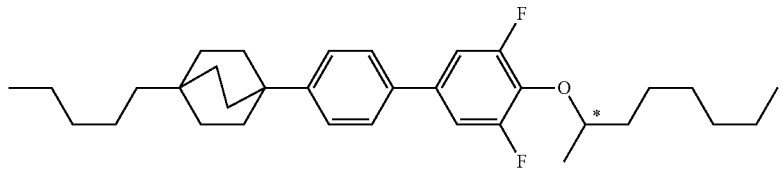
(Op-12)
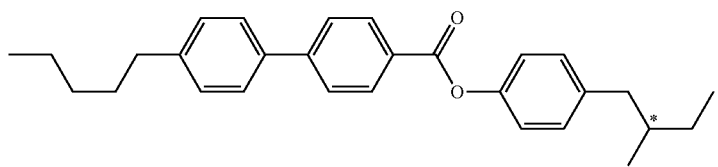
(Op-13)
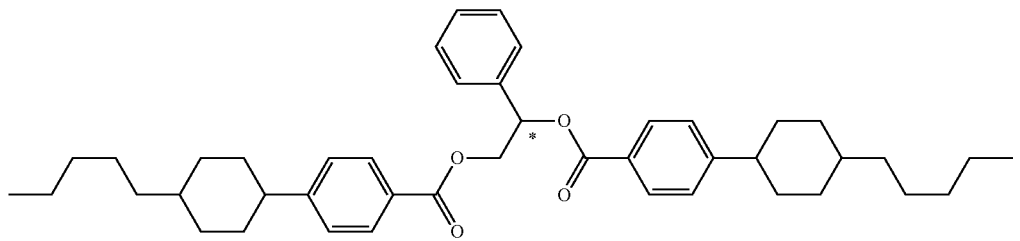
(Op-14)
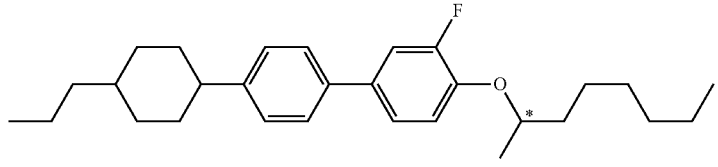
(Op-15)
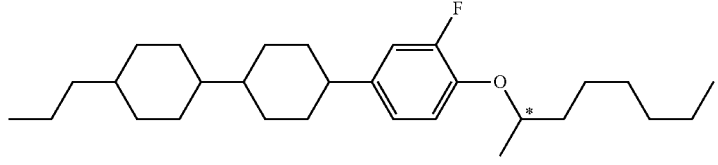
(Op-16)
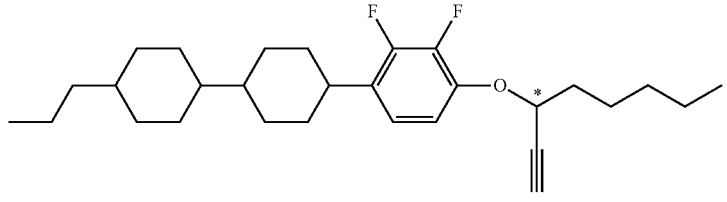
(Op-17)
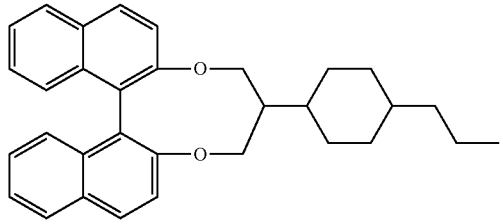

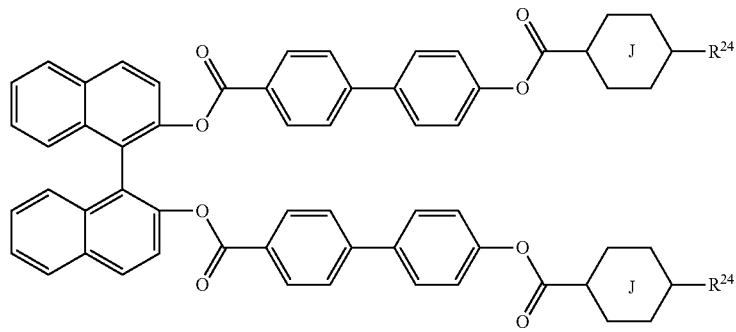

(Op-18)

The helical pitch of the composition (1) is adjusted by adding such optically active compound. In the case of compositions for a TFT mode and a TN mode, it is preferred that the helical pitch be adjusted within a range of from 40 μm to 200 μm. In the case of a composition for a STN mode, it is preferred that the helical pitch be adjusted within a range of from 6 μm to 20 μm. In the case of a composition for a BTN mode, it is preferred that the helical pitch be adjusted within a range of from 1.5 μm to 4 μm. Two or more optically active compounds may be added to the composition (1) for the purpose of adjusting the temperature dependence of the helical pitch.

The composition (1) can also be used for a PSA mode by adding a polymerizable compound thereto. Examples of the polymerizable compound include an acrylate, a methacrylate, a vinyl compound, a vinyloxy compound, a propenyl ether, an epoxy compound (oxirane, oxetane), and a vinyl ketone. Preferred examples thereof may include the following compounds (M-1) to (M-12). The polymerizable compound is polymerized by UV-ray irradiation or the like. The polymerizable compound may be polymerized in the presence of a suitable initiator, such as a photopolymerization initiator. Suitable conditions for the polymerization and a suitable-type and a suitable amount of the initiator are known to a person skilled in the art and described in literatures.

In the compounds (M-1) to (M-12): $R^{20}$ represents hydrogen or methyl; s represents 0 or 1; and t and u each independently represent an integer of from 1 to 10. A symbol F in parentheses represents hydrogen or fluorine.

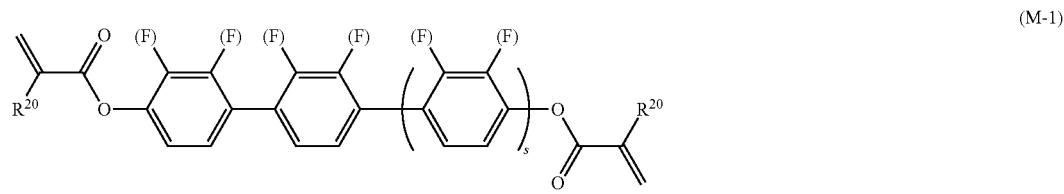

(M-1)

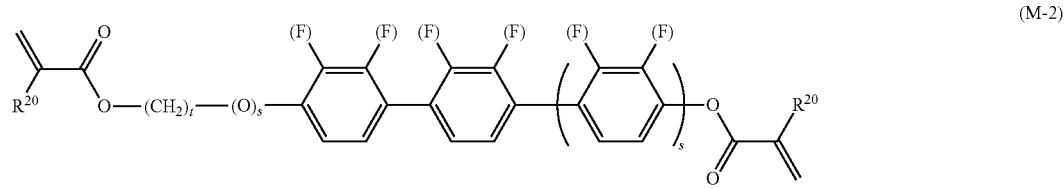

(M-2)

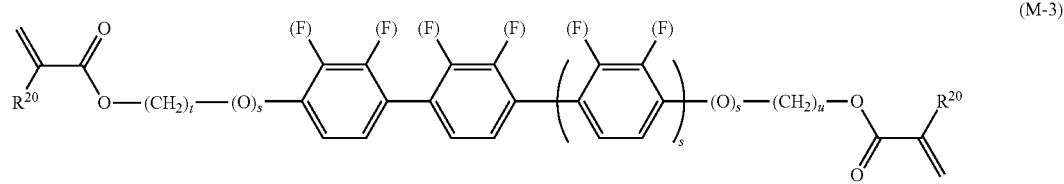

(M-3)

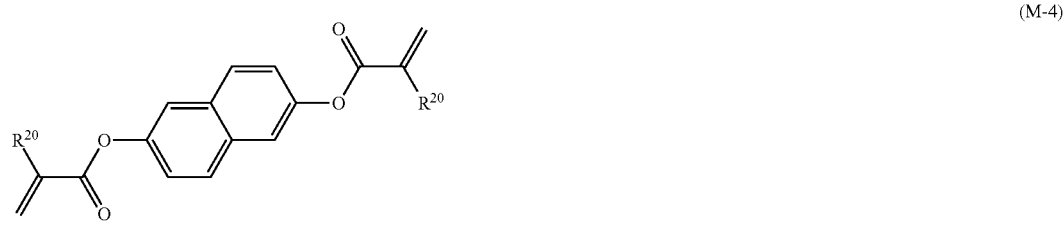

(M-4)

-continued
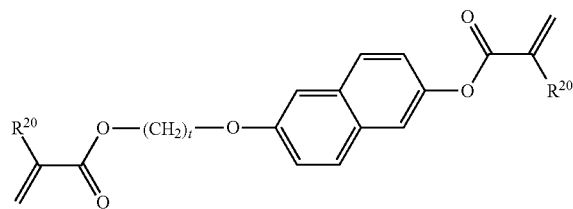
(M-5)
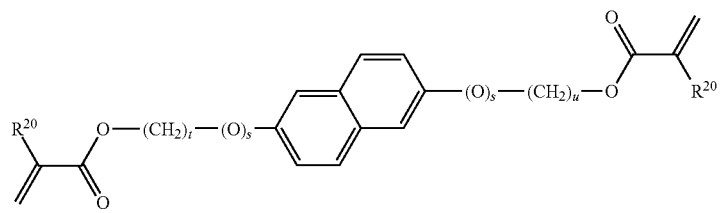
(M-6)
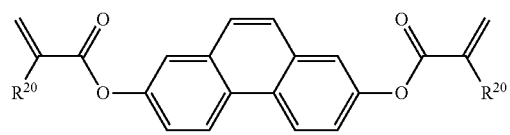
(M-7)
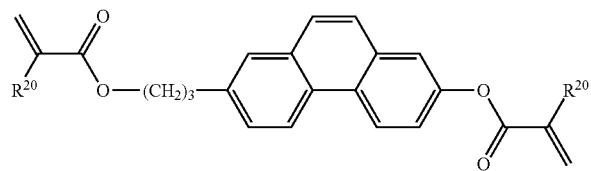
(M-8)
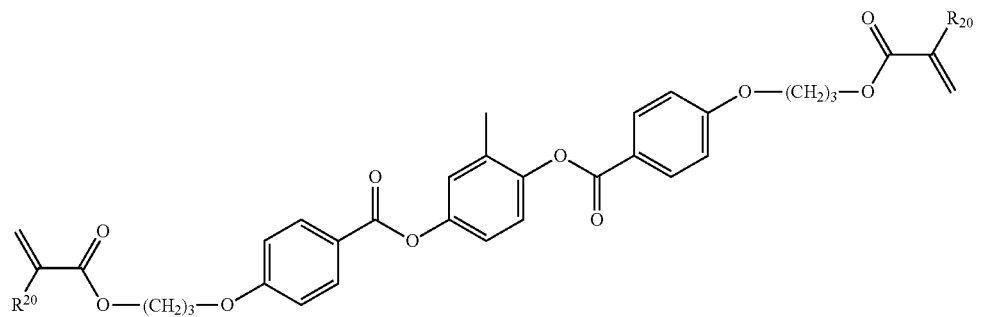
(M-9)
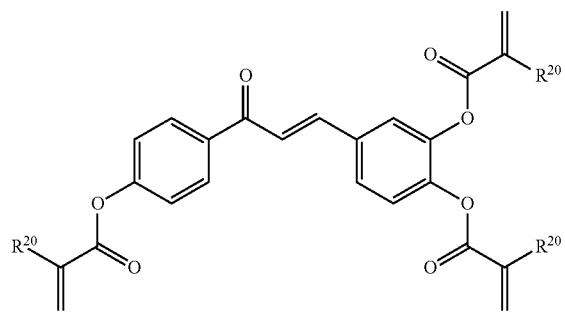
(M-10)
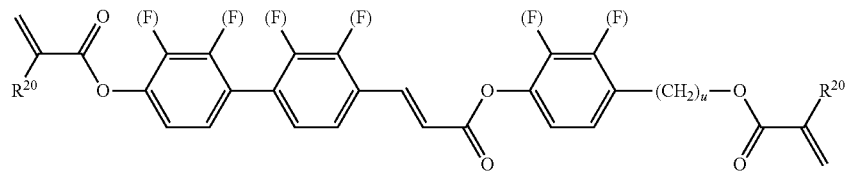
(M-11)

-continued

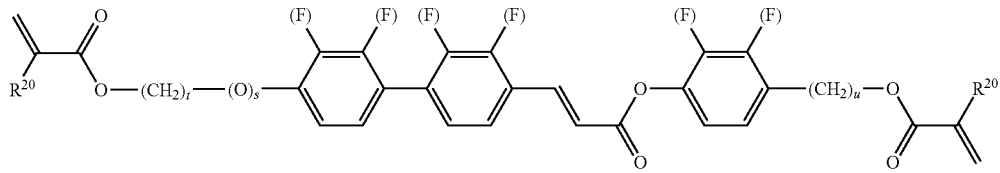

(M-12)

The antioxidant is effective for maintaining a large voltage holding ratio. Preferred examples of the antioxidant may include: the following compound (AO-1) or (AO-2); and IRGANOX 415, IRGANOX 565, IRGANOX 1010, IRGANOX 1035, IRGANOX 3114, or IRGANOX 1098 (trade name: BASF Japan Co., Ltd.). The UV absorber is effective for preventing a decrease in maximum temperature. Preferred examples of the UV absorber include a benzophenone derivative, a benzoate derivative, and a triazole derivative. Specific examples thereof may include: the following compound (AO-3) or (AO-4); TINUVIN 329, TINUVIN P, TINUVIN 326, TINUVIN 234, TINUVIN 213, TINUVIN 400, TINUVIN 328, or TINUVIN 99-2 (trade name: BASF Japan Co., Ltd.); and 1,4-diazabicyclo[2.2.2]octane (DABCO).

The light stabilizer, such as an amine having steric hindrance, is preferred for maintaining a large voltage holding ratio. Preferred examples of the light stabilizer may include: the following compound (AO-5) or (AO-6); and TINUVIN 144, TINUVIN 765, or TINUVIN 770DF (trade name: BASF Japan Co., Ltd.). The heat stabilizer is also effective for maintaining a large voltage holding ratio, and a preferred example thereof may be IRGAFOS 168 (trade name: BASF Japan Co., Ltd.). The antifoam agent is effective for preventing foaming. Preferred examples of the antifoam agent include dimethyl silicone oil and methyl phenyl silicone oil.

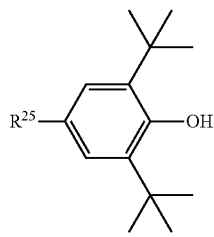

(AO-1)

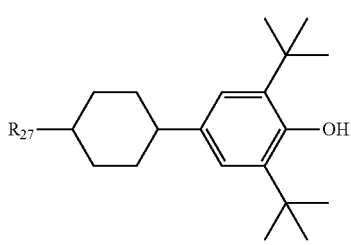

(AO-2)

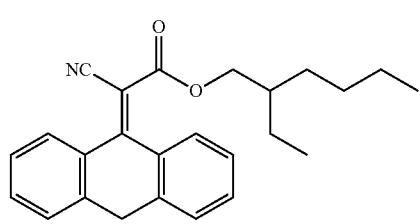

(AO-3)

-continued (AO-4)

(AO-5)

(AO-6)

In the compound (AO-1): $R^{25}$ represents an alkyl having 1 to 20 carbon atoms, an alkoxy having 1 to 20 carbon atoms, —COOR$^{26}$, or —CH$_2$CH$_2$COOR$^{26}$; and $R^{26}$ represents an alkyl having 1 to 20 carbon atoms. In the compounds (AO-2) and (AO-5), $R^{27}$ represents an alkyl having 1 to 20 carbon atoms. In the compound (AO-5): a ring K and a rink L each independently represent 1,4-cyclohexylene or 1, 4-phenylene; v represents 0, 1, or 2; and $R^{28}$ represents hydrogen, methyl, or O.

The composition (1) can also be used for a guest host (GH) mode by adding a dichroic dye, such as a merocyanine dye, a styryl dye, an azo dye, an azomethine dye, an azoxy dye, a quinophthalone dye, an anthraquinone dye, or a tetrazine dye, thereto.

In the composition (1), through appropriate adjustment of kinds and ratios of constituent compounds, the maximum temperature can be set to 70° C. or more, and the minimum temperature can be set to −10° C. or less, and hence the temperature range of a nematic phase is wide. Thus, a liquid crystal display device containing this composition can be used within a wide temperature range.

In the composition (1), through appropriate adjustment of kinds and ratios of constituent compounds, the optical anisotropy can be set within a range of from 0.10 to 0.13 or within a range of from 0.05 to 0.18. Similarly, the dielectric anisotropy can be adjusted within a range of from −5.0 to −2.0. The preferred dielectric anisotropy falls within a range of from −4.5 to −2.5. The composition (1) having dielectric anisotropy within this range can be suitably used for a liquid crystal display device that is operated in an IPS mode, a VA mode, or a PSA mode.

3. Liquid Crystal Display Device

The composition (1) can be used for an AM device. Further, the composition (1) can also be used for a PM device. This composition can be used for an AM device and a PM device having a mode such as PC, TN, STN, ECB, OCB, IPS, FFS, VA, PSA, and FPA. It is particularly preferred that the composition (1) be used for an AM device having a TN, OCB, IPS, or FFS mode. In the AM device having an IPS mode or an FFS mode, the alignment of liquid crystal molecules under application of no voltage may be parallel or perpendicular to a panel substrate. Those devices may each be a reflection-type, transmission-type, or semi-transmission-type device. It is preferred that the composition (1) be used for a transmission-type device. The composition (1) can also be used for an amorphous silicon-TFT device or a polycrystalline silicon-TFT device. The composition (1) can also be used for a nematic curvilinear aligned phase (NCAP)-type device manufactured by microcapsulating the composition or a polymer dispersed (PD)-type device in which a three-dimensional network polymer is formed in the composition.

The composition (1) has negative dielectric anisotropy, and hence the composition (1) can be suitably used for a liquid crystal display device that has an operation mode, such as a VA mode, an IPS mode, or a PSA mode, and is driven in an AM system. This composition can be particularly suitably used for a liquid crystal display device that has a VA mode and is driven in an AM system.

In a liquid crystal display device that is operated in a TN mode, a VA mode, or the like, the direction of an electric field is perpendicular to a liquid crystal layer. Meanwhile, in a liquid crystal display device that is operated in an IPS mode or the like, the direction of an electric field is parallel to a liquid crystal layer. The structure of the liquid crystal display device that is operated in a VA mode has been reported in K. Ohmuro, S. Kataoka, T. Sasaki, and Y. Koike, SID'97 Digest of Technical Papers, 28, 845 (1997). The structure of the liquid crystal display device that is operated in an IPS mode has been reported in WO 91/10936 A1 (family: U.S. Pat. No. 5,576,867 A).

EXAMPLES

The present invention is described in more detail by way of Examples. The present invention is not limited to the following Examples.

1-1. Example of Compound (1)

The compound (1) was synthesized by the following procedure. The synthesized compound was identified by a method such as NMR analysis. The physical properties of the compound were measured by methods described below.

NMR Analysis

As a measurement device, DRX-500 (manufactured by Bruker BioSpin K.K.) was used. In a $^1$H-HMR measurement, a sample was dissolved in a deuterated solvent, such as $CDCl_3$, and the measurement was performed under conditions of room temperature, 500 MHz, and a number of scans of 16. Tetramethylsilane was used as an internal standard. In a $^{19}$F-NMR measurement, $CFCl_3$ was used as an internal standard, and the measurement was performed at a number of scans of 24. In the description of a nuclear magnetic resonance spectrum, s represents a singlet, d represents a doublet, t represents a triplet, q represents a quartet, quin represents a quintet, sex represents a sextet, m presents a multiplet, and br represents a broad.

Measurement Sample

In order to measure a phase structure and a transition temperature, a liquid crystal compound itself was used as a sample. In order to measure the physical properties, such as a maximum temperature of a nematic phase, a viscosity, optical anisotropy, and dielectric anisotropy, a composition prepared by mixing the compound with base liquid crystal was used as a sample.

In the case of using a sample obtained by mixing the compound with the base liquid crystal, the measurement was performed by the following method. A sample was prepared by mixing 15 wt % of the compound and 85 wt % of the base liquid crystal. From a measured value of this sample, an extrapolated value was calculated in accordance with an extrapolation method represented by the following expression, and this value was described.

<Extrapolated value>=(100×<measured value of sample>−<wt % of base liquid crystal>×<measured value of base liquid crystal>)/<wt % of compound>

When a crystal (or a smectic phase) was precipitated at 25° C. even when the ratio between the compound and the base liquid crystal was as described above, the ratio between the compound and the base liquid crystal was successively changed from 10 wt %:90 wt % to 5 wt %:95 wt % and then to 1 wt %:99 wt %, and the physical properties of the sample were measured at the ratio in which the precipitation of the crystal (or the smectic phase) at 25° C. was stopped. Unless otherwise specified, the ratio between the compound and the base liquid crystal is 15 wt %:85 wt %.

As the base liquid crystal, a base liquid crystal (i) described below was used. The ratio of components of the base liquid crystal (i) is shown in terms of wt %.

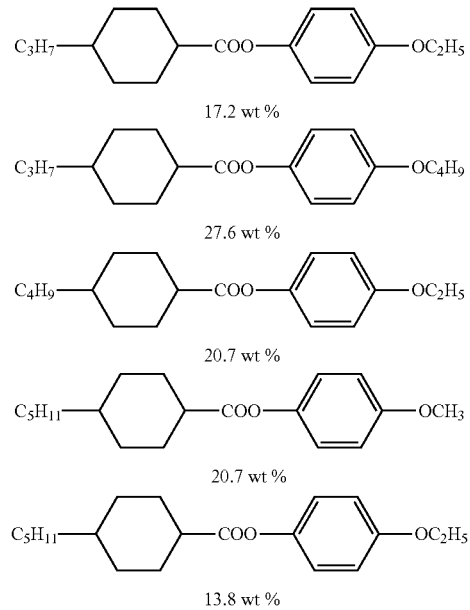

Measurement Method

The physical properties were measured by the following methods. Most of those methods were the methods described in JEITA specification (JEITA*ED-2521A) discussed and established by Japan Electronics and Information Technology Industries Association (hereinafter abbreviated as "JEITA"), or modified methods thereof.

A TFT was not mounted on a TN device used for the measurement.

(1) Phase Structure

A sample was placed on a hot plate (FP-52-type hot stage, Mettler Co., Ltd.) of a melting point measurement device provided with a polarization microscope, and a phase state and a change thereof were observed with the polarization microscope while the sample was being heated at a rate of 3° C./min to specify the kind of the phase.

(2) Transition Temperature (° C.)

The temperature of the sample was increased and decreased at a rate of 3° C./min through use of a scanning calorimeter DSC-7 system manufactured by PerkinElmer Co., Ltd. or Diamond DSC system, and a starting point of an endothermic peak or an exothermic peak involved in the phase change of the sample was determined by extrapolation to determine a transition temperature. A temperature at which the transition of the compound from a solid to a liquid crystal phase, such as a smectic phase or a nematic phase, occurs is sometimes abbreviated as "minimum temperature of a liquid crystal phase". A temperature at which the transition of the compound from a liquid crystal phase to a liquid occurs is sometimes abbreviated as "clearing point".

The crystal was represented by C. When the kind of the crystal was able to be distinguished, the crystal was represented by $C_1$ or $C_2$. The smectic phase was represented by S, and the nematic phase was represented by N. When the smectic phase was able to be distinguished into a smectic A phase, a smectic B phase, a smectic C phase, or a smectic F phase, those phases were respectively represented by $S_A$, $S_B$, $S_C$, and $S_F$. The liquid (isotropic) was represented by I. The transition temperature was expressed by, for example, "C 50.0 N 100.0 I". This expression means that the transition temperature from a crystal to a nematic phase is 50.0° C., and the transition temperature from a nematic phase to a liquid is 100.0° C.

(3) Low-Temperature Compatibility

A sample was prepared by mixing a base liquid crystal and a compound so that the ratio of the compound became 20 wt %, 15 wt %, 10 wt %, 5 wt %, 3 wt %, and 1 wt %, and the sample was loaded into a glass bottle. The glass bottle was stored in a freezer at −10° C. or −20° C. for a predetermined period of time, and then it was observed whether or not a crystal (or a smectic phase) was precipitated.

(4) Maximum Temperature of Nematic Phase ($T_{NI}$ or NI; ° C.)

A sample was placed on a hot plate of a melting point measurement device provided with a polarization microscope and heated at a rate of 1° C./min. A temperature at which part of the sample changed from a nematic phase to an isotropic liquid was measured. When the sample was a mixture of a compound and a base liquid crystal, the symbol $T_{NI}$ was used. When the sample was a mixture of a compound and a component B or the like, the symbol NI was used.

(5) Minimum Temperature of Nematic Phase ($T_C$; ° C.)

A sample having a nematic phase was stored in a freezer at 0° C., −10° C., −20° C., −30° C., and −40° C. for 10 days, and then a liquid crystal phase was observed. For example, when the sample maintained the nematic phase at −20° C. and changed to a crystal or a smectic phase at −30° C., $T_C$ was described as ≤−20° C.

(6) Viscosity (Bulk Viscosity; η; Measured at 20° C.; mPa·s)

The measurement was performed through use of an E-type rotatory viscometer.

(7) Viscosity (Rotational Viscosity; γ1; Measured at 25° C.; mPa·s)

The measurement was performed in accordance with a method described in M. Imai et al., Molecular Crystals and Liquid Crystals, Vol. 259, 37 (1995). A sample was placed in a VA device in which the interval (cell gap) between two glass substrates was 20 μm. A voltage was applied to the device in stages by 1 volt within a range of from 30 volts to 50 volts. After the application of the voltage was suspended for 0.2 second, the application of the voltage was repeated under conditions of only one rectangular wave (rectangular pulse; 0.2 second) and non-application (2 seconds). A peak current and a peak time of a transient current caused by the application were measured. From those measured values and a calculation expression (8) on page 40 of the literature of M. Imai et al., a value of a rotational viscosity was obtained. As dielectric anisotropy required for this calculation, a value measured in the following section of dielectric anisotropy was used.

(8) Optical Anisotropy (Refractive Index Anisotropy; Measured at 25° C.; Δn)

The measurement was performed with an Abbe's refractometer having a polarizing plate mounted on an eyepiece through use of light having a wavelength of 589 nm. The surface of a main prism was rubbed in one direction, and then a sample was dropped onto the main prism. A refractive index (n//) was measured when the direction of polarization was parallel to the direction of the rubbing. A refractive index (n⊥) was measured when the direction of polarization was perpendicular to the direction of the rubbing. A value of optical anisotropy (Δn) was calculated by an expression: Δn=n//−n⊥.

(9) Dielectric Anisotropy (Δ∈; Measured at 25° C.)

A value of dielectric anisotropy was calculated by an expression: Δ∈=∈//−∈⊥. A dielectric constant (∈// and ∈⊥) was measured as described below.

1) Measurement of dielectric constant (∈//): A solution of octadecyltriethoxysilane (0.16 ml) in ethanol (20 ml) was applied onto a well-washed glass substrate. The glass substrate was rotated with a spinner and heated at 150° C. for 1 hour. A sample was placed in a VA device in which the interval (cell gap) between two glass substrates was 4 μm, and the device was sealed with a UV-curable adhesive. A sine wave (0.5 V, 1 kHz) was applied to the device, and a dielectric constant (∈//) in a long axis direction of liquid crystal molecules was measured after 2 seconds.

2) Measurement of dielectric constant (∈⊥): A polyimide solution was applied onto a well-washed glass substrate. The glass substrate was fired, and then an obtained alignment film was subjected to rubbing treatment. A sample was placed in a TN device in which the interval (cell gap) between two glass substrates was 9 μm, and a twist angle was 80°. A sine wave (0.5 V, 1 kHz) was applied to the device, and a dielectric constant (∈⊥) in a short axis direction of liquid crystal molecules was measured after 2 seconds.

(10) Elastic Constant ($K_{11}$ and $K_{33}$; Measured at 25° C.; pN)

An EC-1-type elastic constant measurement instrument manufactured by TOYO Corporation was used for measurement. A sample was placed in a homeotropic alignment device in which the interval (cell gap) between two glass substrates was 20 μm. A charge of from 20 volts to 0 volts was applied to the device to measure an electrostatic capacitance and an applied voltage. The values of the electrostatic capacitance (C) and the applied voltage (V) were subjected to fitting through use of an expression (2.98) and an expression (2.101) on page 75 of "Liquid crystal device handbook" (Nikkan Kogyo Shinbun Ltd.), and a value of an elastic constant was determined by an expression (2.100).

(11) Threshold Voltage (Vth; Measured at 25° C.; V)

An LCD5100-type luminance meter manufactured by Otsuka Electronics Co., Ltd. was used for measurement. A light source was a halogen lamp. A sample was placed in a VA device in a normally black mode in which the interval (cell gap) between two glass substrates was 4 µm, and the rubbing direction was antiparallel, and the device was sealed with a UV-curable adhesive. A voltage (60 Hz, rectangular wave) applied to the device was increased in stages by 0.02 V from 0 V to 20 V. In this case, the device was irradiated with light from a direction perpendicular to the device, and the amount of light having passed through the device was measured. A voltage-transmittance curve was prepared in which a transmittance reached 100% when the amount of light became maximum and a transmittance reached 0% when the amount of light became minimum. The threshold voltage is a voltage when the transmittance reaches 10%.

(12) Voltage Holding Ratio (VHR-1; Measured at 25° C.; %)

A TN device used for measurement had a polyimide alignment film, and the interval (cell gap) between two glass substrates was 5 µm. After a sample was placed in the device, the device was sealed with a UV-curable adhesive. The TN device was charged by applying a pulse voltage (5 V for 60 microseconds) thereto. An attenuating voltage was measured with a high-speed voltmeter for 16.7 milliseconds, and an area A between a voltage curve and a horizontal axis in a unit period was determined. An area B is an area in which the voltage does not attenuate. The voltage holding ratio is a percentage of the area A with respect to the area B.

(13) Voltage Holding Ratio (VHR-2; Measured at 80° C.; %)

A TN device used for measurement had a polyimide alignment film, and the interval (cell gap) between two glass substrates was 5 µm. After a sample was placed in the device, the device was sealed with a UV-curable adhesive. The TN device was charged by applying a pulse voltage (5 V for 60 microseconds) thereto. An attenuating voltage was measured with a high-speed voltmeter for 16.7 milliseconds, and an area A between a voltage curve and a horizontal axis in a unit period was determined. An area B is an area in which the voltage does not attenuate. The voltage holding ratio is a percentage of the area A with respect to the area B.

(14) Light Resistance

A glass substrate subjected to oblique evaporation of silicon dioxide was prepared. A sample was placed in a cell in which the interval (cell gap) between the obtained two glass substrates was 10 µm to manufacture a TN device. The TN device was irradiated with a UV ray at 12 mW/cm² for 20 minutes (distance between a light source and a subject was 20 cm). A clearing point of the resultant sample was measured by the above-mentioned method and compared to a clearing point of the sample before the irradiation with a UV ray. It is considered that as the change becomes smaller, the light resistance becomes more excellent.

Example 1

Synthesis of Compound (No. 13)

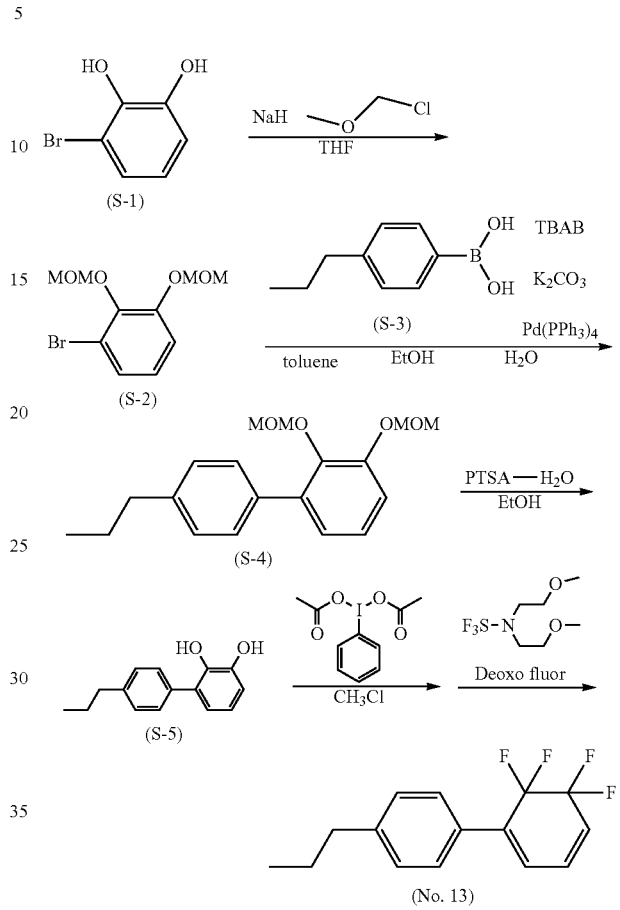

First Step

Sodium hydride (10.2 g) and THF (240 ml) were loaded into a reaction vessel and cooled to 0° C. under a nitrogen atmosphere. A solution of a compound (S-1) (20 g) in THF (50 ml) was slowly added to the resultant, followed by stirring for 1 hour. Then, chloromethyl ether (25.5 g) was slowly added to the resultant and the temperature was increased to room temperature. Water was poured into the reaction mixture, and the aqueous layer was extracted with ethyl acetate. The organic layer was washed with water and saturated saline and dried with anhydrous magnesium sulfate. The solution was concentrated under reduced pressure, and the residue was purified by silica gel column chromatography (toluene) to provide a compound (S-2) (19.0 g; 65%).

Second Step

The compound (S-2) (19.0 g) obtained in the above-mentioned step and a compound (S-3) (16.9 g) were dissolved in toluene (100 ml) under a nitrogen atmosphere, and water (50 ml), ethanol (50 ml), Pd (PPh₃)₄ (3.9 g), tetra-n-butylammonium bromide (TBAB) (0.45 g), and potassium carbonate (28.49 g) were added to the resultant, followed by heating to reflux for 6 hours. After the completion of the reaction, the resultant was extracted with ethyl acetate and washed with a saturated sodium chloride aqueous solution and water. Then, the resultant was dried with anhydrous magnesium sulfate and concentrated under reduced pressure to provide a light brown solid. The light brown solid was purified by silica gel column chromatography (ethyl acetate: toluene=1:9 in terms of a volume ratio) to provide a compound (S-4) (12.8 g; 59%).

Third Step

The compound (S-4) (21.8 g) obtained in the above-mentioned step and ethanol (250 ml) were loaded into a reaction vessel under a nitrogen atmosphere. Then, p-toluenesulfonic acid monohydrate (30 g) was added to the mixture with stirring, followed by heating to reflux for 1 hour. The reaction mixture was poured into water, and the aqueous layer was extracted with toluene. The organic layer was fractionated, washed with a saturated aqueous solution of sodium bicarbonate and water, and dried with anhydrous magnesium sulfate. The solution was concentrated under reduced pressure, and the residue was purified by silica gel column chromatography (toluene:ethyl acetate=7:1 in terms of a volume ratio) to provide a compound (S-5) (7.89 g; 85%).

Fourth Step

The compound (S-5) (7.7 g) obtained in the above-mentioned step and chloroform (250 ml) were loaded into a reaction vessel and cooled to 0° C. under a nitrogen atmosphere. Then, iodobenzene diacetate (15.2 g) was added to the mixture, and the resultant mixture was returned to room temperature, followed by stirring for 5 minutes. The reaction system was again cooled to 0° C., and Deoxo-fluor (44 g) was added to the reaction system. The resultant was stirred for 2 days while being returned to room temperature. The mixture was poured into ice water. The organic layer was fractionated, washed with a saturated aqueous solution of sodium bicarbonate and water, and dried with anhydrous magnesium sulfate. The solution was concentrated under reduced pressure, and the residue was purified by silica gel column chromatography (heptane:toluene=3:1 in terms of a volume ratio) to provide a compound (No. 13) (700 mg; 7.6%).

Chemical shift δ (ppm; CDCl$_3$): 7.48 (d, 2H), 7.22 (d, 2H), 6.45-6.44 (m, 1H), 6.05-6.02 (m, 1H), 5.70-5.59 (m, 1H), 2.61 (t, 2H), 1.66 (sex, 2H), 0.96 (t, 3H).

The physical properties of the compound (No. 13) were as described below.

Maximum temperature ($T_{NI}$)=−155.4° C.; optical anisotropy (Δn)=0.008; dielectric anisotropy (Δ∈)=−0.87; viscosity (η)=50.6 mPa·s.

Example 2

A compound (No. 107) was obtained by using a compound (S-6) instead of the compound (S-3) in Example 1.

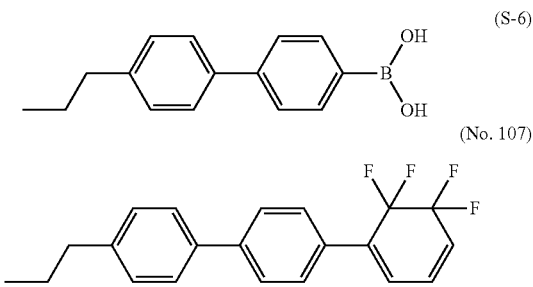

Chemical shift δ (ppm; CDCl$_3$): 7.63 (s, 4H), 7.55 (d, 2H), 7.27 (d, 2H), 6.53-6.52 (m, 1H), 6.07-6.04 (m, 1H), 5.73-5.62 (m, 1H), 2.63 (t, 2H), 1.69 (sex, 2H), 0.98 (t, 3H).

The physical properties of the compound (No. 107) were as described below.

Transition temperature: C 61.8 (S 54.0) I.

Maximum temperature ($T_{NI}$)=2.6° C.; optical anisotropy (Δn)=0.156; dielectric anisotropy (Δ∈)=−1.81.

Example 3

Synthesis of Compound (No. 94)

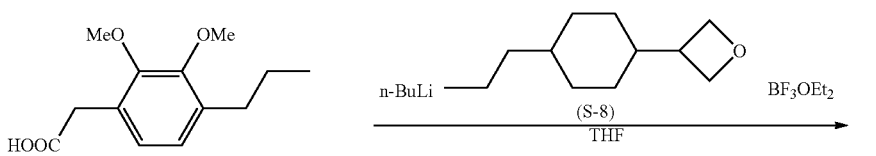

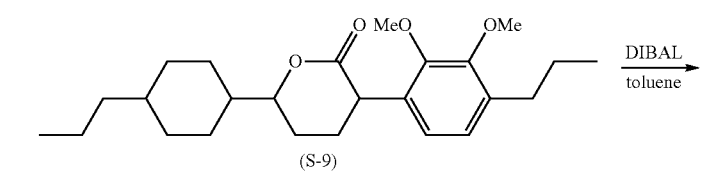

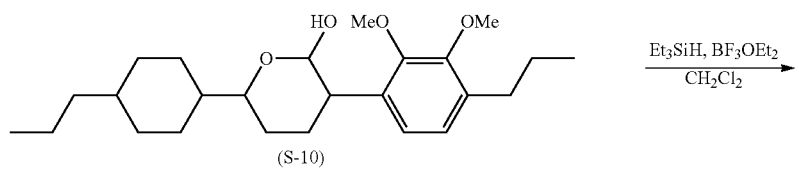

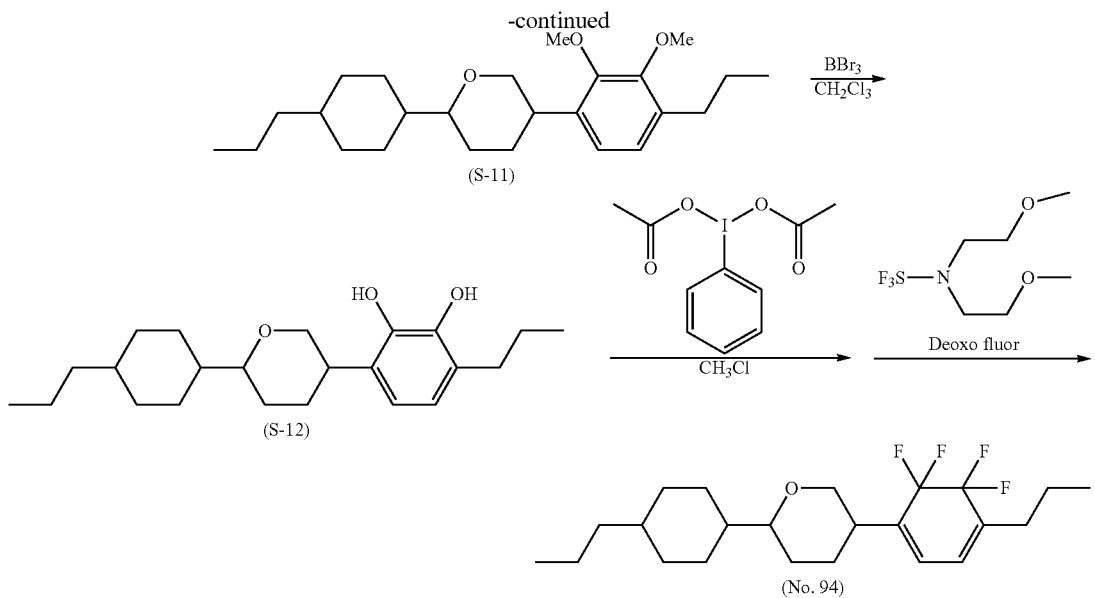

First Step

A solution of 1.66 M n-butyllithium in n-hexane (76 ml) was dropped to a solution of a compound (S-7) (20 g) synthesized by a general method in THF (200 ml) at −5° C. in a reaction vessel under a nitrogen atmosphere. Then, the reaction solution was returned to room temperature and stirred for 30 minutes. Then, the solution was cooled to −65° C., and a solution of a compound (S-8) (20.4 g) in tetrahydrofuran (30 ml) and boron trifluoride diethyl ether complex (15.9 g) were dropped to the solution. The reaction solution was returned to room temperature and allowed to react for 3 hours. The reaction solution was subjected to liquid separation through addition of an aqueous solution of 10% formic acid (100 ml). The aqueous layer was extracted with toluene (20 ml) three times, and the combined organic layers were washed with water and dried with anhydrous magnesium sulfate. The solvent was distilled off under reduced pressure. The residue was purified by silica gel column chromatography (silica gel: 50 g, eluent: heptane:ethyl acetate=80:20 (in terms of a volume ratio)) to provide a compound (S-9) (23.8 g; 59%).

Second Step

A solution of 0.99 M diisobutylaluminum hydride in toluene (60 ml) was dropped to a solution of the compound (S-9) (23.8 g) obtained in the above-mentioned step in tetrahydrofuran (100 ml) at −50° C. or less in a reaction vessel under a nitrogen atmosphere and the mixture was subjected to a reaction for 3 hours. The reaction solution was poured into an aqueous solution of 10% formic acid (50 ml) to be subjected to liquid separation. The aqueous layer was extracted with toluene (100 ml) twice. The combined organic layers were washed with water and dried with anhydrous magnesium sulfate. The solvent was distilled off under reduced pressure to provide a compound (S-10) (23.6 g; 99%).

Third Step 6.2 g of triethylsilane and 7.3 g of boron trifluoride diethyl ether complex were dropped to a solution of the compound (S-10) (23.6 g) obtained in the above-mentioned step in dichloromethane (100 ml) at −30° C. under a nitrogen atmosphere. The resultant was returned to room temperature and stirred for 3 hours. Then, the resultant was subjected to liquid separation through addition of water (30 ml). The organic layer was washed with water and dried with anhydrous magnesium sulfate, and the solvent was distilled off under reduced pressure. The residue was purified by silica gel column chromatography (silica gel: 100 g, eluent: heptane/ethyl acetate=80/20 (in terms of a volume ratio)) and recrystallization (heptane:ethyl acetate=80:20 (in terms of a volume ratio)) to provide a compound (S-11) (6.7 g, yield: 29%).

Fourth Step

The compound (S-11) (6.56 g) obtained in the above-mentioned step and dichloromethane (20 ml) were loaded into a reaction vessel and cooled to −60° C. under a nitrogen atmosphere. Then, a solution of 1 M boron tribromide in dichloromethane (65 ml) was dropped to the resultant, and the resultant was returned to room temperature, followed by stirring overnight. The mixture was poured into ice water. The organic layer was fractionated, washed with a saturated aqueous solution of sodium bicarbonate and water, and dried with anhydrous magnesium sulfate. The solution was concentrated under reduced pressure, and the residue was purified by silica gel column chromatography (ethyl acetate: toluene=1:19 in terms of a volume ratio) to provide a compound (S-12) (5.35 g; 88%).

Fifth Step

The compound (S-12) (5.35 g) obtained in the above-mentioned step and chloroform (200 ml) were loaded into a reaction vessel and cooled to 0° C. under a nitrogen atmosphere. Iodobenzene diacetate (5 g) was added to the resultant, and the resultant was returned to room temperature, followed by stirring for 5 minutes. The reaction system was again cooled to 0° C., and Deoxo-fluor (30 g) was added to the reaction system. The resultant was stirred for 2 days while being returned to room temperature. The mixture was poured into ice water. The organic layer was fractionated, washed with a saturated aqueous solution of sodium bicarbonate and water, and dried with anhydrous magnesium sulfate. The solution was concentrated under reduced pressure, and the residue was purified by silica gel column chromatography (heptane:toluene=3:1 in terms of a volume ratio) to provide a compound (No. 94) (454 mg; 7.6%).

Chemical shift δ (ppm; CDCl$_3$): 6.54-6.53 (m, 1H), 6.06-6.03 (m, 1H), 4.06 (dq, 2H), 3.42 (t, 1H), 3.10 (dq, 1H), 2.84 (t, 1H), 2.18 (t, 2H), 2.09 (d, 1H), 1.97 (d, 1H), 1.81-1.72 (m, 5H), 1.57-1.45 (m, 4H), 1.35-1.29 (m, 3H), 1.22-1.11 (m, 3H), 1.05 (sex, 1H), 0.95-0.81 (m, 2H), 0.87 (t, 3H), 0.85 (t, 3H).

The physical properties of the compound (No. 94) were as described below.

Optical anisotropy (Δn)=0.087; dielectric anisotropy (Δ∈)=−7.66.

Example 4

Synthesis of Compound (No. 76)

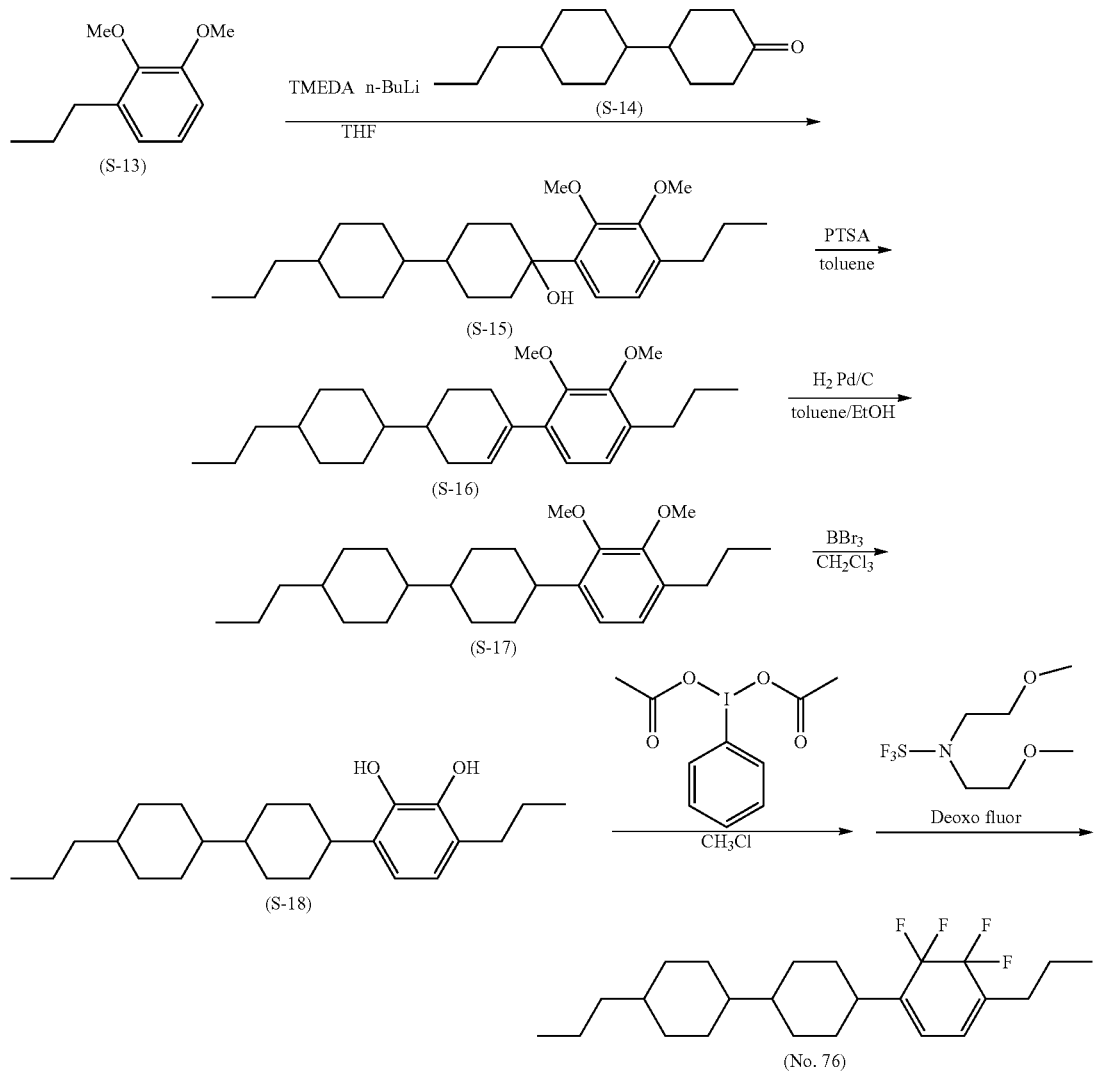

First Step

A compound (S-13) (20 g) synthesized by a general method, tetramethylethylenediamine (TMEDA: 19.34 g), and THF (200 ml) were loaded into a reaction vessel and cooled to 0° C. under a nitrogen atmosphere. A 1.6 M n-hexane solution (103 ml) was dropped to the reaction solution, and the resultant was returned to room temperature, followed by stirring for 2 hours. Then, the resultant was cooled to −60° C., and a solution of a compound (S-14) (32 g) in THF (50 ml) was dropped to the resultant. The mixture was stirred while being returned to room temperature for 2 hours. The reaction mixture was poured into water, and the aqueous layer was extracted with toluene. The organic layer was fractionated, washed with a saturated aqueous solution of sodium bicarbonate and water, and dried with anhydrous magnesium sulfate. The solution was concentrated under reduced pressure, and the residue was purified by silica gel column chromatography (toluene) to provide a compound (S-15) (37.9 g; 85%).

Second Step

The compound (S-15) (37.9 g) obtained in the above-mentioned step, p-toluenesulfonic acid (3 g), and toluene (300 ml) were loaded into a vessel, and the mixture was heated to reflux for 2 hours while distilled water was removed. The reaction mixture was cooled to 30° C., and water (500 ml) and toluene (500 ml) were added to be mixed with the obtained solution. The resultant was allowed to stand still so as to be separated into two layers: an organic layer and a aqueous layer. The organic layer was subjected to extraction treatment. The obtained organic layer was fractionated, washed with a saturated aqueous solution of sodium bicarbonate and water, and dried with anhydrous magnesium sulfate. The solution was concentrated under reduced pressure, and the residue was purified by silica gel column chromatography (toluene) to provide a compound (S-16) (35.4 g; 98%).

Third Step

The compound (S-16) (35.4 g) obtained in the above-mentioned step was dissolved in a mixed solvent of toluene (150 ml) and ethanol (150 ml), and 5% Pd/C (0.5 g) was further added to the solution. The resultant was stirred at room temperature until the absorption of hydrogen stopped under a hydrogen atmosphere. After the completion of the reaction, the Pd/C was removed, and the solvent was further distilled off. Then, the residue was purified by silica gel column chromatography (heptane) to provide a compound (S-17) (32.9 g; 94%).

Fourth Step

The compound (S-17) (32.9 g) obtained in the above-mentioned step and dichloromethane (200 ml) were loaded into a reaction vessel and cooled to −60° C. under a nitrogen atmosphere. Then, a solution of 1 M boron tribromide in dichloromethane (300 ml) was dropped to the resultant, and the resultant was returned to room temperature, followed by stirring overnight. The mixture was poured into ice water. The organic layer was fractionated, washed with a saturated aqueous solution of sodium bicarbonate and water, and dried with anhydrous magnesium sulfate. The solution was concentrated under reduced pressure, and the residue was purified by silica gel column chromatography (ethyl acetate:toluene=1:19 in terms of a volume ratio) to provide a compound (S-18) (26.8 g; 88%).

Fifth Step

The compound (S-18) (32.9 g) obtained in the above-mentioned step and chloroform (400 ml) were loaded into a reaction vessel and cooled to 0° C. under a nitrogen atmosphere. Iodobenzene diacetate (25 g) was added to the resultant, and the resultant was returned to room temperature, followed by stirring for 5 minutes. The reaction system was again cooled to 0° C., and Deoxo-fluor (60 g) was added to the reaction system. The resultant was stirred for 2 days while being returned to room temperature. The mixture was poured into ice water. The organic layer was fractionated, washed with a saturated aqueous solution of sodium bicarbonate and water, and dried with anhydrous magnesium sulfate. The solution was concentrated under reduced pressure, and the residue was purified by silica gel column chromatography (heptane:toluene=3:1 in terms of a volume ratio) to provide a compound (No. 76) (2.2 g; 7.4%).

Chemical shift δ (ppm; CDCl$_3$): 6.53-6.52 (m, 1H), 6.07-6.04 (m, 1H), 2.18 (t, 1H), 2.12 (quint, 1H), 1.73-1.24 (m, 26H), 0.87 (t, 3H), 0.85 (t, 3H).

The physical properties of the compound (No. 76) were as described below.

Optical anisotropy (Δn)=0.082; dielectric anisotropy (Δ∈)=−4.94.

Example 5

Synthesis of Compound (No. 162)

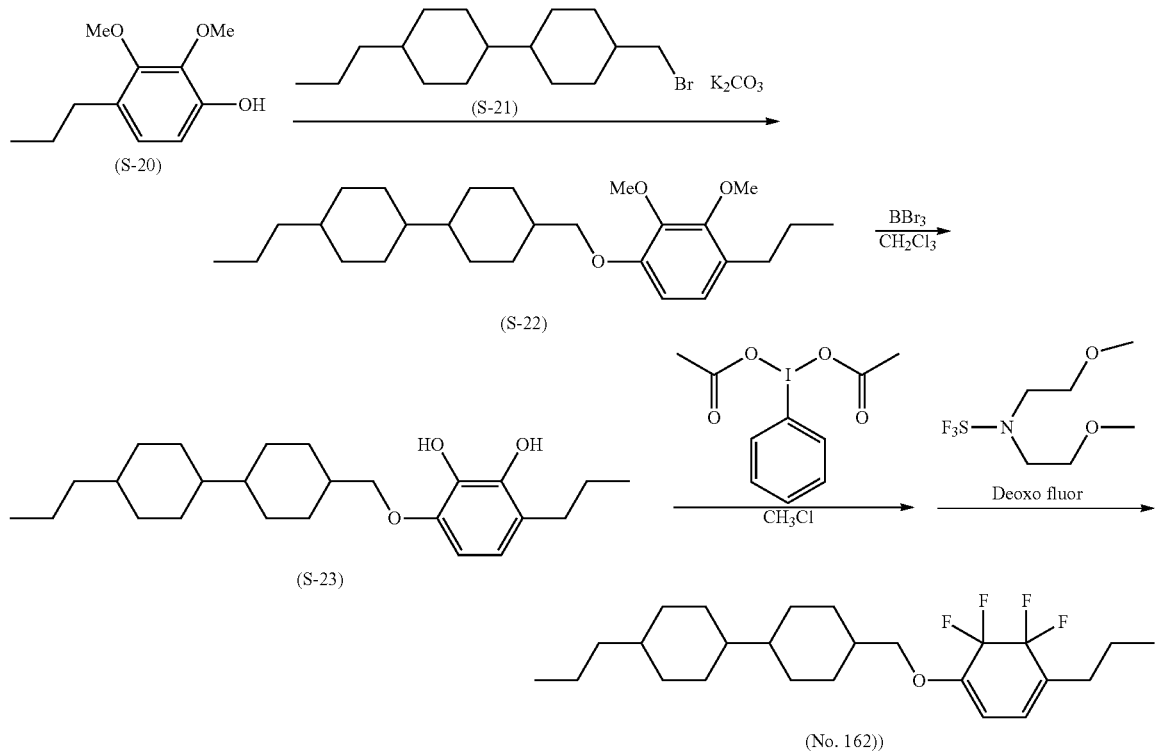

First Step

Compounds (S-20) (9.8 g) and (S-21) (15.1 g) synthesized by a general method and potassium carbonate (10.3 g) were loaded into a reaction vessel and stirred at 70° C. for 5 hours under a nitrogen atmosphere. Toluene (70 ml) and water (100 ml) were added to be mixed with the obtained reaction solution. The organic layer was fractionated, washed with saline, and dried with anhydrous magnesium sulfate. The solution was concentrated under reduced pressure, and the residue was purified by silica gel column chromatography (toluene) to provide a compound (S-22) (14.62 g; 70%).

Second Step

The compound (S-22) (14.62 g) obtained in the above-mentioned step and dichloromethane (100 ml) were loaded into a reaction vessel and cooled to −60° C. under a nitrogen atmosphere. Then, a solution of 1 M boron tribromide in dichloromethane (150 ml) was dropped to the resultant, and the resultant was returned to room temperature, followed by stirring overnight. The mixture was poured into ice water. The organic layer was fractionated, washed with a saturated aqueous solution of sodium bicarbonate and water, and dried with anhydrous magnesium sulfate. The solution was concentrated under reduced pressure, and the residue was purified by silica gel column chromatography (ethyl acetate:toluene=1:19 in terms of a volume ratio) to provide a compound (S-23) (10.9 g; 80%).

Third Step

The compound (S-23) (10.9 g) obtained in the above-mentioned step and chloroform (100 ml) were loaded into a reaction vessel and cooled to 0° C. under a nitrogen atmosphere. Iodobenzene diacetate (8.99 g) was added to the resultant, and the resultant was returned to room temperature, followed by stirring for 5 minutes. The reaction system was again cooled to 0° C., and Deoxo-fluor (25 g) was added to the reaction system. The resultant was stirred for 2 days while being returned to room temperature. The mixture was poured into ice water. The organic layer was fractionated, washed with a saturated aqueous solution of sodium bicarbonate and water, and dried with anhydrous magnesium sulfate. The solution was concentrated under reduced pressure, and the residue was purified by silica gel column chromatography (heptane:toluene=3:1 in terms of a volume ratio) to provide a compound (No. 162) (0.6 g; 5%).

Chemical shift δ (ppm; CDCl$_3$): 6.53-6.52 (m, 1H), 5.57-5.54 (m, 1H), 3.74 (d, 2H), 2.18 (t, 2H), 1.70-1.78 (m, 1H), 1.61-1.23 (m, 25H), 0.86 (t, 3H), 0.84 (t, 3H).

The physical properties of the compound (No. 162) were as described below.

Optical anisotropy (Δn)=0.093; dielectric anisotropy (Δ∈)=−6.30.

Example 6

Synthesis of Compound (No. 136)

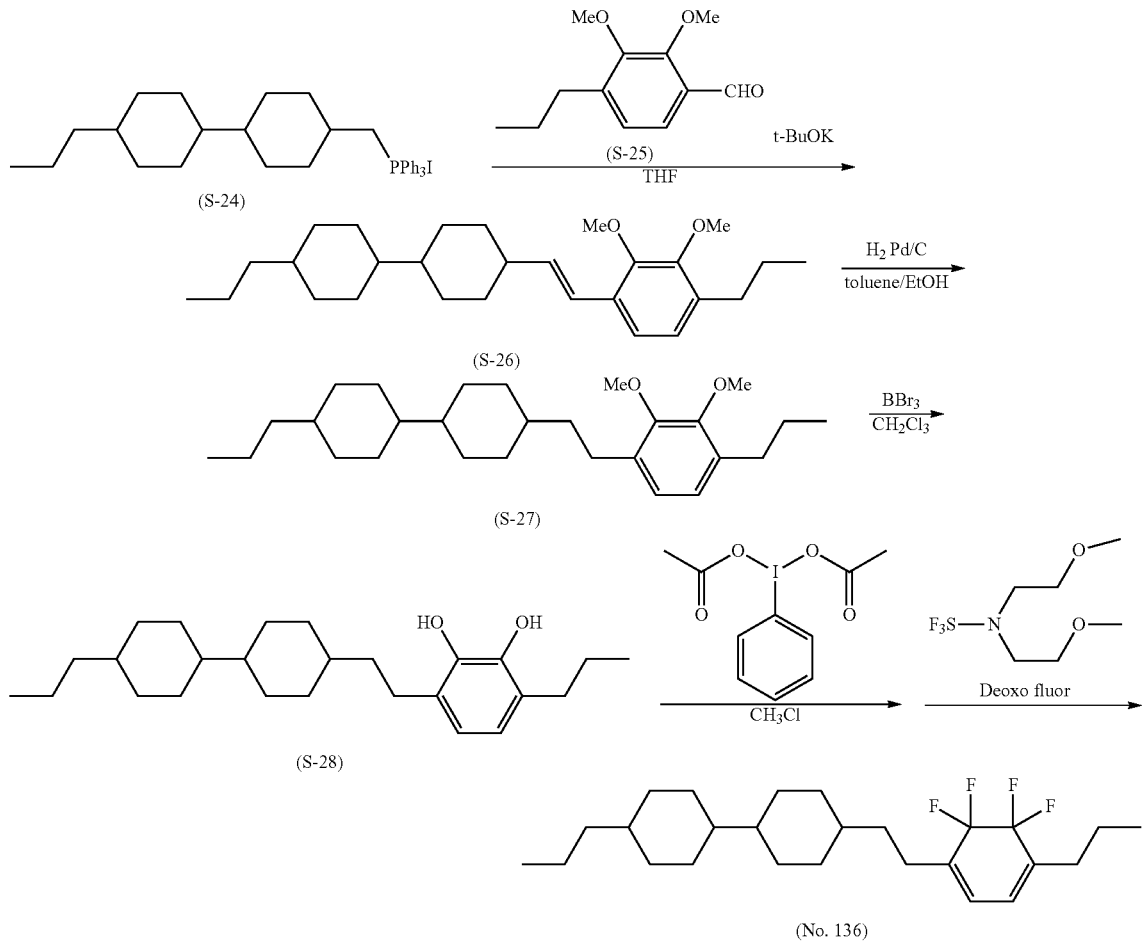

First Step

A compound (S-24) (16.4 g) synthesized by a general method and THF (100 ml) were mixed and cooled to −10° C. under a nitrogen atmosphere. Then, potassium t-butoxide (3.4 g) was loaded into the resultant in two portions within a temperature range of from −10° C. to −5° C. The resultant was stirred at −10° C. for 60 minutes, and a solution of a compound (S-25) (5.6 g) synthesized by a general method in THF (30 ml) was dropped to the resultant within a temperature range of from −10° C. to −5° C. The resultant was stirred at 0° C. for 30 minutes, and the reaction solution was poured to be mixed with a mixed solution of water (100 ml) and toluene (200 ml). The organic layer was fractionated, washed with saline, and dried with anhydrous magnesium sulfate. The solution was concentrated under reduced pressure, and the residue was purified by silica gel column chromatography (toluene) to provide a compound (S-26) (8.9 g; 80%).

Second Step

The compound (S-26) (8.9 g) obtained in the above-mentioned step was dissolved in a mixed solvent of toluene (150 ml) and ethanol (150 ml), and 5% Pd/C (0.5 g) was further added to the solution. Then, the resultant was stirred at room temperature until the absorption of hydrogen stopped under a hydrogen atmosphere. After the completion of the reaction, the Pd/C was removed, and the solvent was further distilled off. Then, the residue was purified by silica gel column chromatography (heptane) to provide a compound (S-27) (8.1 g: 90%).

Third Step

The compound (S-27) (8.1 g) obtained in the above-mentioned step and dichloromethane (100 ml) were loaded into a reaction vessel and cooled to −60° C. under a nitrogen atmosphere. Then, a solution of 1 M boron tribromide in dichloromethane (80 ml) was dropped to the resultant, and the resultant was returned to room temperature, followed by stirring overnight. The mixture was poured into ice water. The organic layer was fractionated, washed with a saturated aqueous solution of sodium bicarbonate and water, and dried with anhydrous magnesium sulfate. The solution was concentrated under reduced pressure, and the residue was purified by silica gel column chromatography (ethyl acetate:toluene=1:19 in terms of a volume ratio) to provide a compound (S-28) (6.79 g; 90%).

Fourth Step

The compound (S-28) (6.79 g) obtained in the above-mentioned step and chloroform (100 ml) were loaded into a reaction vessel and cooled to 0° C. under a nitrogen atmosphere. Iodobenzene diacetate (5.63 g) was added to the resultant, and the resultant was returned to room temperature, followed by stirring for 5 minutes. The reaction system was again cooled to 0° C., and Deoxo-fluor (15 g) was added to the reaction system. The resultant was stirred for 2 days while being returned to room temperature. The mixture was poured into ice water. The organic layer was fractionated, washed with a saturated aqueous solution of sodium bicarbonate and water, and dried with anhydrous magnesium sulfate. The solution was concentrated under reduced pressure, and the residue was purified by silica gel column chromatography (heptane:toluene=3:1 in terms of a volume ratio) to provide a compound (No. 136) (0.74 g; 10.0%).

Chemical shift δ (ppm; CDCl$_3$): 5.70-5.68 (m, 1H), 5.83-5.81 (m, 1H), 2.20 (t, 2H), 2.18 (t, 2H), 1.61-1.23 (m, 28H), 0.85 (t, 3H), 0.82 (t, 3H)

The physical properties of the compound (No. 136) were as described below.

Optical anisotropy (Δn)=0.077; dielectric anisotropy (Δ∈)=−4.54

Example 22

A compound (No. 226) was obtained by using a compound (S-29) instead of the compound (S-1) in Example 1.

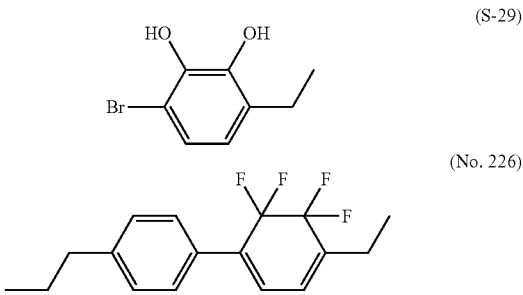

Chemical shift δ (ppm; CDCl$_3$): 7.40 (d, 2H), 7.22 (d, 2H), 6.33 (d, 1H), 6.08 (d, 1H), 2.63 (t, 2H), 2.39 (q, 2H), 1.68 (sex, 2H), 1.20 (t, 3H), 0.98 (t, 3H).

The physical properties of the compound (No. 226) were as described below.

Transition temperature: C 12.1 N 15.3 I.

Maximum temperature (T$_{NI}$)=−63.4° C.; optical anisotropy (Δn)=0.094; dielectric anisotropy (Δ∈)=−4.43; viscosity (η)=41.1 mPa·s.

Example 23

A compound (No. 227) was obtained by using a compound (S-29) instead of the compound (S-1) in Example 2.

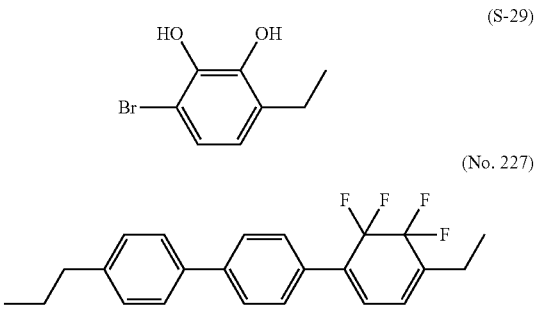

Chemical shift δ (ppm; CDCl$_3$): 7.61 (d, 2H), 7.53 (d, 2H), 7.53 (d, 2H), 7.27 (d, 2H), 6.39 (d, 1H), 6.09 (d, 1H), 2.63 (t, 2H), 2.40 (q, 2H), 1.68 (sex, 2H), 1.19 (t, 3H), 0.98 (t, 3H).

The physical properties of the compound (No. 227) were as described below.

Transition temperature: C 108.0 N 113.3 I.

Maximum temperature (T$_{NI}$)=101.3° C.; optical anisotropy (Δn)=0.260; dielectric anisotropy (Δ∈)=−5.05; viscosity (η)=87.1 mPa·s.

Example 23

A compound (No. 229) was obtained by using a compound (S-30) instead of the compound (S-25) in Example 6.

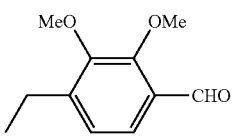
(S-30)

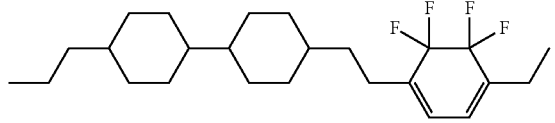
(No. 229)

Chemical shift δ (ppm; CDCl$_3$): 5.88 (s, 2H), 2.32-2.21 (m, 4H), 1.81-1.65 (m, 8H), 1.40-0.75 (m, 18H), 1.15 (t, 3H), 0.88 (t, 3H).

The physical properties of the compound (No. 229) were as described below.

Transition temperature: C 141.5 I.

Maximum temperature (T$_{NI}$)=109.3° C.; optical anisotropy (Δn)=0.087; dielectric anisotropy (Δ∈)=−5.11; viscosity (η)=197.5 mPa·s; light resistance 15% of the compound (No. 229) was added to a base liquid crystal ZLI-1132 (manufactured by Merck Ltd.), and a change in clearing point of the composition before and after the UV ray irradiation was measured to be within 5° C.

Example 24

A compound (No. 228) was obtained by using a compound (S-31) instead of the compound (S-3) in Example 7.

The compound (S-31) can be synthesized by a method described in Example 2 and the like of JP 2012-25667 A.

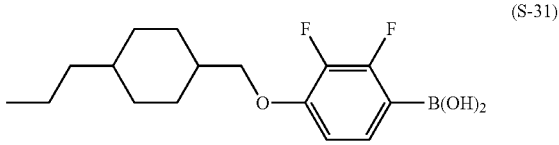
(S-31)

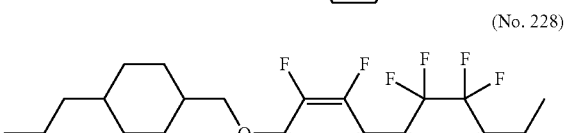
(No. 228)

Chemical shift δ (ppm; CDCl$_3$): 7.07 (t, 1H), 6.75 (t, 1H), 6.40 (d, 1H), 6.08 (d, 1H), 3.87 (d, 2H), 2.42 (q, 2H), 1.95 (d, 2H), 1.83 (d, 3H), 1.40-0.90 (m, 9H), 1.22 (t, 3H), 0.90 (t, 3H).

The physical properties of the compound (No. 228) were as described below.

Transition temperature: C 60.5 N 62.7 I.

Maximum temperature (T$_{NI}$)=63.3° C.; optical anisotropy (Δn)=0.140; dielectric anisotropy (Δ∈)=−8.12; viscosity (η)=253.6 mPa·s.

Compounds (No. 1) to (No. 229) described below can be synthesized in accordance with the synthesis method for the compound (1) described above and the synthesis procedures described in Examples 1 to 6.

| No. | |
|---|---|
| 1 | 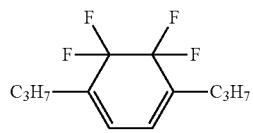 |
| 2 | 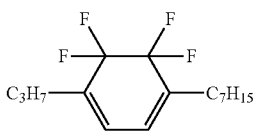 |
| 3 | 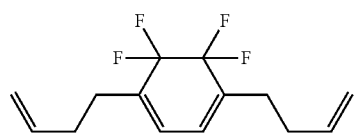 [SMILES: C=CCCC1=CC=C(CCC=C)C(F)(F)C1(F)F] |
| 4 | 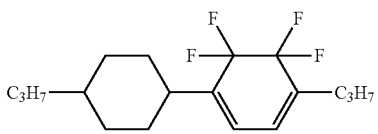 |
| 5 | 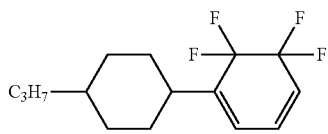 |

-continued
| No. | |
|---|---|
| 6 | 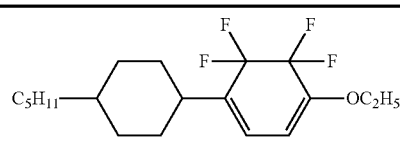 |
| 7 | 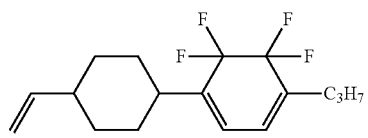 |
| 8 | 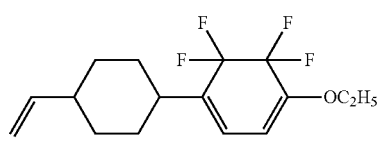 [SMILES: C=CC1CCC(C2=CC=C(OCC)C(F)(F)C2(F)F)CC1] |
| 9 | 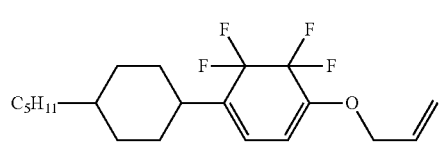 |
| 10 | 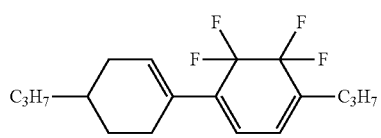 |
| 11 | 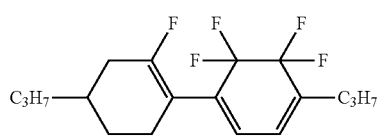 |
| 12 | 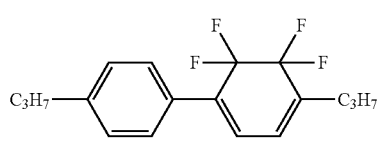 |
| 13 | 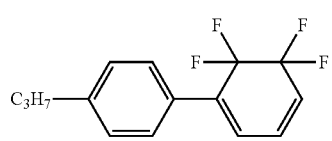 |
| 14 | 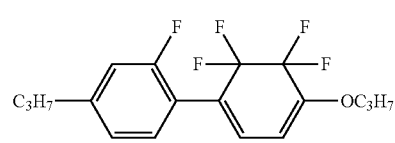 |
| 15 | 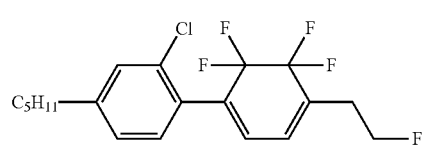 |
| 16 | 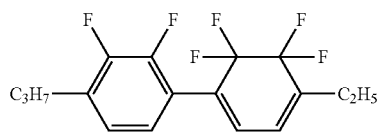 |

-continued
| No. | |
|---|---|
| 17 | 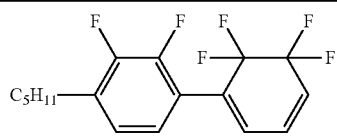 |
| 18 | 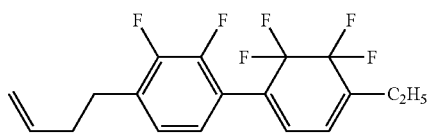 [SMILES: C=CCCc1ccc(C2=CC=C(CC)C(F)(F)C2(F)F)c(F)c1F] |
| 19 | 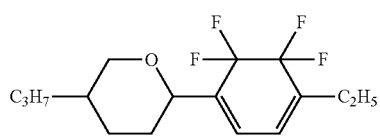 |
| 20 | 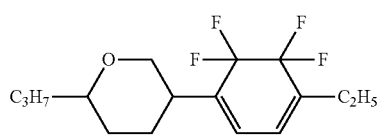 |
| 21 | 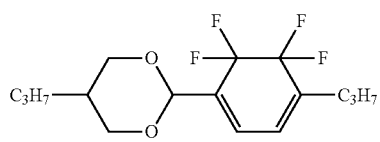 |
| 22 | 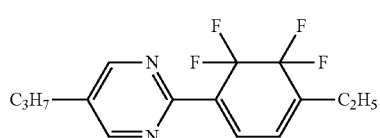 |
| 23 | 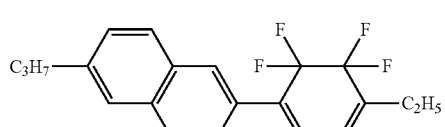 |
| 24 | 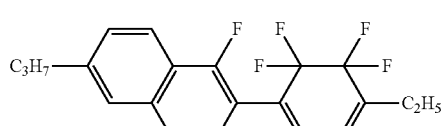 |
| 25 | 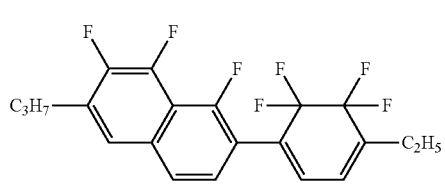 |
| 26 | 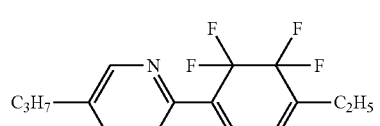 |
| 27 | 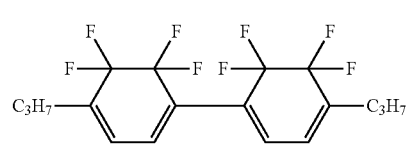 |

-continued
| No. | |
|---|---|
| 28 | 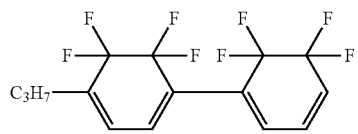 |
| 29 | 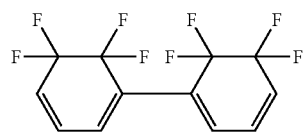 [SMILES: FC1(F)C=CC=C(C2=CC=CC(F)(F)C2(F)F)C1(F)F] |
| 30 | 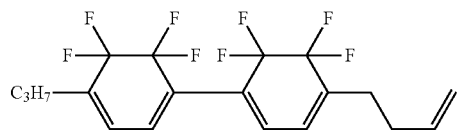 |
| 31 | 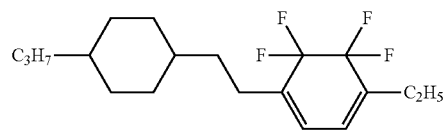 |
| 32 | 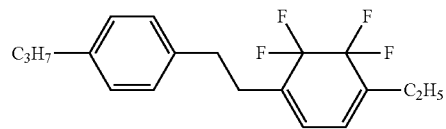 |
| 33 | 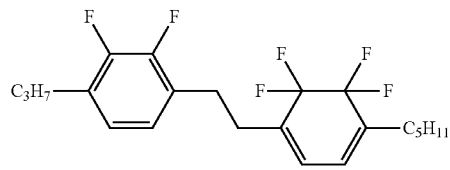 |
| 34 | 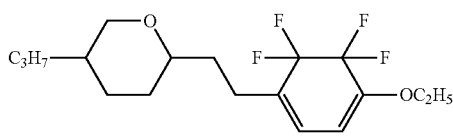 |
| 35 | 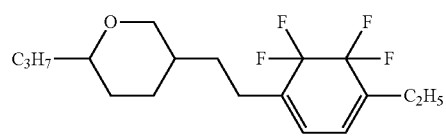 |
| 36 | 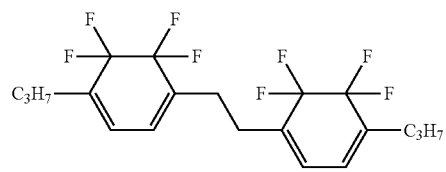 |
| 37 | 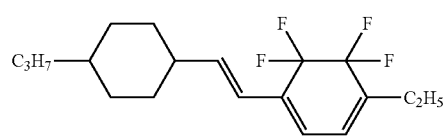 |

-continued
| No. | |
|---|---|
| 38 | 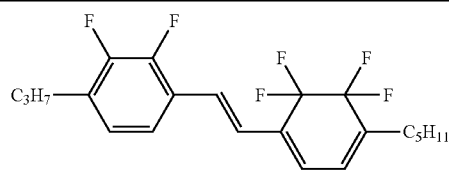 |
| 39 | 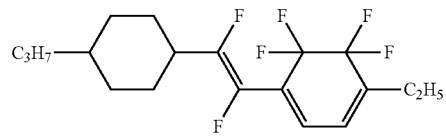 |
| 40 | 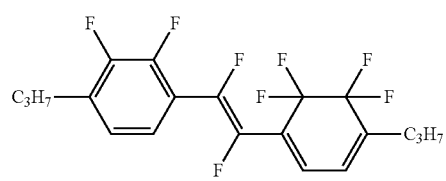 |
| 41 | 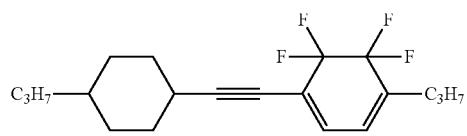 |
| 42 | 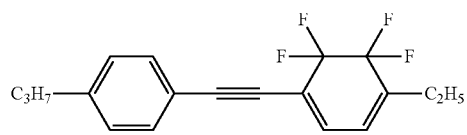 |
| 43 | 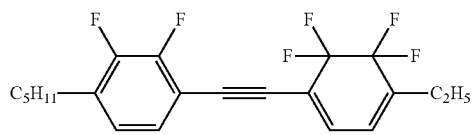 |
| 44 | 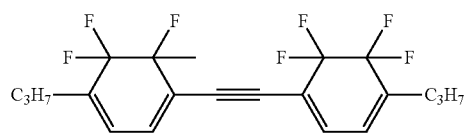 |
| 45 | 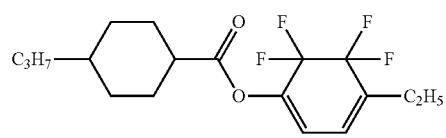 |
| 46 | 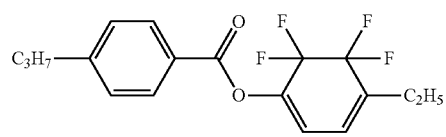 |
| 47 | 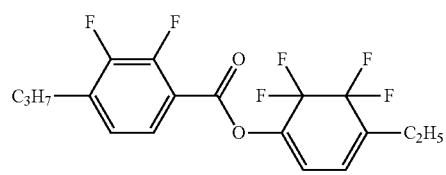 |

-continued
| No. | |
|---|---|
| 48 | 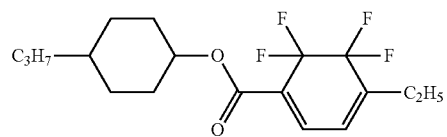 |
| 49 | 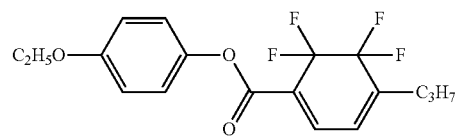 |
| 50 | 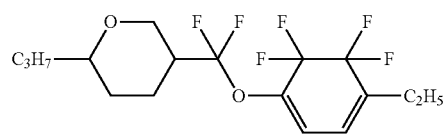 |
| 51 | 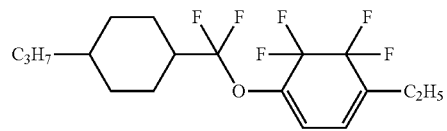 |
| 52 | 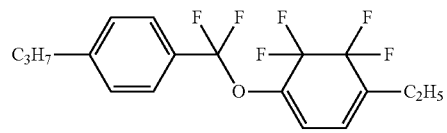 |
| 53 | 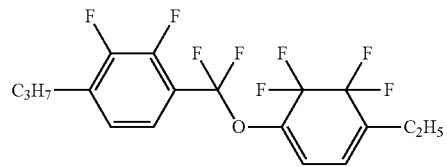 |
| 54 | 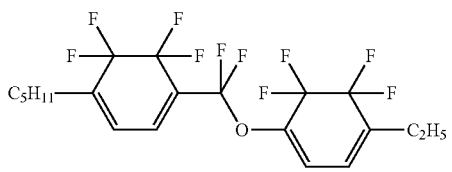 |
| 55 | 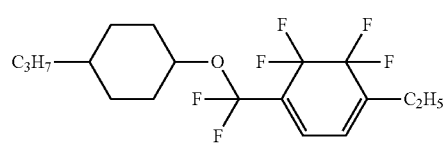 |
| 56 | 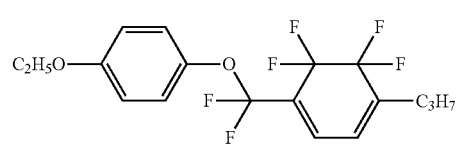 |
| 57 | 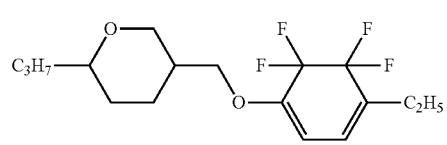 |

-continued
| No. | |
|---|---|
| 58 | 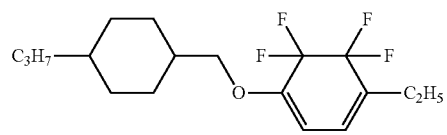 |
| 59 | 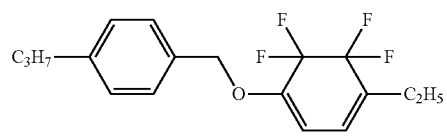 |
| 60 | 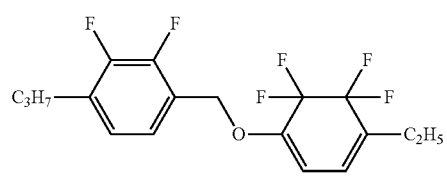 |
| 61 | 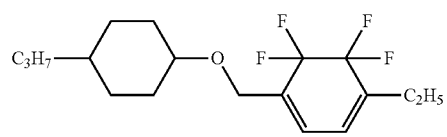 |
| 62 | 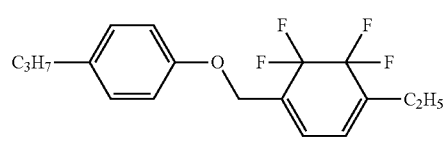 |
| 63 | 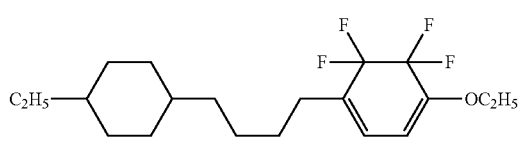 [SMILES: CCOC1=CC=C(CCCCC2CCC(CC)CC2)C(F)(F)C1(F)F] |
| 64 | 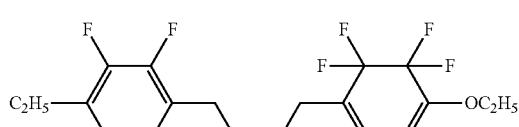 |
| 65 | 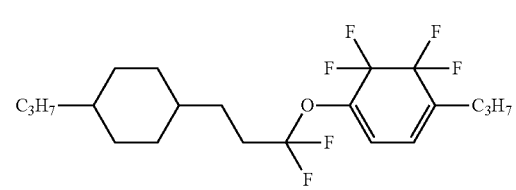 |
| 66 | 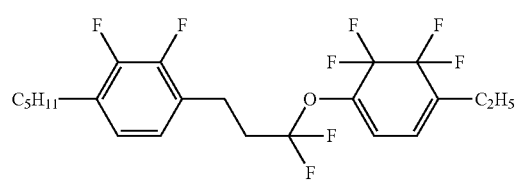 |
| 67 | 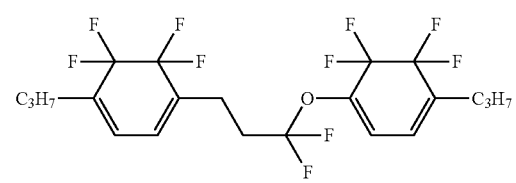 |

-continued
| No. | |
|---|---|
| 68 | 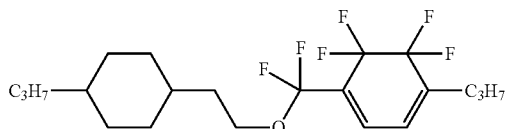 |
| 69 | 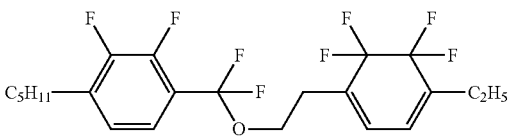 |
| 70 | 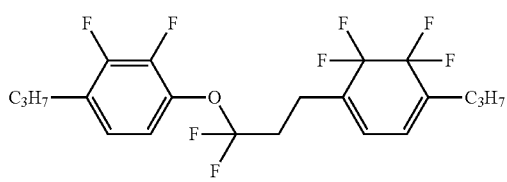 |
| 71 | 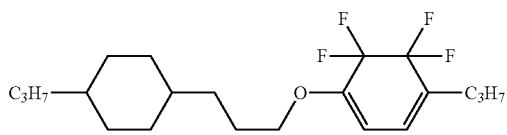 |
| 72 | 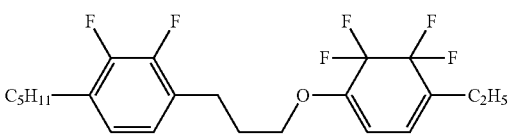 |
| 73 | 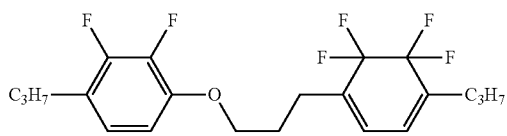 |
| 74 | 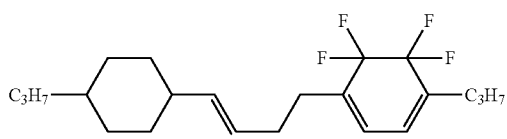 |
| 75 | 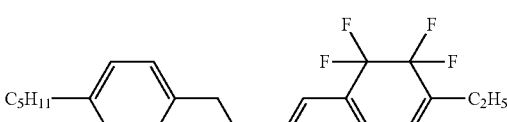 |
| 76 | 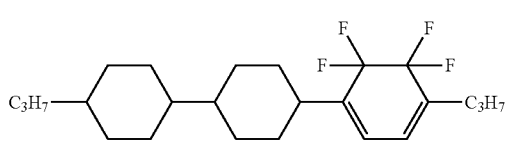 |
| 77 | 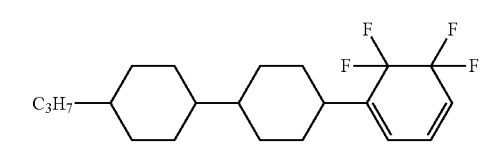 |
| 78 | 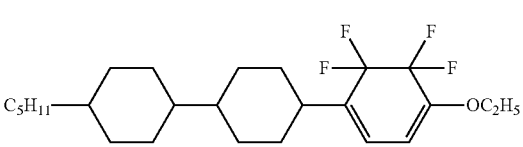 |

-continued
| No. | |
|---|---|
| 79 | 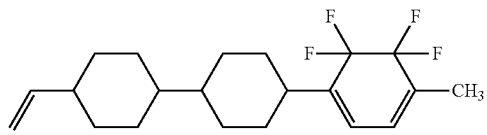 |
| 80 | 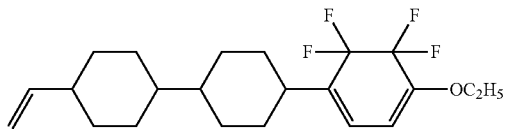 [SMILES: C=CC1CCC(C2CCC(C3=CC=C(OCC)C(F)(F)C3(F)F)CC2)CC1] |
| 81 | 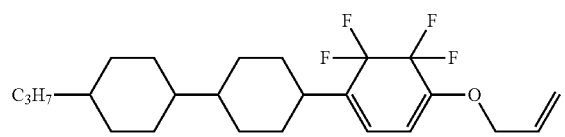 |
| 82 | 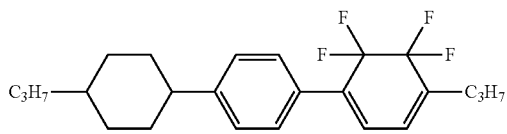 |
| 83 | 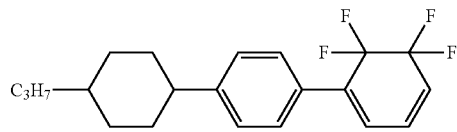 |
| 84 | 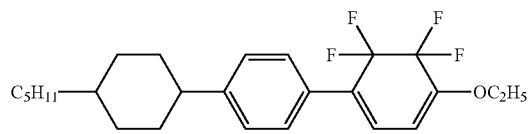 |
| 85 | 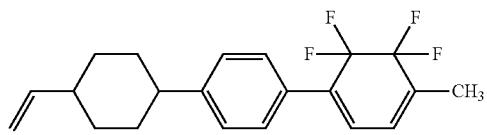 |
| 86 | 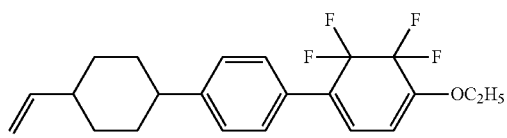 [SMILES: C=CC1CCC(c2ccc(C3=CC=C(OCC)C(F)(F)C3(F)F)cc2)CC1] |
| 87 | 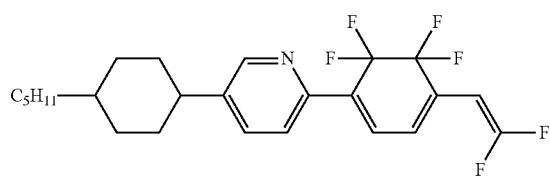 |
| 88 | 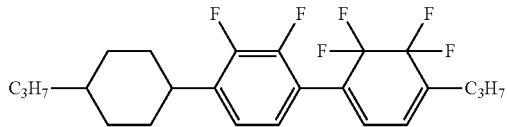 |

-continued
| No. | |
|---|---|
| 89 | 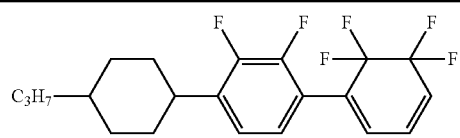 |
| 90 | 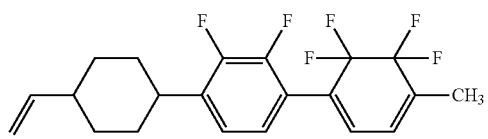 [SMILES: C=CC1CCC(c2ccc(C3=CC=C(C)C(F)(F)C3(F)F)c(F)c2F)CC1] |
| 91 | 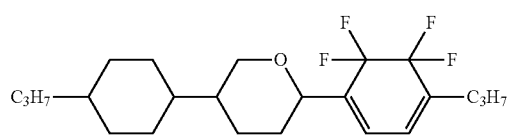 |
| 92 | 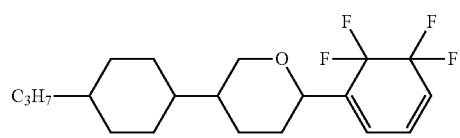 |
| 93 | 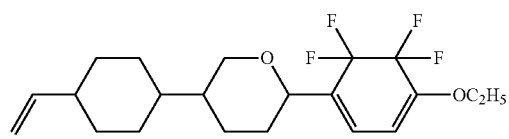 [SMILES: C=CC1CCC(C2CCC(C3=CC=C(OCC)C(F)(F)C3(F)F)OC2)CC1] |
| 94 | 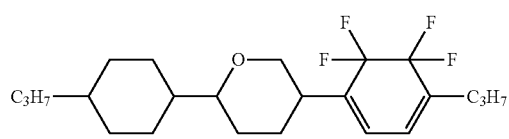 |
| 95 | 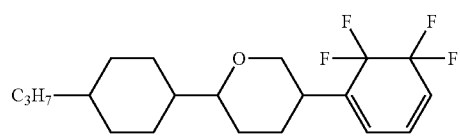 |
| 96 | 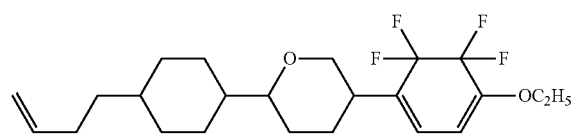 |
| 97 | 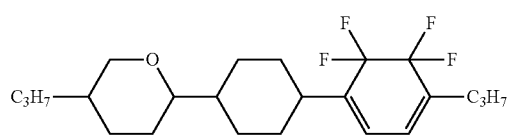 |
| 98 | 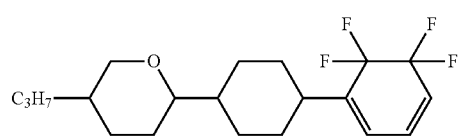 |
| 99 | 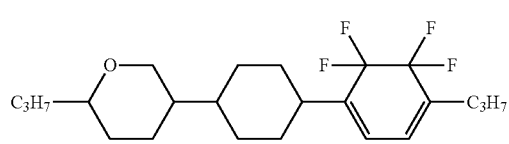 |

| No. | |
|---|---|
| 100 | 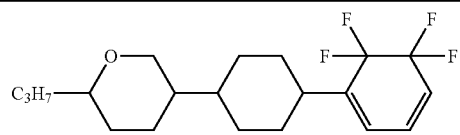 |
| 101 | 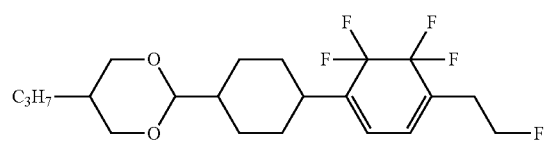 |
| 102 | 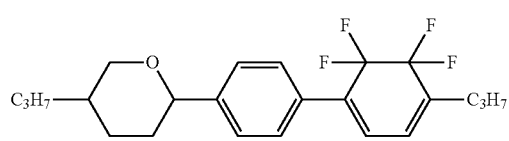 |
| 103 | 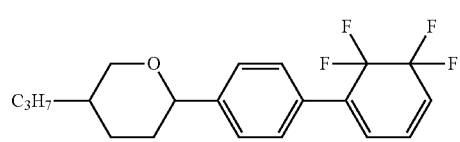 |
| 104 | 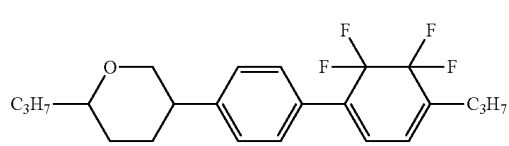 |
| 105 | 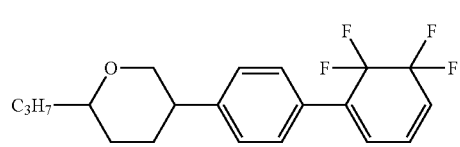 |
| 106 | 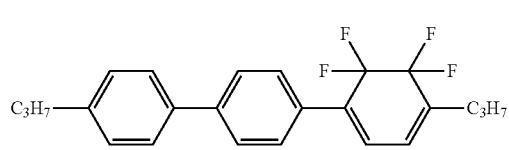 |
| 107 | 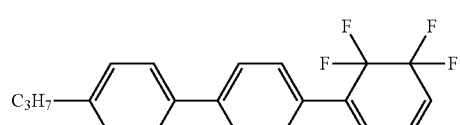 |
| 108 | 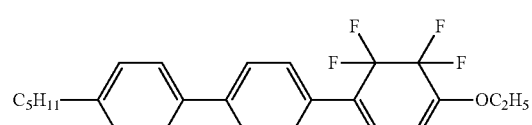 |
| 109 | 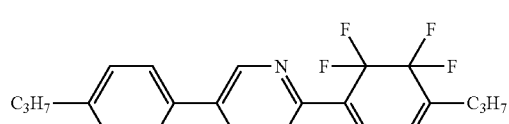 |
| 110 | 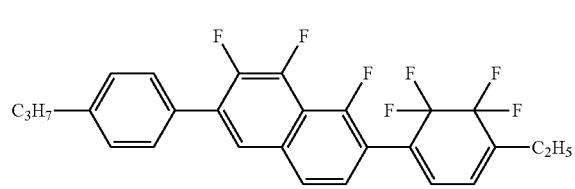 |

-continued
| No. | |
|---|---|
| 111 | 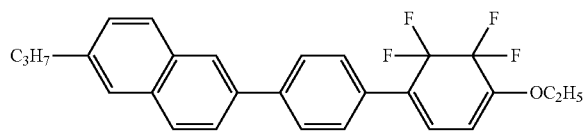 |
| 112 | 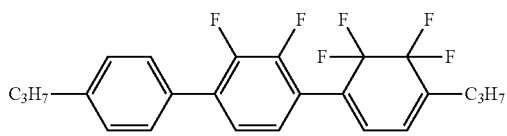 |
| 113 | 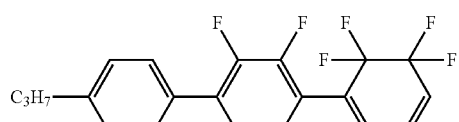 |
| 114 | 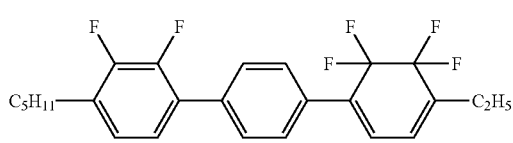 |
| 115 | 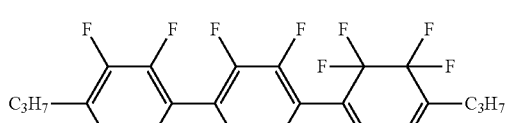 |
| 116 | 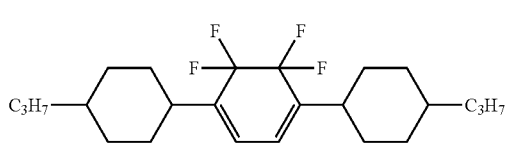 |
| 117 | 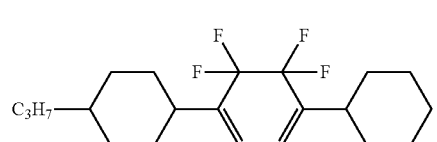 |
| 118 | 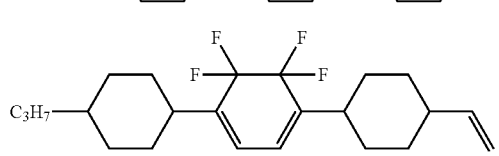 |
| 119 | 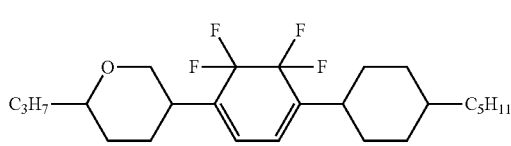 |
| 120 | 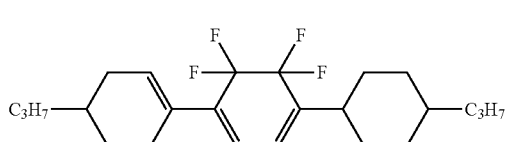 |
| 121 | 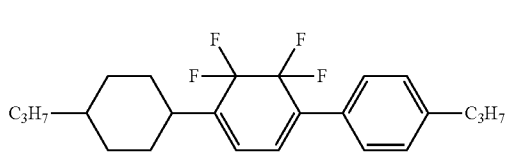 |

-continued
| No. | |
|---|---|
| 122 | 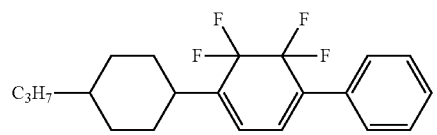 |
| 123 | 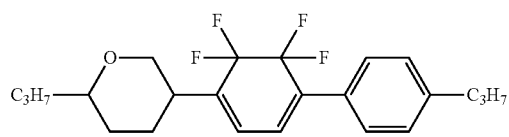 |
| 124 | 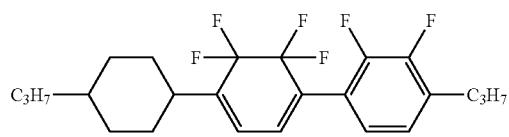 |
| 125 | 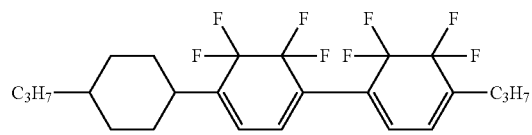 |
| 126 | 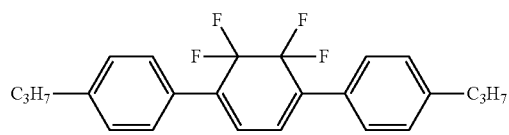 |
| 127 | 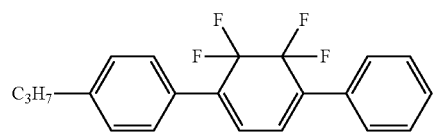 |
| 128 | 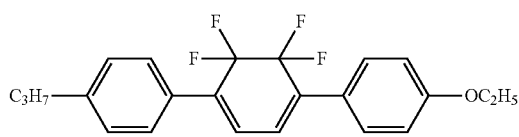 |
| 129 | 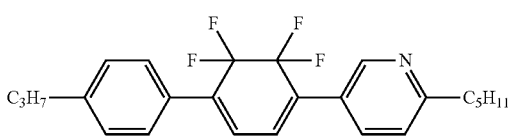 |
| 130 | 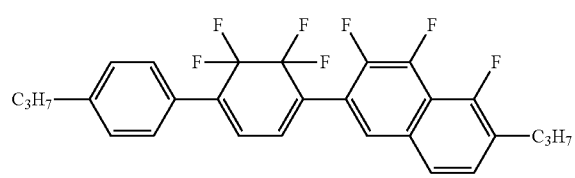 |
| 131 | 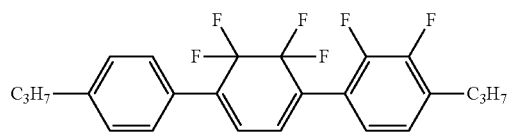 |
| 132 | 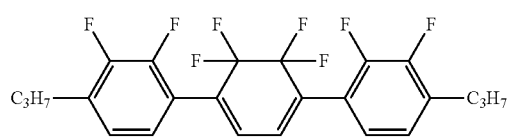 |

| No. | |
|---|---|
| 133 | 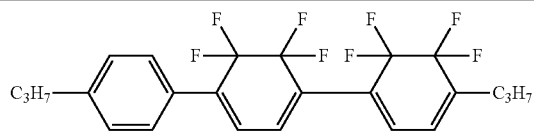 |
| 134 | 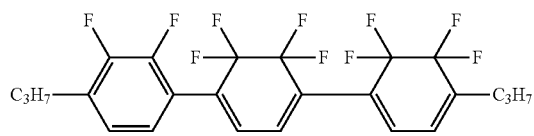 |
| 135 | 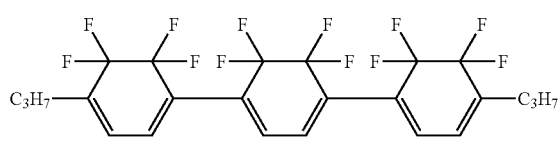 |
| 136 | 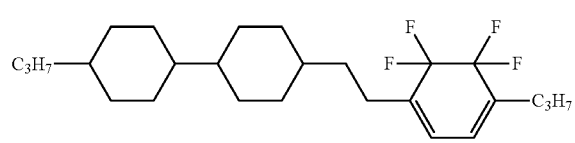 |
| 137 | 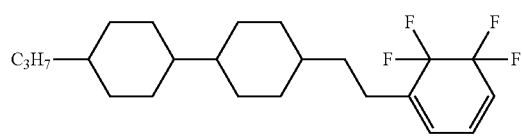 |
| 138 | 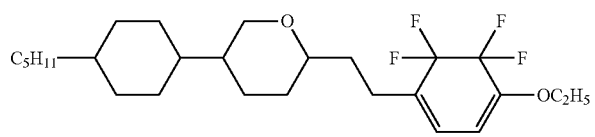 |
| 139 | 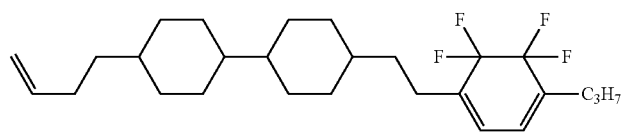 |
| 140 | 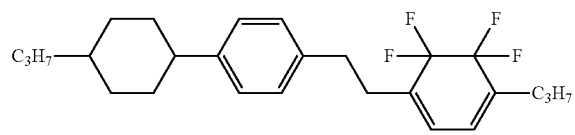 |
| 141 | 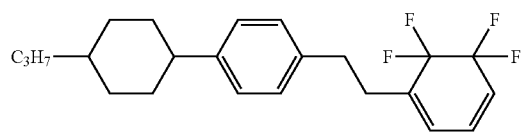 |
| 142 | 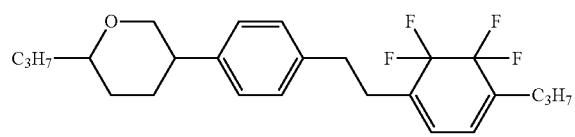 |
| 143 | 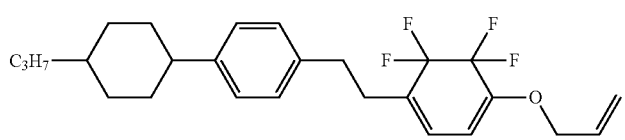 |

-continued
| No. | |
|---|---|
| 144 | 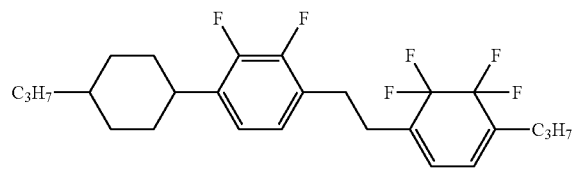 |
| 145 | 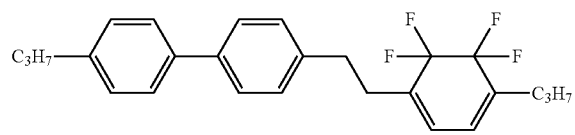 |
| 146 | 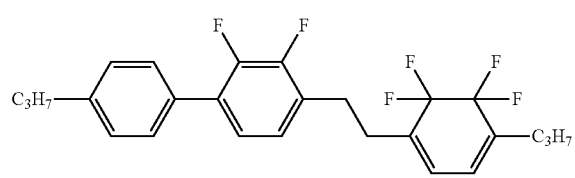 |
| 147 | 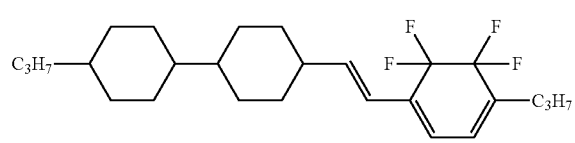 |
| 148 | 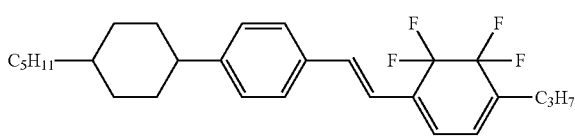 |
| 149 | 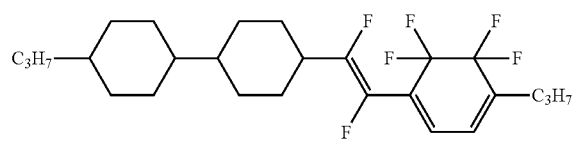 |
| 150 | 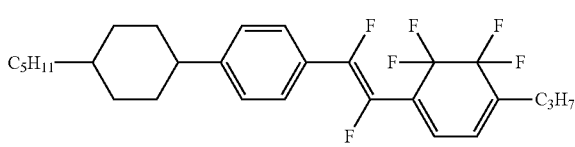 |
| 151 | 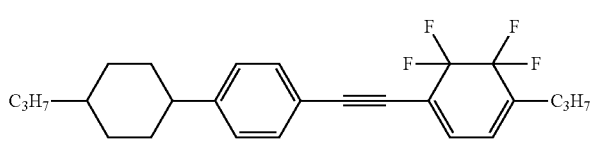 |
| 152 | 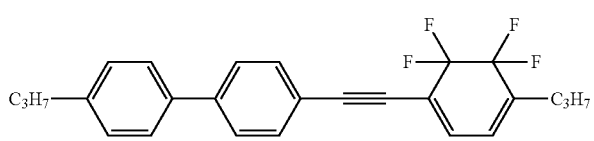 |
| 153 | 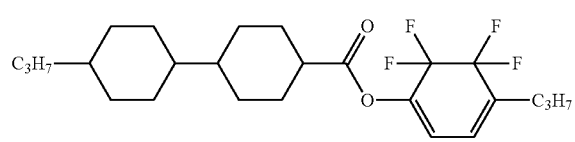 |

-continued
| No. | |
|---|---|
| 154 | 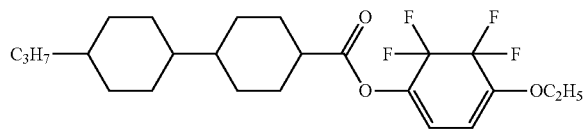 |
| 155 | 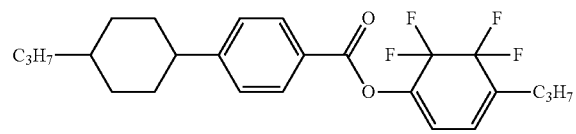 |
| 156 | 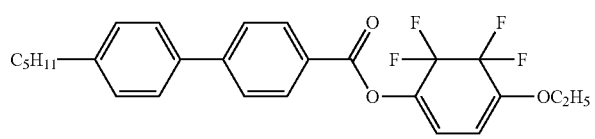 |
| 157 | 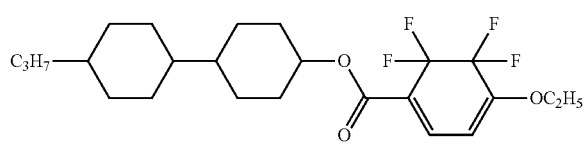 |
| 158 | 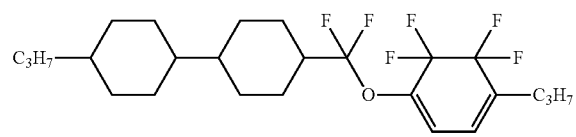 |
| 159 | 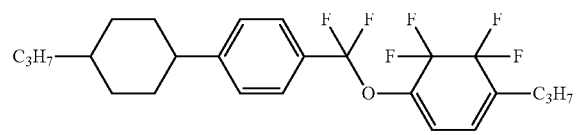 |
| 160 | 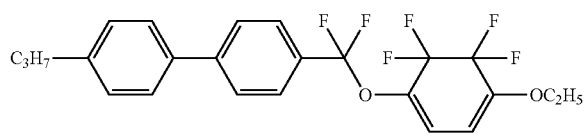 |
| 161 | 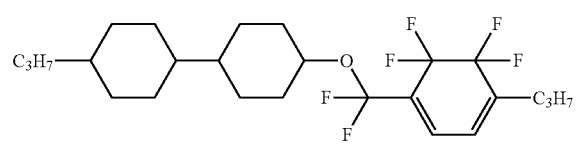 |
| 162 | 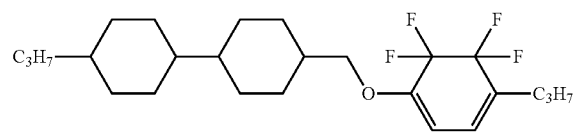 |
| 163 | 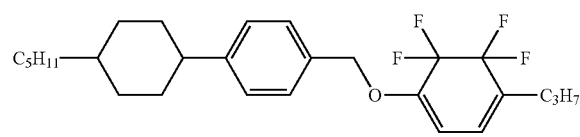 |
| 164 | 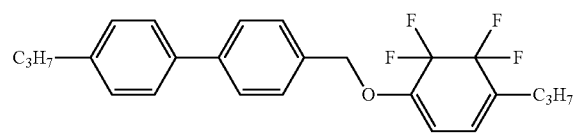 |

-continued
| No. | |
|---|---|
| 165 | 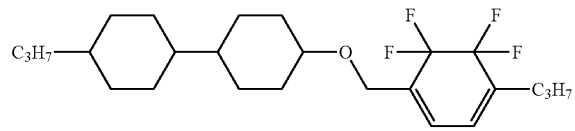 |
| 166 | 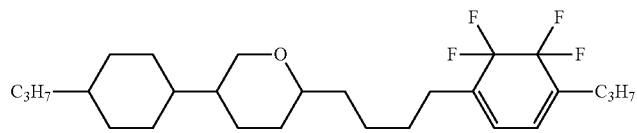 |
| 167 | 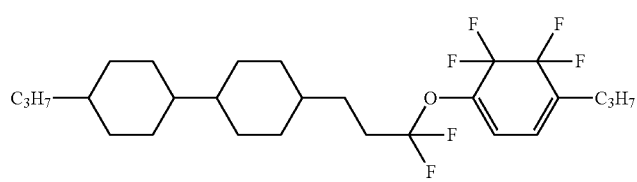 |
| 168 | 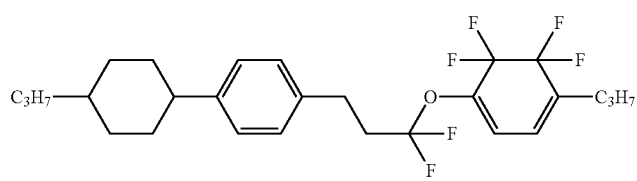 |
| 169 | 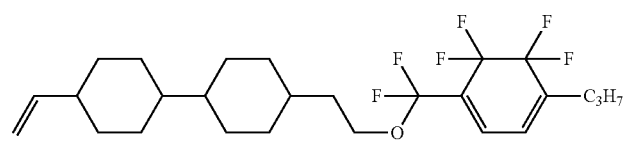 |
| 170 | 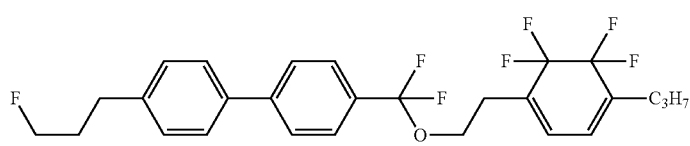 |
| 171 | 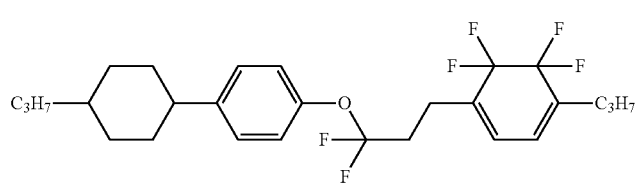 |
| 172 | 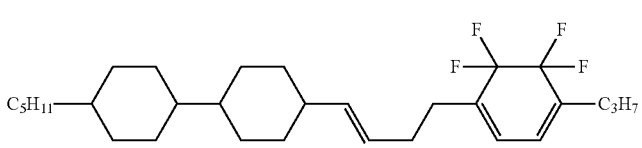 |
| 173 | 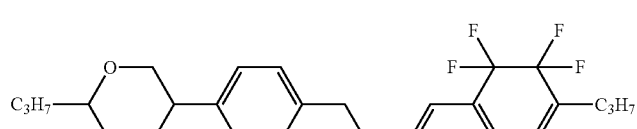 |
| 174 | 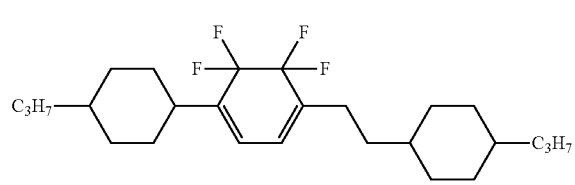 |

| No. | |
|---|---|
| 175 | 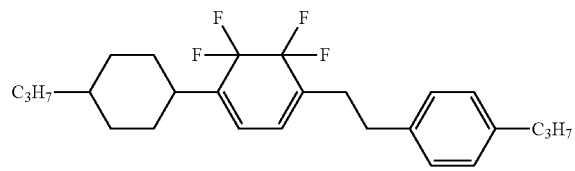 |
| 176 | 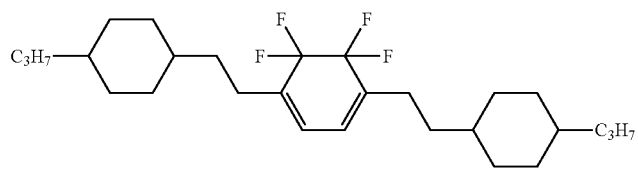 |
| 177 | 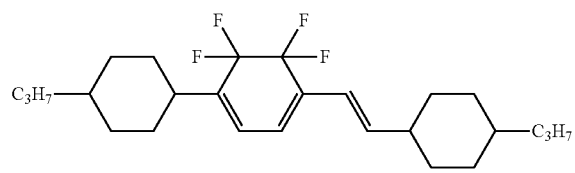 |
| 178 | 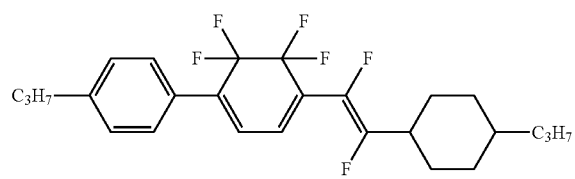 |
| 179 | 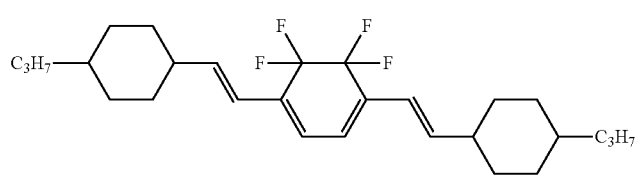 |
| 180 | 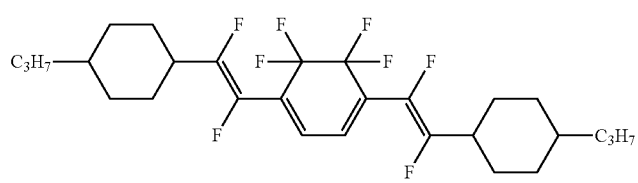 |
| 181 | 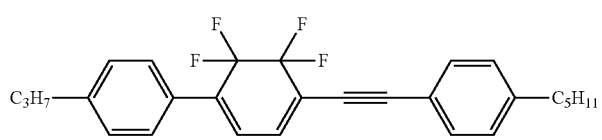 |
| 182 | 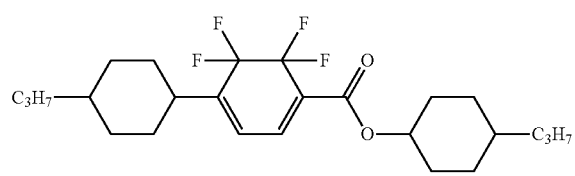 |
| 183 | 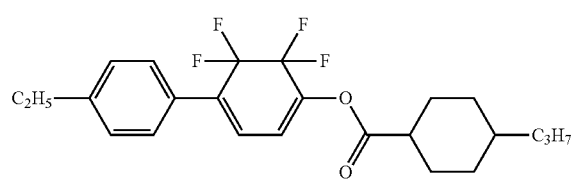 |

-continued
| No. | |
|---|---|
| 184 | 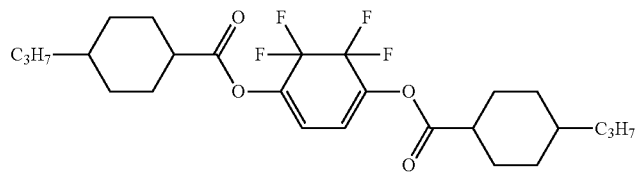 |
| 185 | 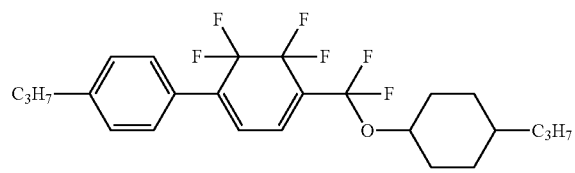 |
| 186 | 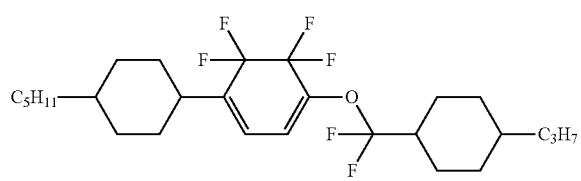 |
| 187 | 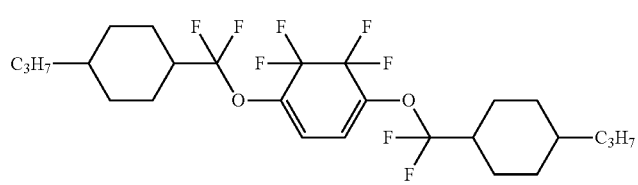 |
| 188 | 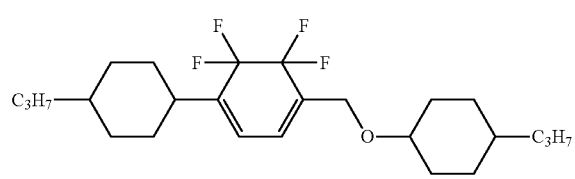 |
| 189 | 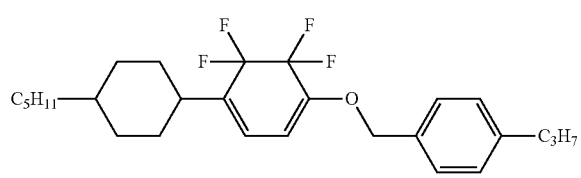 |
| 190 | 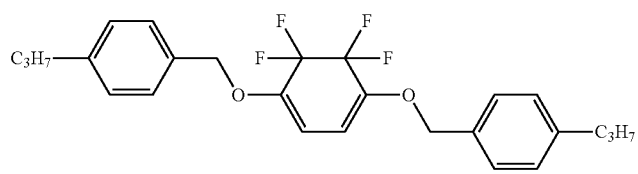 |
| 191 | 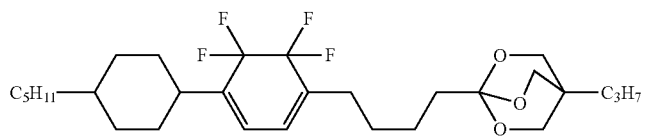 |
| 192 | 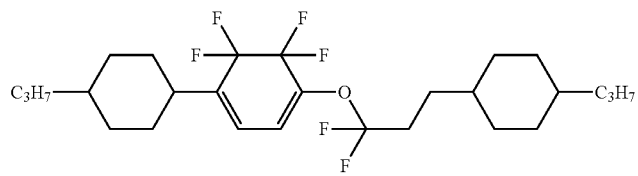 |

-continued
| No. | |
|---|---|
| 193 | 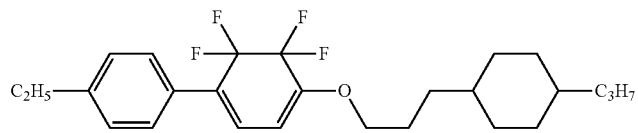 |
| 194 | 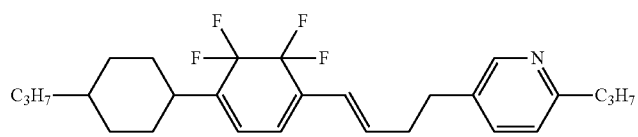 |
| 195 | 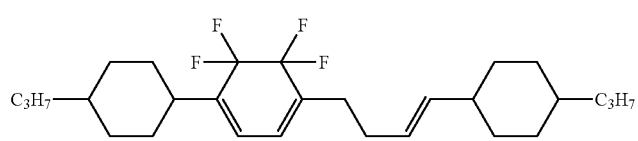 |
| 196 | 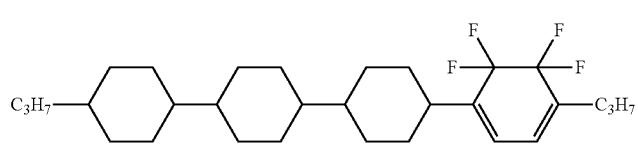 |
| 197 | 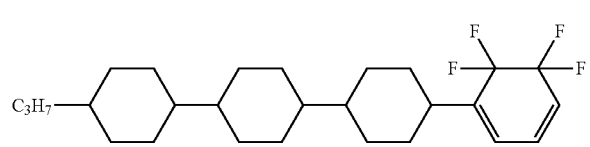 |
| 198 | 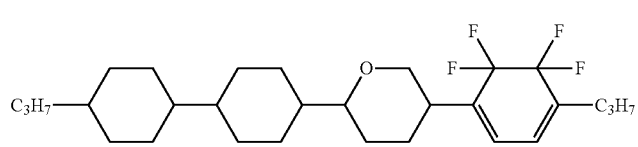 |
| 199 | 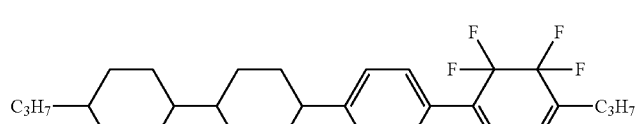 |
| 200 | 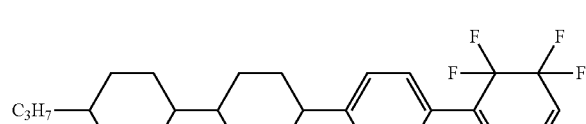 |
| 201 | 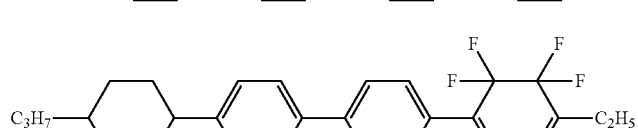 |
| 202 | 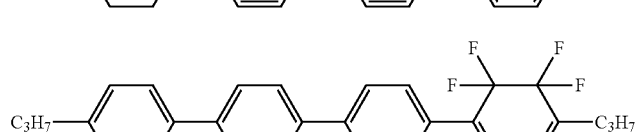 |
| 203 | 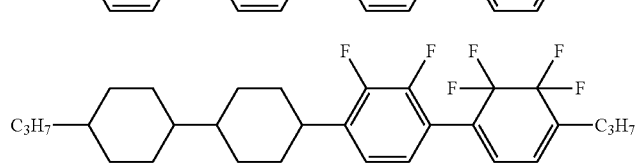 |

-continued
| No. | |
|---|---|
| 204 | 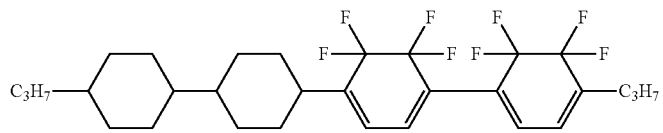 |
| 205 | 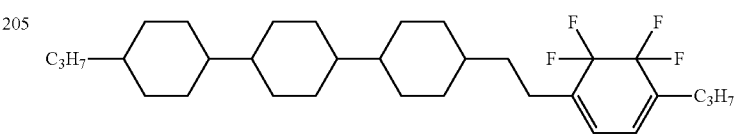 |
| 206 | 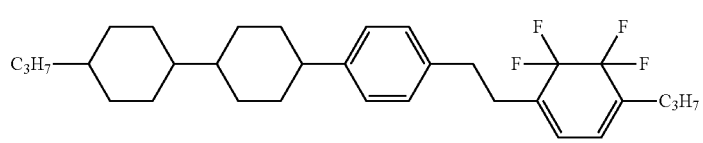 |
| 207 | 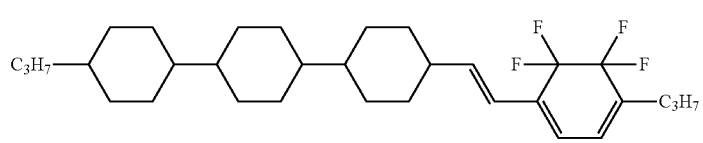 |
| 208 | 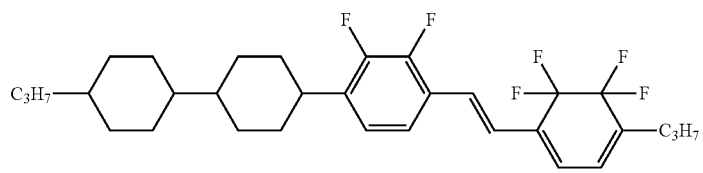 |
| 209 | 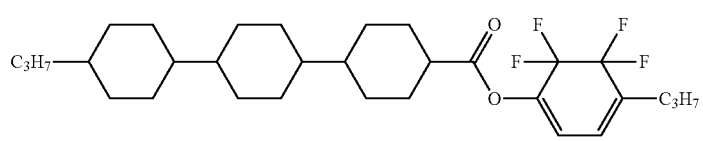 |
| 210 | 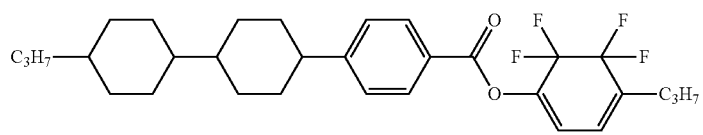 |
| 211 | 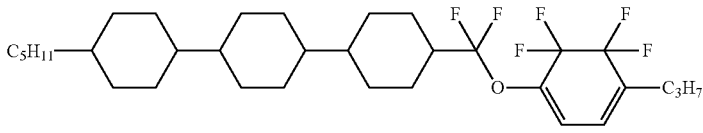 |
| 212 | 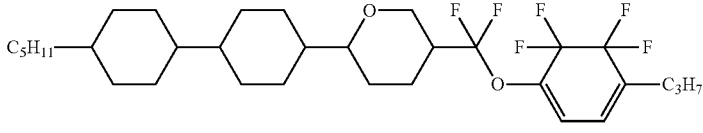 |
| 213 | 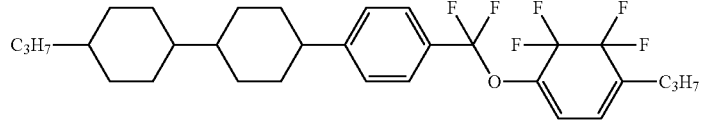 |
| 214 | 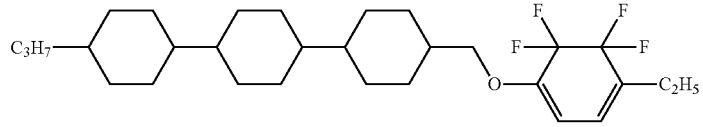 |

| No. | |
|---|---|
| 215 | 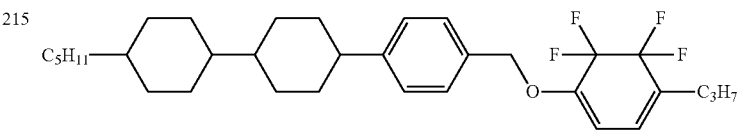 |
| 216 | 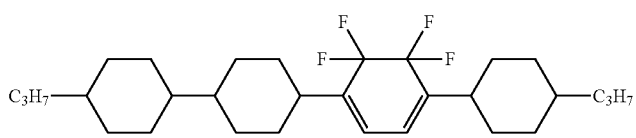 |
| 217 | 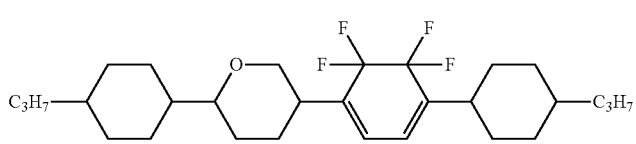 |
| 218 | 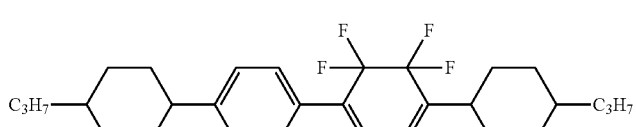 |
| 219 | 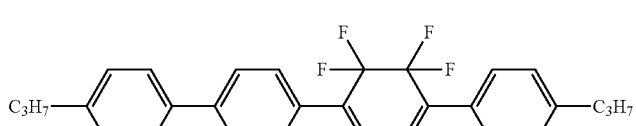 |
| 220 | 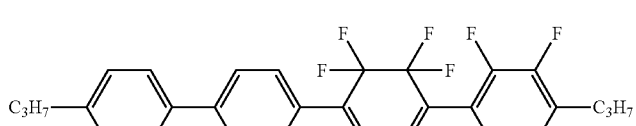 |
| 221 | 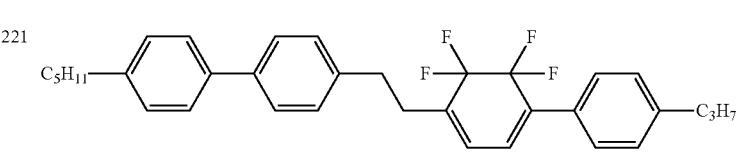 |
| 222 | 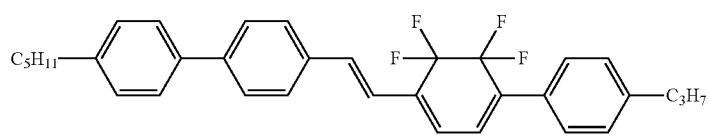 |
| 223 | 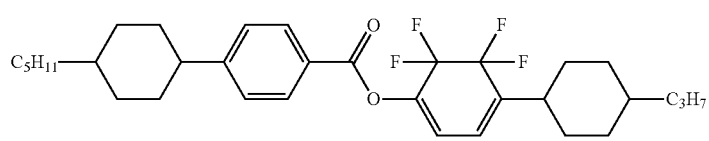 |
| 224 | 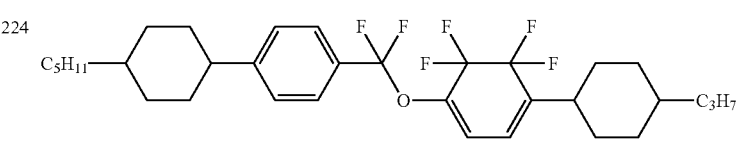 |
| 225 | 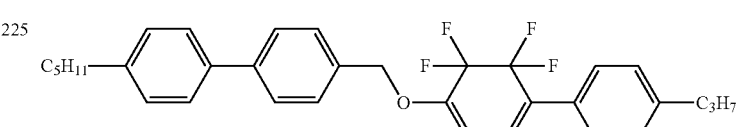 |

-continued

| No. | |
|---|---|
| 226 | 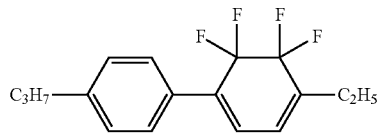 |
| 227 | 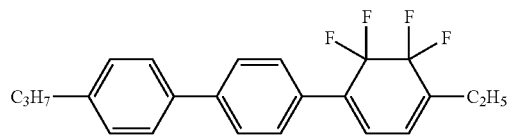 |
| 228 | 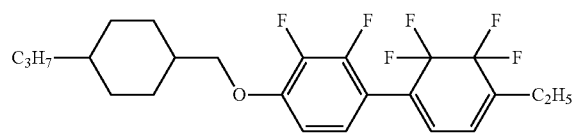 |
| 229 | 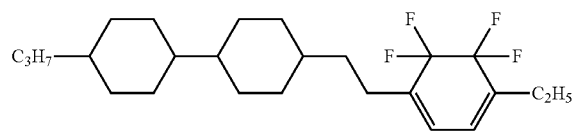 |

Comparative Example 1

A comparative compound (C-1) that was a compound similar to the compound (No. 76) of the present invention was synthesized.

Synthesis of Comparative Compound (C-1)

A comparative compound (C-1) was synthesized by performing the same operations up to the third step through use of a compound (S-29) synthesized by a general method instead of the compound (S-13) in Example 4.

Chemical shift δ (ppm; $CDCl_3$): 6.86 (d, 2H), 2.76 (tt, 1H), 2.65 (q, 2H), 1.88-1.82 (m, 4H), 1.75 (t, 4H), 1.43 (q, 2H), 1.31 (sex, 2H), 1.21 (t, 3H), 1.15-0.81 (m, 11H), 0.87 (t, 3H).

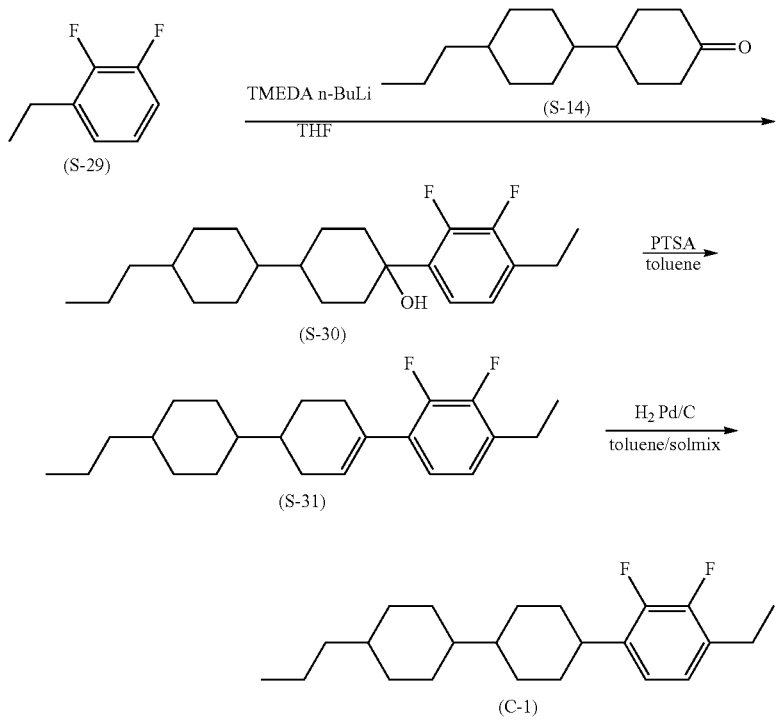

A liquid crystal composition containing 85 wt % of a base liquid crystal and 15 wt % of the obtained compound (C-1) was prepared. The dielectric anisotropy (Δ∈) of the obtained liquid crystal composition was measured, and the measured value was extrapolated to calculate an extrapolated value of the dielectric anisotropy (Δ∈) of the liquid crystal compound (C-1). The value was as described below.

Dielectric anisotropy (Δ∈)=−3.27.

When the compound (No. 76) of the present invention is compared to the compound (C-1), the compound (No. 76) (Δ∈=−4.94) of the present invention is more excellent from the viewpoint of exhibiting large negative dielectric anisotropy.

Comparative Example 2

A comparative compound (C-2) that was a compound similar to the compound (No. 162) of the present invention was synthesized.

Synthesis of Comparative Compound (C-2)

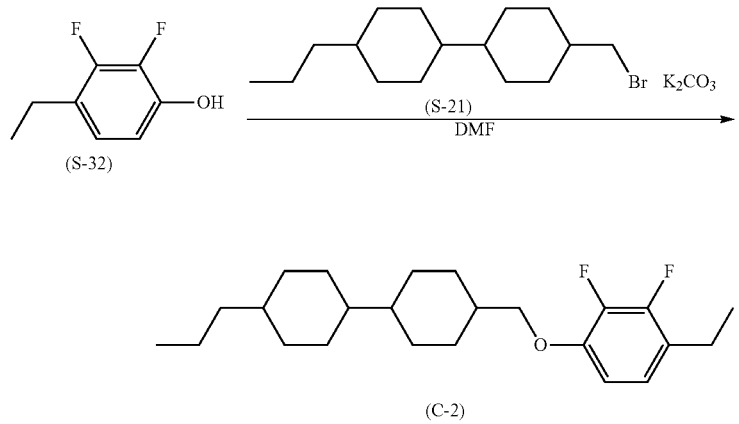

A comparative compound (C-2) was synthesized by performing the same operations as those in the first step through use of a compound (S-32) synthesized by a general method instead of the compound (S-20) in Example 5.

Chemical shift δ (ppm; CDCl$_3$): 6.80 (dt, 2H), 6.65 (dt, 1H), 3.78 (d, 2H), 2.60 (q, 2H), 1.93-1.90 (m, 2H), 1.77-1.69 (m, 7H), 1.30 (sex, 2H), 1.20 (t, 3H), 1.17-0.80 (m, 16H), 0.86 (t, 3H).

A liquid crystal composition containing 85 wt % of a base liquid crystal and 15 wt % of the obtained comparative compound (C-2) was prepared. The dielectric anisotropy (Δ∈) of the obtained liquid crystal composition was measured, and the measured value was extrapolated to calculate an extrapolated value of the dielectric anisotropy (Δ∈) of the liquid crystal compound (C-2). The value was as described below.

Dielectric anisotropy (Δ∈)=−4.82

When the compound (No. 162) of the present invention is compared to the comparative compound (C-2), the compound (No. 162) (Δ∈=−6.30) of the present invention is more excellent from the viewpoint of exhibiting large negative dielectric anisotropy.

1-2. Example of Composition (1)

The liquid crystal composition (1) of the present invention is described in detail by way of Examples. The present invention is not limited to these Examples. The present invention also includes a mixture obtained by mixing at least two components of the composition of Examples. Compounds in Examples are represented by symbols based on the definitions of Table 2 shown below. In Table 2, a configuration regarding 1, 4-cyclohexylene is a trans configuration. In Examples, numerical numbers in parentheses following the symbols correspond to numbers of the compounds. A symbol (-) refers to other liquid crystal compounds. A ratio (percentage) of the liquid crystal compound is a weight percentage (wt %) based on the total weight of the liquid crystal composition. Finally, physical property values of the compositions were summarized. The physical properties were measured in accordance with the methods described above and described directly without extrapolating measured values.

TABLE 1

| Table Notation of compound using symbol R—(A$_1$)—Z$_1$— ..... —Z$_n$—(A$_n$)=R' | |
|---|---|
| 1) Left terminal group R— | Symbol |
| C$_n$N$_{2n+1}$— | n- |
| C$_n$N$_{2n+1}$O— | nO— |
| C$_m$H$_{2m+1}$OC$_n$H$_{2n}$— | mOn- |
| CH$_2$=CH— | V— |
| C$_n$H$_{2n+1}$—CH=CH— | nV— |
| CH$_2$=CH—C$_n$H$_{2n}$— | Vn- |
| C$_m$H$_{2m+1}$—CH=CH—C$_n$H$_{2n}$— | mVn- |
| CF$_2$=CH— | VFF— |
| CF$_2$=CH—C$_n$H$_{2n}$— | VFFn- |
| 2) Right terminal group —R' | Symbol |
| —C$_n$H$_{2n+1}$ | -n |
| —OC$_n$N$_{2n+1}$ | —On |
| —COOCH$_3$ | —EMe |
| —CH=CH$_2$ | —V |
| —CH=CH—C$_n$H$_{2n+1}$ | —Vn |
| —C$_n$H$_{2n}$—CH=CH$_2$ | -nV |
| —C$_m$H$_{2m}$—CH=CH—C$_n$N$_{2n+1}$ | -mVn |
| —CH=CF$_2$ | —VFF |
| —F | —F |
| —Cl | —CL |
| —OCF$_3$ | —OCF3 |

TABLE 1-continued

Table Notation of compound using symbol
R—(A₁)—Z₁— . . . . . —Zₙ—(Aₙ)=R'

| | |
|---|---|
| —OCF₂H | —OCF2H |
| —CF₃ | —CF3 |
| —OCH=CH—CF₂H | —OVCF2H |
| —C≡N | —C |

| 3) Linking group —Zₙ— | Symbol |
|---|---|
| —CₙN₂ₙ— | n |
| —COO— | E |
| —CH=CH— | V |
| —CH₂O— | 1O |
| —OCH₂— | O1 |
| —CF₂O— | X |
| —C≡C— | T |

| 4) Ring structure —Aₙ— | Symbol |
|---|---|
|  | H |
|  | B |
| 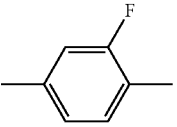 | B(F) |
| 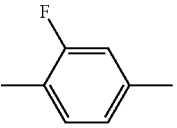 | B(2F) |
| 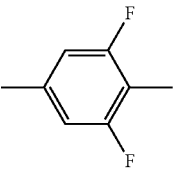 | B(F,F) |
| 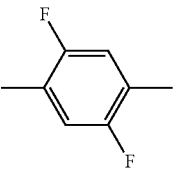 | B(2F,5F) |
| 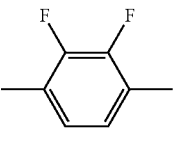 | B(2F,3F) |
|  | Py |
|  | G |
| 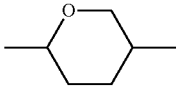 | Dh |
| 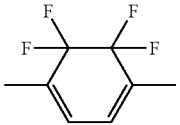 | Cd(F4) |
| 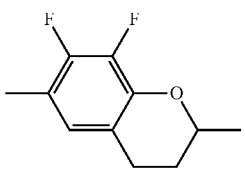 | Cro(7F,8F) |

5) Notation example

Example 1 3-BBCd(F4)

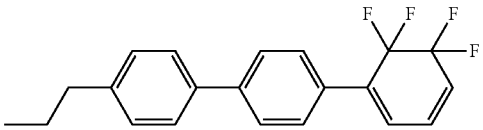

Example 2 3-HBB(2F,3F)-O2

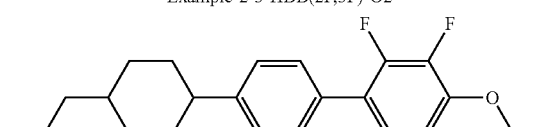

Example 3 3-HH-4

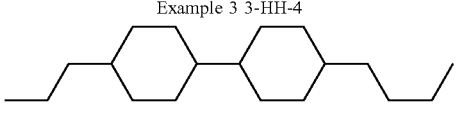

Example 4 3-HBB(F,F)-F

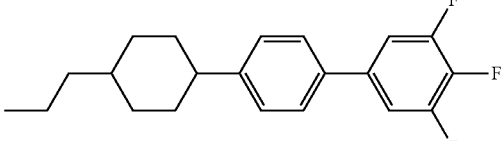

Example 11

| | | |
|---|---|---|
| 3-BCd(F4) | (No. 13) | 3% |
| 2-HB—C | (5-1) | 5% |
| 3-HB—C | (5-1) | 9% |
| 3-HB—O2 | (13-5) | 15% |
| 2-BTB-1 | (13-10) | 3% |
| 3-HHB—F | (3-1) | 4% |
| 3-HHB-1 | (14-1) | 8% |
| 3-HHB—O1 | (14-1) | 5% |
| 3-HHB-3 | (14-1) | 14% |

-continued

| | | |
|---|---|---|
| 3-HHEB—F | (3-10) | 4% |
| 5-HHEB—F | (3-10) | 4% |
| 2-HHB(F)—F | (3-2) | 7% |
| 3-HHB(F)—F | (3-2) | 7% |
| 5-HHB(F)—F | (3-2) | 7% |
| 3-HHB(F,F)—F | (3-3) | 5% |

NI = 94.6° C.;
Δn = 0.096;
Δε = 4.2;
η = 18.8 mPa · s.

Example 12

| | | |
|---|---|---|
| 3-BBCd(F4) | (No. 107) | 3% |
| 3-HHB(F,F)—F | (3-3) | 9% |
| 3-H2HB(F,F)—F | (3-15) | 8% |
| 4-H2HB(F,F)—F | (3-15) | 8% |
| 5-H2HB(F,F)—F | (3-15) | 8% |
| 3-HBB(F,F)—F | (3-24) | 18% |
| 5-HBB(F,F)—F | (3-24) | 20% |
| 3-H2BB(F,F)—F | (3-27) | 10% |
| 5-HHBB(F,F)—F | (4-6) | 3% |
| 5-HHEBB—F | (4-17) | 2% |
| 3-HH2BB(F,F)—F | (4-15) | 3% |
| 1O1—HBBH-4 | (15-1) | 4% |
| 1O1—HBBH-5 | (15-1) | 4% |

NI = 96.4° C.;
Δn = 0.117;
Δε = 8.6;
η = 36.3 mPa · s.

The pitch was 65.7 μm when 0.25 part of the compound (Op-05) was added to 100 parts of the composition.

Example 13

| | | |
|---|---|---|
| 3-HDhCd(F4)-3 | (No. 94) | 3% |
| 5-HB—CL | (2-2) | 11% |
| 3-HH-4 | (13-1) | 8% |
| 3-HHB-1 | (14-1) | 5% |
| 3-HHB(F,F)—F | (3-3) | 8% |
| 3-HBB(F,F)—F | (3-24) | 17% |
| 5-HBB(F,F)—F | (3-24) | 15% |
| 3-HHEB(F,F)—F | (3-12) | 10% |
| 4-HHEB(F,F)—F | (3-12) | 3% |
| 5-HHEB(F,F)—F | (3-12) | 3% |
| 2-HBEB(F,F)—F | (3-39) | 3% |
| 3-HBEB(F,F)—F | (3-39) | 5% |
| 5-HBEB(F,F)—F | (3-39) | 3% |
| 3-HHBB(F,F)—F | (4-6) | 6% |

NI = 80.2° C.;
Δn = 0.102;
Δε = 8.1;
η = 24.3 mPa · s.

Example 14

| | | |
|---|---|---|
| 3-HHCd(F4)-3 | (No. 76) | 3% |
| 5-HB—CL | (2-2) | 3% |
| 7-HB(F)—F | (2-3) | 7% |
| 3-HH-4 | (13-1) | 9% |
| 3-HH—EMe | (13-2) | 23% |
| 3-HHEB—F | (3-10) | 8% |
| 5-HHEB—F | (3-10) | 8% |
| 3-HHEB(F,F)—F | (3-12) | 10% |
| 4-HHEB(F,F)—F | (3-12) | 5% |

-continued

| | | |
|---|---|---|
| 4-HGB(F,F)—F | (3-103) | 5% |
| 5-HGB(F,F)—F | (3-103) | 6% |
| 2-H2GB(F,F)—F | (3-106) | 4% |
| 3-H2GB(F,F)—F | (3-106) | 5% |
| 5-GHB(F,F)—F | (3-109) | 4% |

NI = 80.8° C.;
Δn = 0.065;
Δε = 4.9;
η = 20.1 mPa · s.

Example 15

| | | |
|---|---|---|
| 3-HH1OCd(F4)-3 | (No. 162) | 3% |
| 3-HB—O1 | (13-5) | 15% |
| 3-HH-4 | (13-1) | 5% |
| 3-HB(2F,3F)—O2 | (6-1) | 12% |
| 5-HB(2F,3F)—O2 | (6-1) | 12% |
| 2-HHB(2F,3F)-1 | (7-1) | 12% |
| 3-HHB(2F,3F)-1 | (7-1) | 12% |
| 3-HHB(2F,3F)—O2 | (7-1) | 11% |
| 5-HHB(2F,3F)—O2 | (7-1) | 12% |
| 3-HHB-1 | (14-1) | 6% |

NI = 83.8° C.;
Δn = 0.089;
Δε = −3.4;
η = 36.4 mPa · s.

Example 16

| | | |
|---|---|---|
| 3-HH2Cd(F4)-3 | (No. 136) | 3% |
| 3-HH-4 | (13-1) | 8% |
| 3-H2B(2F,3F)—O2 | (6-4) | 21% |
| 5-H2B(2F,3F)—O2 | (6-4) | 21% |
| 2-HHB(2F,3CL)—O2 | (7-12) | 2% |
| 3-HHB(2F,3CL)—O2 | (7-12) | 2% |
| 4-HHB(2F,3CL)—O2 | (7-12) | 2% |
| 5-HHB(2F,3CL)—O2 | (7-12) | 2% |
| 3-HBB(2F,3F)—O2 | (7-7) | 9% |
| 5-HBB(2F,3F)—O2 | (7-7) | 9% |
| V—HHB-1 | (14-1) | 6% |
| 3-HHB-3 | (14-1) | 6% |
| 3-HHEBH-3 | (15-6) | 3% |
| 3-HHEBH-4 | (15-6) | 3% |
| 3-HHEBH-5 | (15-6) | 3% |

NI = 92.0° C.;
Δn = 0.100;
Δε = −4.0;
η = 29.9 mPa · s.

Example 17

| | | |
|---|---|---|
| 3-BCd(F4)B-3 | (No. 126) | 3% |
| 2-HH-5 | (13-1) | 3% |
| 3-HH-4 | (13-1) | 15% |
| 3-HH-5 | (13-1) | 4% |
| 3-HB—O2 | (13-5) | 12% |
| 3-H2B(2F,3F)—O2 | (6-4) | 15% |
| 5-H2B(2F,3F)—O2 | (6-4) | 15% |
| 3-HHB(2F,3CL)—O2 | (7-12) | 5% |
| 2-HBB(2F,3F)—O2 | (7-7) | 3% |

-continued

| | | |
|---|---|---|
| 3-HBB(2F,3F)—O2 | (7-7) | 8% |
| 5-HBB(2F,3F)—O2 | (7-7) | 7% |
| 3-HHB-1 | (14-1) | 3% |
| 3-HHB-3 | (14-1) | 4% |
| 3-HHB—O1 | (14-1) | 3% |

NI = 72.3° C.;
$\Delta n$ = 0.095;
$\Delta \varepsilon$ = −4.0;
$\eta$ = 19.8 mPa · s.

Example 18

| | | |
|---|---|---|
| 3-BBCd(F4)-3 | (No. 106) | 3% |
| 2-HH-3 | (13-1) | 21% |
| 3-HH-4 | (13-1) | 9% |
| 1-BB-3 | (13-8) | 9% |
| 3-HB—O2 | (13-5) | 2% |
| 3-BB(2F,3F)—O2 | (6-3) | 9% |
| 5-BB(2F,3F)—O2 | (6-3) | 6% |
| 2-HH1OB(2F,3F)—O2 | (7-5) | 12% |
| 3-HH1OB(2F,3F)—O2 | (7-5) | 19% |
| 3-HHB-1 | (14-1) | 5% |
| 3-HHB—O1 | (14-1) | 3% |
| 2-BBB(2F)-5 | (14-8) | 2% |

NI = 72.3° C.;
$\Delta n$ = 0.101;
$\Delta \varepsilon$ = −3.1;
$\eta$ = 16.2 mPa · s.

Example 19

| | | |
|---|---|---|
| 3-HBCd(F4)-3 | (No. 82) | 3% |
| 2-HH-3 | (13-1) | 16% |
| 7-HB-1 | (13-5) | 10% |
| 5-HB—O2 | (13-5) | 8% |
| 3-HB(2F,3F)—O2 | (6-1) | 17% |
| 5-HB(2F,3F)—O2 | (6-1) | 16% |
| 3-HHB(2F,3CL)—O2 | (7-12) | 2% |
| 4-HHB(2F,3CL)—O2 | (7-12) | 2% |
| 5-HHB(2F,3CL)—O2 | (7-12) | 2% |
| 3-HH1OCro(7F,8F)-5 | (10-6) | 4% |
| 5-HBB(F)B-2 | (15-5) | 10% |
| 5-HBB(F)B-3 | (15-5) | 10% |

NI = 74.4° C.;
$\Delta n$ = 0.106;
$\Delta \varepsilon$ = −2.5;
$\eta$ = 23.1 mPa · s.

Example 20

| | | |
|---|---|---|
| 3-BCd(F4)-3 | (No. 12) | 3% |
| 1-BB-3 | (13-8) | 9% |
| 3-HH—V | (13-1) | 27% |
| 3-BB(2F,3F)—O2 | (6-3) | 12% |
| 2-HH1OB(2F,3F)—O2 | (7-5) | 20% |
| 3-HH1OB(2F,3F)—O2 | (7-5) | 14% |
| 3-HHB-1 | (14-1) | 9% |
| 2-BBB(2F)-5 | (14-8) | 6% |

NI = 73.3° C.;
$\Delta n$ = 0.107;
$\Delta \varepsilon$ = −3.1;
$\eta$ = 17.0 mPa · s.

Example 21

| | | |
|---|---|---|
| 3-HCd(F4)-3 | (No. 4) | 3% |
| 3-GB(F)B(F,F)XB(F,F)—F | (4-57) | 4% |
| 3-BB(F)B(F,F)XB(F,F)—F | (4-47) | 3% |
| 4-BB(F)B(F,F)XB(F,F)—F | (4-47) | 6% |
| 5-BB(F)B(F,F)XB(F,F)—F | (4-47) | 3% |
| 3-HH—V | (13-1) | 40% |
| 3-HH—V1 | (13-1) | 7% |
| 3-HHEH-5 | (14-13) | 3% |
| 3-HHB-1 | (14-1) | 4% |
| V—HHB-1 | (14-1) | 5% |
| V2—BB(F)B-1 | (14-6) | 5% |
| 1V2—BB—F | (2-1) | 3% |
| 3-BB(F,F)XB(F,F)—F | (3-97) | 11% |
| 3-HHBB(F,F)—F | (4-6) | 3% |

NI = 77.4° C.;
$\Delta n$ = 0.103;
$\Delta \varepsilon$ = 5.6;
$\eta$ = 12.7 mPa · s.

Example 22

| | | |
|---|---|---|
| 3-BCd(F4) | (No. 13) | 2% |
| 3-BBCd(F4) | (No. 107) | 2% |
| 3-GB(F)B(F,F)XB(F,F)—F | (4-57) | 5% |
| 3-BB(F)B(F,F)XB(F,F)—F | (4-47) | 3% |
| 4-BB(F)B(F,F)XB(F,F)—F | (4-47) | 7% |
| 5-BB(F)B(F,F)XB(F,F)—F | (4-47) | 3% |
| 3-HH—V | (13-1) | 41% |
| 3-HH—V1 | (13-1) | 7% |
| 3-HHEH-5 | (14-13) | 3% |
| 3-HHB-1 | (14-1) | 4% |
| V—HHB-1 | (14-1) | 5% |
| V2—BB(F)B-1 | (14-6) | 5% |
| 1V2—BB—F | (2-1) | 3% |
| 3-BB(F,F)XB(F,F)—F | (3-97) | 4% |
| 3-GB(F,F)XB(F,F)—F | (3-113) | 3% |
| 3-HHBB(F,F)—F | (4-6) | 3% |

NI = 78.5° C.;
$\Delta n$ = 0.102;
$\Delta \varepsilon$ = 6.1;
$\eta$ = 13.8 mPa · s.

Example 23

| | | |
|---|---|---|
| 3-HDhCd(F4)-3 | (No. 94) | 3% |
| 2-HH-3 | (13-1) | 16% |
| 7-HB-1 | (13-5) | 10% |
| 5-HB—O2 | (13-5) | 5% |
| 3-HB(2F,3F)—O2 | (6-1) | 16% |
| 5-HB(2F,3F)—O2 | (6-1) | 16% |
| 3-HHB(2F,3CL)—O2 | (7-12) | 3% |
| 4-HHB(2F,3CL)—O2 | (7-12) | 3% |
| 3-HDhB(2F,3F)—O2 | (7-3) | 3% |
| 3-HH1OCro(7F,8F)-5 | (10-6) | 5% |
| 5-HBB(F)B-2 | (15-5) | 10% |
| 5-HBB(F)B-3 | (15-5) | 10% |

NI = 77.0° C.;
$\Delta n$ = 0.105;
$\Delta \varepsilon$ = −2.8;
$\eta$ = 25.9 mPa · s.

Example 24

| | | |
|---|---|---|
| 3-HHCd(F4)-3 | (No. 76) | 3% |
| 1V2—BEB(F,F)—C | (5-15) | 6% |
| 3-HB—C | (5-1) | 18% |
| 2-BTB-1 | (13-10) | 10% |
| 5-HH—VFF | (13-1) | 27% |
| 3-HHB-1 | (14-1) | 4% |
| VFF—HHB-1 | (14-1) | 8% |
| VFF2—HHB-1 | (14-1) | 11% |
| 3-H2BTB-2 | (14-17) | 5% |
| 3-H2BTB-3 | (14-17) | 4% |
| 3-H2BTB-4 | (14-17) | 4% |

NI = 82.5° C.;
Δn = 0.131;
Δε = 6.3;
η = 14.3 mPa · s.

Example 25

| | | |
|---|---|---|
| 3-HH1OCd(F4)-3 | (No. 162) | 4% |
| 3-HB—O2 | (13-5) | 10% |
| 5-HB-CL | (2-2) | 13% |
| 3-HBB(F,F)—F | (3-24) | 7% |
| 3-PyB(F)—F | (3-81) | 10% |
| 5-PyB(F)—F | (3-81) | 9% |
| 3-PyBB—F | (3-80) | 10% |
| 4-PyBB—F | (3-80) | 8% |
| 5-PyBB—F | (3-80) | 9% |
| 5-HBB(F)B-2 | (15-5) | 10% |
| 5-HBB(F)B-3 | (15-5) | 10% |

NI = 97.9° C.;
Δn = 0.187;
Δε = 7.3;
η = 41.4 mPa · s.

INDUSTRIAL APPLICABILITY

The liquid crystal compound of the present invention has high stability to heat, light, and the like, a high clearing point, a low minimum temperature of a liquid crystal phase, a small viscosity, suitable optical anisotropy, large negative dielectric anisotropy, a suitable elastic constant, and excellent compatibility with other liquid crystal compounds. The liquid crystal composition contains the compound and has a high maximum temperature of a nematic phase, a low minimum temperature of a nematic phase, a small viscosity, suitable optical anisotropy, large negative dielectric anisotropy, and a suitable elastic constant. The composition has suitable balance regarding at least two physical properties. The liquid crystal display device of the present invention includes the composition and has a wide temperature range in which the device can be used, a short response time, a large voltage holding ratio, a low threshold voltage, a large contrast ratio, and a long service life. Therefore, the device can be widely used in displays of personal computers, televisions, and the like.

The invention claimed is:

1. A compound of formula (1-8), formula (1-10):

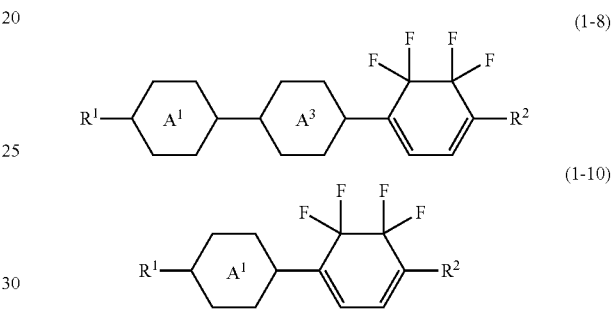

in which:
R$^1$ represents C$_3$H$_7$;
a ring A$^1$, and a ring A$^3$ each independently represent 5,5,6,6-tetrafluoro-1,3-cyclohexadiene-1,4-diyl; and
R$^2$ represents hydrogen.

2. A liquid crystal composition, comprising at least one of the compounds of claim 1.

3. A liquid crystal composition according to claim 2, further comprising at least one compound selected from the group consisting of compounds represented by the following formulae (6) to (12):

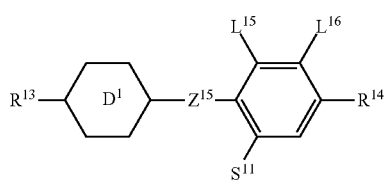

(6)

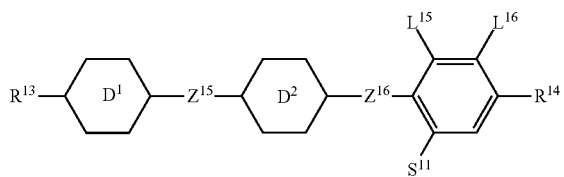

(7)

-continued

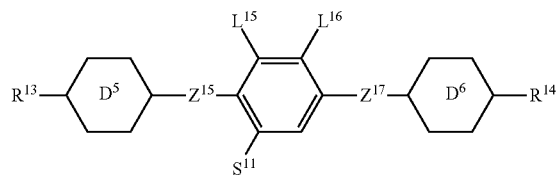

(8)

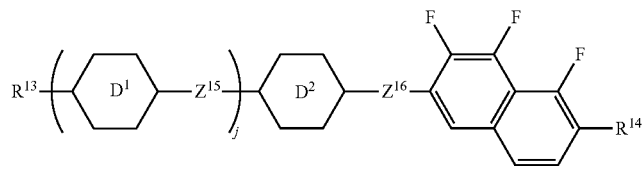

(9)

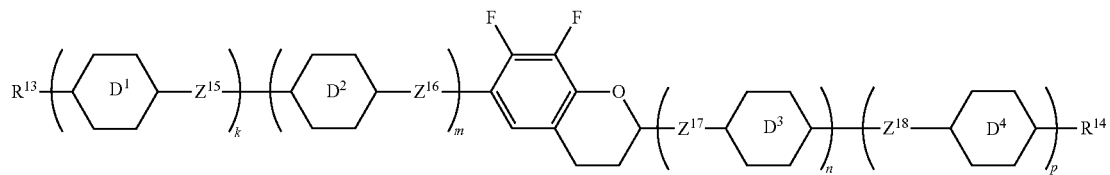

(10)

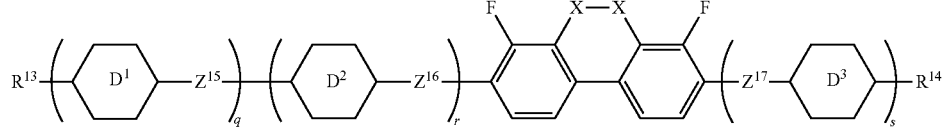

(11)

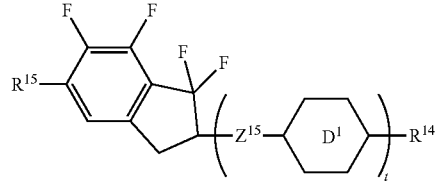

(12)

in the formulae (6) to (12):
  $R^{13}$ represents an alkyl having 1 to 10 carbon atoms or an alkenyl having 2 to 10 carbon atoms, and in the alkyl and the alkenyl, at least one —CH$_2$— may be substituted by —O— and at least one hydrogen may be substituted by fluorine;
  $R^{14}$ represents an alkyl having 1 to 10 carbon atoms, and in the alkyl, at least one —CH$_2$— may be substituted by —O— and at least one hydrogen may be substituted by fluorine;
  $R^{15}$ represents hydrogen, fluorine, an alkyl having 1 to 10 carbon atoms, or an alkenyl having 2 to 10 carbon atoms, and in the alkyl and the alkenyl, at least one —CH$_2$— may be substituted by —O— and at least one hydrogen may be substituted by fluorine;
  $S^{11}$ represents hydrogen or methyl;
  X represents —CF$_2$—, —O—, or —CHF—;
  a ring $D^1$, a ring $D^2$, a ring $D^3$, and a ring $D^4$ each independently represent 1,4-cyclohexylene, 1,4-cyclohexenylene, 1,4-phenylene in which at least one hydrogen may be substituted by fluorine, tetrahydropyran-2,5-diyl, or decahydronaphthalene-2,6-diyl;
  a ring $D^5$ and a ring $D^6$ each independently represent 1,4-cyclohexylene, 1,4-cyclohexenylene, 1,4-phenylene, tetrahydropyran-2,5-diyl, or decahydronaphthalene-2,6-diyl;
  $Z^{15}$, $Z^{16}$, $Z^{17}$, and $Z^{18}$ each independently represent a single bond, —CH$_2$CH$_2$—, —COO—, —CH$_2$O—, —OCF$_2$—, or —OCF$_2$CH$_2$CH$_2$—;
  $L^{15}$ and $L^{16}$ each independently represent fluorine or chlorine; and
  j, k, m, n, p, q, r, and s each independently represent 0 or 1, a sum of k, n, and p is 1 or 2, a sum of q, r, and s is 0, 1, 2, or 3, and t represents 1, 2, or 3.

4. A liquid crystal composition according to claim 2, further comprising at least one compound selected from the group consisting of compounds represented by the following formulae (13) to (15):

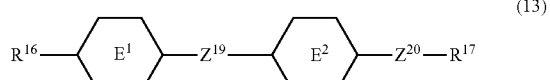

(13)

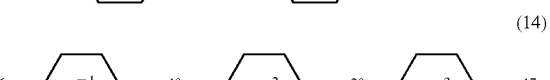

(14)

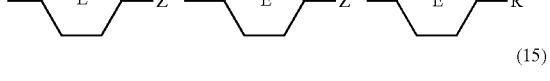

(15)

in the formulae (13) to (15):
  $R^{16}$ and $R^{17}$ each independently represent an alkyl having 1 to 10 carbon atoms or an alkenyl having 2 to 10 carbon atoms, and in the alkyl and the alkenyl, at least one —CH$_2$— may be substituted by —O— and at least one hydrogen may be substituted by fluorine;
a ring E$^1$, a ring E$^2$, a ring E$^3$, and a ring E$^4$ each independently represent 1,4-cyclohexylene, 1,4-phenylene, 2-fluoro-1,4-phenylene, 2,5-difluoro-1,4-phenylene, or pyrimidine-2,5-diyl; and
Z$^{19}$, Z$^{20}$, and Z$^{21}$ each independently represent a single bond, —CH$_2$CH$_2$—, —CH=CH—, —C≡C—, or —COO—.

5. A liquid crystal composition according to claim 2, further comprising at least one compound selected from the group consisting of compounds represented by the following formulae (2) to (4):

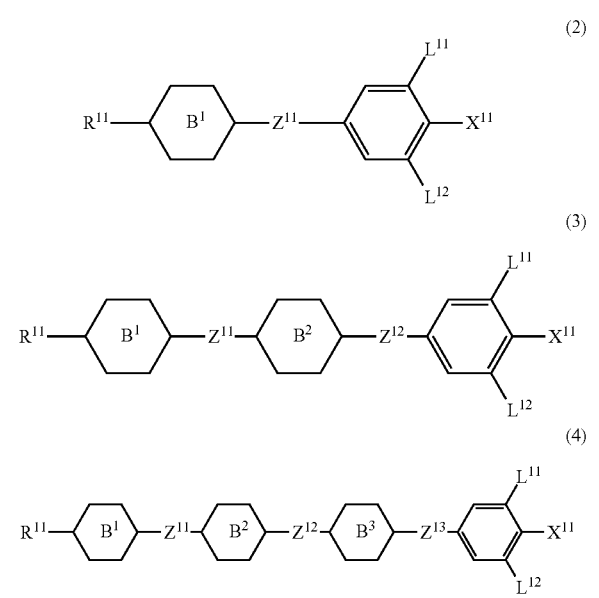

in the formulae (2) to (4):
R$^{11}$ represents an alkyl having 1 to 10 carbon atoms or an alkenyl having 2 to 10 carbon atoms, and in the alkyl and the alkenyl, at least one hydrogen may be substituted by fluorine and at least one —CH$_2$— may be substituted by —O—;
X$^{11}$ represents fluorine, chlorine, —OCF$_3$, —OCHF$_2$, —CF$_3$, —CHF$_2$, —CF$_2$CHF$_2$, or —OCF$_2$CHFCF$_3$;
a ring B$^1$, a ring B$^2$, and a ring B$^3$ each independently represent 1,4-cyclohexylene, 1,4-phenylene in which at least one hydrogen may be substituted by fluorine, tetrahydropyran-2,5-diyl or pyrimidine-2,5-diyl;
Z$^{11}$, Z$^{12}$, and Z$^{13}$ each independently represent a single bond, —CH$_2$CH$_2$—, —CH=CH—, —C≡C—, —COO—, —CF$_2$O—, —OCF$_2$—, —CH$_2$O—, or —(CH$_2$)$_4$—; and
L$^{11}$ and L$^{12}$ each independently represent hydrogen or fluorine.

6. A liquid crystal composition according to claim 2, further comprising at least one compound selected from the group consisting of compounds represented by the following formula (5):

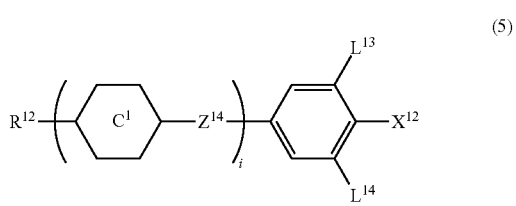

in the formula (5):
R$^{12}$ represents an alkyl having 1 to 10 carbon atoms or an alkenyl having 2 to 10 carbon atoms, and in the alkyl and the alkenyl, at least one hydrogen may be substituted by fluorine and at least one —CH$_2$— may be substituted by —O—;
X$^{12}$ represents —C≡N or —C≡C—C≡N;
a ring C$^1$ represents 1,4-cyclohexylene, 1,4-phenylene in which at least one hydrogen may be substituted by fluorine, tetrahydropyran-2,5-diyl, 1,3-dioxane-2,5-diyl, or pyrimidine-2,5-diyl;
Z$^{14}$ represents a single bond, —CH$_2$CH$_2$—, —C≡C—, —COO—, —CF$_2$O—, —OCF$_2$—, or —CH$_2$O—;
L$^{13}$ and L$^{14}$ each independently represent hydrogen or fluorine; and
i represents 1, 2, 3, or 4.

7. A liquid crystal composition according to claim 2, further comprising at least one optically active compound and/or polymerizable compound.

8. A liquid crystal composition according to claim 2, further comprising at least one antioxidant and/or UV absorber.

9. A liquid crystal display device, comprising the liquid crystal composition of claim 2.

* * * * *